(12) United States Patent (10) Patent No.: US 12,599,758 B2
Ryan et al. (45) Date of Patent: Apr. 14, 2026

(54) INTRAVASCULAR BLOOD PUMPS, MOTORS, AND FLUID CONTROL

(71) Applicant: SHIFAMED HOLDINGS, LLC, Campbell, CA (US)

(72) Inventors: Ari Ryan, Sunnyvale, CA (US); Danny Varghai, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 362 days.

(21) Appl. No.: 17/782,675

(22) PCT Filed: Dec. 18, 2020

(86) PCT No.: PCT/US2020/066118
§ 371 (c)(1),
(2) Date: Jun. 6, 2022

(87) PCT Pub. No.: WO2021/127503
PCT Pub. Date: Jun. 24, 2021

(65) Prior Publication Data
US 2023/0033471 A1 Feb. 2, 2023

Related U.S. Application Data

(60) Provisional application No. 62/950,685, filed on Dec. 19, 2019.

(51) Int. Cl.
*A61M 60/17* (2021.01)
*A61M 60/13* (2021.01)
(Continued)

(52) U.S. Cl.
CPC ............ *A61M 60/17* (2021.01); *A61M 60/13* (2021.01); *A61M 60/139* (2021.01);
(Continued)

(58) Field of Classification Search
None
See application file for complete search history.

(56) References Cited

U.S. PATENT DOCUMENTS

| | | | |
|---|---|---|---|
| 1,061,107 A | 5/1913 | Nordmark | |
| 1,596,933 A | 8/1926 | Kister | |
| | (Continued) | | |

FOREIGN PATENT DOCUMENTS

| | | |
|---|---|---|
| CA | 2352234 A1 | 6/2000 |
| CA | 2739899 C | 5/2017 |
| | (Continued) | |

OTHER PUBLICATIONS

Varghai et al.; U.S. Appl. No. 17/794,002 entitled "Intravascular blood pumps, motors, and fluid control," filed Jul. 20, 2022.
(Continued)

*Primary Examiner* — Mallika D Fairchild
(74) *Attorney, Agent, or Firm* — Shay Glenn LLP

(57) ABSTRACT

Intravascular blood pumps systems and methods of use. The blood pump system includes a catheter portion having a distal blood pump with one or more distal collapsible impellers. The system can include a clean purge fluid pathway to carry clean fluid distally to the blood pump and a purge fluid return pathway to carry return fluid proximally into an external motor and out a proximal end of the motor, and optionally to a waste reservoir.

21 Claims, 46 Drawing Sheets

(51) Int. Cl.

| | |
|---|---|
| *A61M 60/139* | (2021.01) |
| *A61M 60/237* | (2021.01) |
| *A61M 60/414* | (2021.01) |
| *A61M 60/585* | (2021.01) |
| *A61M 60/808* | (2021.01) |
| *A61M 60/81* | (2021.01) |
| *A61M 60/818* | (2021.01) |
| *A61M 60/829* | (2021.01) |
| *A61M 60/89* | (2021.01) |

(52) U.S. Cl.

CPC ........ *A61M 60/237* (2021.01); *A61M 60/414* (2021.01); *A61M 60/585* (2021.01); *A61M 60/808* (2021.01); *A61M 60/81* (2021.01); *A61M 60/818* (2021.01); *A61M 60/829* (2021.01); *A61M 60/89* (2021.01)

(56) References Cited

U.S. PATENT DOCUMENTS

| | | |
|---|---|---|
| 3,152,618 A | 10/1964 | Rothermel et al. |
| 3,175,555 A | 3/1965 | Ling |
| 3,178,833 A | 4/1965 | Gulbransen, Jr. |
| 3,208,448 A | 9/1965 | Woodward |
| 3,233,609 A | 2/1966 | Leucci |
| 3,421,497 A | 1/1969 | Chesnut |
| 3,502,412 A | 3/1970 | Burns |
| 3,504,662 A | 4/1970 | Jones |
| 3,505,987 A | 4/1970 | Heilman |
| 3,568,659 A | 3/1971 | Karnegis |
| 3,693,612 A | 9/1972 | Donahoe et al. |
| 3,734,648 A | 5/1973 | Nielson |
| 3,774,243 A | 11/1973 | Ng et al. |
| 3,837,922 A | 9/1974 | Ng et al. |
| 3,841,837 A | 10/1974 | Kitrilakis et al. |
| 3,860,968 A | 1/1975 | Shapiro |
| 3,919,722 A | 11/1975 | Harmison |
| 4,015,590 A | 4/1977 | Normann |
| 4,037,984 A | 7/1977 | Rafferty et al. |
| 4,046,137 A | 9/1977 | Curless et al. |
| 4,058,857 A | 11/1977 | Runge et al. |
| 4,093,726 A | 6/1978 | Winn et al. |
| 4,135,253 A | 1/1979 | Reich et al. |
| 4,142,845 A | 3/1979 | Lepp et al. |
| 4,173,796 A | 11/1979 | Jarvik |
| 4,190,047 A | 2/1980 | Jacobsen et al. |
| 4,255,821 A | 3/1981 | Carol et al. |
| 4,289,141 A | 9/1981 | Cormier |
| 4,310,930 A | 1/1982 | Goldowsky |
| 4,311,133 A | 1/1982 | Robinson |
| 4,328,806 A | 5/1982 | Cooper |
| 4,370,983 A | 2/1983 | Lichtenstein |
| 4,381,005 A | 4/1983 | Bujan |
| 4,381,567 A | 5/1983 | Robinson et al. |
| 4,382,199 A | 5/1983 | Isaacson |
| 4,389,737 A | 6/1983 | Robinson et al. |
| 4,397,049 A | 8/1983 | Robinson et al. |
| 4,407,304 A | 10/1983 | Lieber et al. |
| 4,506,658 A | 3/1985 | Casile |
| 4,515,589 A | 5/1985 | Austin et al. |
| 4,522,195 A | 6/1985 | Schiff |
| 4,524,466 A | 6/1985 | Hall et al. |
| 4,551,073 A | 11/1985 | Schwab |
| 4,576,606 A | 3/1986 | Pol et al. |
| 4,585,004 A | 4/1986 | Brownlee |
| 4,585,007 A | 4/1986 | Uchigaki et al. |
| 4,599,081 A | 7/1986 | Cohen |
| 4,600,405 A | 7/1986 | Zibelin |
| 4,623,350 A | 11/1986 | Lapeyre et al. |
| 4,625,712 A | 12/1986 | Wampler |
| 4,652,265 A | 3/1987 | McDougall |
| 4,662,358 A | 5/1987 | Farrar et al. |
| 4,666,598 A | 5/1987 | Heath et al. |
| 4,675,361 A | 6/1987 | Ward |
| 4,685,910 A | 8/1987 | Schweizer |
| 4,726,379 A | 2/1988 | Altman et al. |
| 4,753,221 A | 6/1988 | Kensey et al. |
| 4,767,289 A | 8/1988 | Parrott et al. |
| 4,771,777 A | 9/1988 | Horzewski et al. |
| 4,779,614 A | 10/1988 | Moise |
| 4,782,817 A | 11/1988 | Singh et al. |
| 4,785,795 A | 11/1988 | Singh |
| 4,802,650 A | 2/1989 | Stricker |
| 4,818,186 A | 4/1989 | Pastrone et al. |
| 4,826,481 A | 5/1989 | Sacks et al. |
| 4,846,152 A | 7/1989 | Wampler et al. |
| 4,846,831 A | 7/1989 | Skillin |
| 4,850,957 A | 7/1989 | Summers |
| 4,888,009 A | 12/1989 | Lederman et al. |
| 4,888,011 A | 12/1989 | Kung et al. |
| 4,902,272 A | 2/1990 | Milder et al. |
| 4,907,592 A | 3/1990 | Harper |
| 4,908,012 A | 3/1990 | Moise et al. |
| 4,919,647 A | 4/1990 | Nash |
| 4,936,759 A | 6/1990 | Clausen et al. |
| 4,961,738 A | 10/1990 | Mackin |
| 4,976,683 A | 12/1990 | Gauthier et al. |
| 4,995,857 A | 2/1991 | Arnold |
| 5,026,367 A | 6/1991 | Leckrone et al. |
| D318,113 S | 7/1991 | Moutafis et al. |
| 5,045,051 A | 9/1991 | Milder et al. |
| 5,046,503 A | 9/1991 | Schneiderman |
| 5,047,147 A | 9/1991 | Chevallet et al. |
| 5,049,134 A | 9/1991 | Golding et al. |
| 5,061,256 A | 10/1991 | Wampler |
| 5,084,064 A | 1/1992 | Barak et al. |
| 5,089,016 A | 2/1992 | Millner et al. |
| 5,090,957 A | 2/1992 | Moutafis et al. |
| 5,092,844 A | 3/1992 | Schwartz et al. |
| 5,092,879 A | 3/1992 | Jarvik |
| 5,112,200 A | 5/1992 | Isaacson et al. |
| 5,112,292 A | 5/1992 | Hwang et al. |
| 5,114,399 A | 5/1992 | Kovalcheck |
| 5,116,305 A | 5/1992 | Milder et al. |
| 5,139,517 A | 8/1992 | Corral |
| 5,145,333 A | 9/1992 | Smith |
| 5,147,281 A | 9/1992 | Thornton et al. |
| 5,171,264 A | 12/1992 | Merrill |
| 5,180,378 A | 1/1993 | Kung et al. |
| 5,192,314 A | 3/1993 | Daskalakis |
| 5,200,050 A | 4/1993 | Ivory et al. |
| 5,205,721 A | 4/1993 | Isaacson |
| 5,211,546 A | 5/1993 | Isaacson et al. |
| 5,261,411 A | 11/1993 | Hughes |
| 5,270,005 A | 12/1993 | Raible |
| 5,287,858 A | 2/1994 | Hammerslag et al. |
| 5,300,111 A | 4/1994 | Panton et al. |
| 5,300,112 A | 4/1994 | Barr |
| 5,314,418 A | 5/1994 | Takano et al. |
| 5,322,413 A | 6/1994 | Vescovini et al. |
| 5,326,344 A | 7/1994 | Bramm et al. |
| 5,363,856 A | 11/1994 | Hughes et al. |
| 5,397,349 A | 3/1995 | Kolff et al. |
| 5,399,074 A | 3/1995 | Nose et al. |
| 5,405,251 A | 4/1995 | Sipin |
| 5,441,636 A | 8/1995 | Chevallet et al. |
| 5,443,504 A | 8/1995 | Hill |
| 5,486,192 A | 1/1996 | Walinsky et al. |
| 5,487,727 A | 1/1996 | Snider et al. |
| 5,507,629 A | 4/1996 | Jarvik |
| 5,507,795 A | 4/1996 | Chiang et al. |
| 5,510,267 A | 4/1996 | Marshall |
| 5,512,042 A | 4/1996 | Montoya et al. |
| 5,531,789 A | 7/1996 | Yamazaki et al. |
| 5,628,731 A | 5/1997 | Dodge et al. |
| 5,630,835 A | 5/1997 | Brownlee |
| 5,643,172 A | 7/1997 | Kung et al. |
| 5,643,215 A | 7/1997 | Fuhrman et al. |
| 5,653,696 A | 8/1997 | Shiber |
| 5,662,643 A | 9/1997 | Kung et al. |
| 5,676,526 A | 10/1997 | Kuwana et al. |
| 5,683,231 A | 11/1997 | Nakazawa et al. |
| 5,702,365 A | 12/1997 | King |

(56) References Cited

U.S. PATENT DOCUMENTS

| | | | |
|---|---|---|---|
| 5,713,730 A | 2/1998 | Nose et al. |
| 5,735,892 A | 4/1998 | Myers et al. |
| 5,749,839 A | 5/1998 | Kovacs |
| 5,749,855 A | 5/1998 | Reitan |
| 5,751,125 A | 5/1998 | Weiss |
| 5,759,148 A | 6/1998 | Sipin |
| 5,766,207 A | 6/1998 | Potter et al. |
| 5,776,096 A | 7/1998 | Fields |
| 5,800,138 A | 9/1998 | Merce Vives |
| 5,800,457 A | 9/1998 | Gelbfish |
| 5,803,720 A | 9/1998 | Ohara et al. |
| 5,814,076 A | 9/1998 | Brownlee |
| 5,814,102 A | 9/1998 | Guldner et al. |
| 5,851,174 A | 12/1998 | Jarvik et al. |
| 5,888,241 A | 3/1999 | Jarvik |
| 5,906,579 A | 5/1999 | Vander Salm et al. |
| 5,910,124 A | 6/1999 | Rubin |
| 5,919,369 A | 7/1999 | Ash |
| 5,941,813 A | 8/1999 | Sievers et al. |
| 5,957,672 A | 9/1999 | Aber |
| 5,964,694 A | 10/1999 | Siess et al. |
| 5,984,893 A | 11/1999 | Ward |
| 6,007,478 A | 12/1999 | Siess et al. |
| 6,013,058 A | 1/2000 | Prosl et al. |
| 6,022,363 A | 2/2000 | Walker et al. |
| 6,030,336 A | 2/2000 | Franchi |
| 6,042,347 A | 3/2000 | Scholl et al. |
| 6,053,943 A | 4/2000 | Edwin et al. |
| 6,066,085 A | 5/2000 | Heilman et al. |
| 6,066,152 A | 5/2000 | Strauss et al. |
| 6,068,588 A | 5/2000 | Goldowsky |
| 6,071,093 A | 6/2000 | Hart |
| 6,071,258 A | 6/2000 | Dalke et al. |
| 6,082,105 A | 7/2000 | Miyata |
| 6,101,406 A | 8/2000 | Hacker et al. |
| 6,106,509 A | 8/2000 | Loubser |
| 6,113,536 A | 9/2000 | Aboul Hosn et al. |
| 6,117,130 A | 9/2000 | Kung |
| 6,117,390 A | 9/2000 | Corey |
| 6,120,537 A | 9/2000 | Wampler |
| 6,123,659 A | 9/2000 | Le Blanc et al. |
| 6,123,726 A | 9/2000 | Mori et al. |
| 6,129,660 A | 10/2000 | Nakazeki et al. |
| 6,136,025 A | 10/2000 | Barbut et al. |
| 6,139,487 A | 10/2000 | Siess |
| 6,142,752 A | 11/2000 | Akamatsu et al. |
| 6,146,771 A | 11/2000 | Wirt et al. |
| 6,149,683 A | 11/2000 | Lancisi et al. |
| 6,152,704 A | 11/2000 | Aboul Hosn et al. |
| 6,155,969 A | 12/2000 | Schima et al. |
| 6,176,848 B1 | 1/2001 | Rau et al. |
| 6,180,058 B1 | 1/2001 | Lindsay |
| 6,197,055 B1 | 3/2001 | Matthews |
| 6,197,289 B1 | 3/2001 | Wirt et al. |
| 6,210,133 B1 | 4/2001 | Aboul Hosn et al. |
| 6,210,318 B1 | 4/2001 | Lederman |
| 6,228,023 B1 | 5/2001 | Zaslavsky et al. |
| 6,236,883 B1 | 5/2001 | Ciaccio et al. |
| 6,254,359 B1 | 7/2001 | Aber |
| 6,270,831 B2 | 8/2001 | Kumar et al. |
| 6,273,861 B1 | 8/2001 | Bates et al. |
| 6,283,949 B1 | 9/2001 | Roorda |
| 6,287,319 B1 | 9/2001 | Aboul Hosn et al. |
| 6,290,685 B1 | 9/2001 | Insley et al. |
| 6,312,462 B1 | 11/2001 | McDermott et al. |
| 6,314,322 B1 | 11/2001 | Rosenberg |
| 6,319,231 B1 | 11/2001 | Andrulitis |
| 6,361,292 B1 | 3/2002 | Chang et al. |
| 6,361,501 B1 | 3/2002 | Amano et al. |
| 6,364,833 B1 | 4/2002 | Valerio et al. |
| 6,398,715 B1 | 6/2002 | Magovern et al. |
| 6,400,991 B1 | 6/2002 | Kung |
| 6,406,267 B1 | 6/2002 | Mondiere |
| 6,406,422 B1 | 6/2002 | Landesberg |
| 6,419,657 B1 | 7/2002 | Pacetti |
| 6,422,990 B1 | 7/2002 | Prem |
| 6,432,136 B1 | 8/2002 | Weiss et al. |
| 6,443,944 B1 | 9/2002 | Doshi et al. |
| 6,443,983 B1 | 9/2002 | Nagyszalanczy et al. |
| 6,445,956 B1 | 9/2002 | Laird et al. |
| 6,447,265 B1 | 9/2002 | Antaki et al. |
| 6,447,266 B2 | 9/2002 | Antaki et al. |
| 6,447,441 B1 | 9/2002 | Yu et al. |
| 6,497,680 B1 | 12/2002 | Holst et al. |
| 6,503,224 B1 | 1/2003 | Forman et al. |
| 6,503,450 B1 | 1/2003 | Afzal et al. |
| 6,508,787 B2 | 1/2003 | Erbel et al. |
| 6,508,806 B1 | 1/2003 | Hoste |
| 6,527,699 B1 | 3/2003 | Goldowsky |
| 6,533,716 B1 | 3/2003 | Schmitz-Rode et al. |
| 6,533,724 B2 | 3/2003 | McNair |
| 6,537,315 B2 | 3/2003 | Yamazaki et al. |
| 6,540,658 B1 | 4/2003 | Fasciano et al. |
| 6,540,659 B1 | 4/2003 | Milbocker |
| 6,544,543 B1 | 4/2003 | Mandrusov et al. |
| 6,547,716 B1 | 4/2003 | Milbocker |
| 6,562,022 B2 | 5/2003 | Hoste et al. |
| 6,572,529 B2 | 6/2003 | Wilk |
| 6,572,534 B1 | 6/2003 | Milbocker et al. |
| 6,595,943 B1 | 7/2003 | Burbank |
| 6,602,182 B1 | 8/2003 | Milbocker |
| 6,616,596 B1 | 9/2003 | Milbocker |
| 6,620,120 B2 | 9/2003 | Landry et al. |
| 6,623,420 B2 | 9/2003 | Reich et al. |
| 6,626,821 B1 | 9/2003 | Kung et al. |
| 6,626,889 B1 | 9/2003 | Simpson et al. |
| 6,626,935 B1 | 9/2003 | Ainsworth et al. |
| 6,632,215 B1 | 10/2003 | Lemelson |
| 6,635,083 B1 | 10/2003 | Cheng et al. |
| 6,656,220 B1 | 12/2003 | Gomez et al. |
| 6,669,624 B2 | 12/2003 | Frazier |
| 6,669,662 B1 | 12/2003 | Webler |
| 6,676,679 B1 | 1/2004 | Mueller et al. |
| 6,685,696 B2 | 2/2004 | Fleischhacker et al. |
| 6,688,869 B1 | 2/2004 | Simonds |
| 6,699,231 B1 | 3/2004 | Sterman et al. |
| 6,709,382 B1 | 3/2004 | Homer |
| 6,712,844 B2 | 3/2004 | Pacetti |
| 6,730,102 B1 | 5/2004 | Burdulis et al. |
| 6,746,416 B2 | 6/2004 | Hubbard et al. |
| 6,749,615 B2 | 6/2004 | Burdulis et al. |
| 6,769,871 B2 | 8/2004 | Yamazaki |
| 6,790,171 B1 | 9/2004 | Gründeman et al. |
| 6,811,749 B2 | 11/2004 | Lindsay |
| 6,821,295 B1 | 11/2004 | Farrar |
| 6,837,890 B1 | 1/2005 | Chludzinski et al. |
| 6,846,296 B1 | 1/2005 | Milbocker et al. |
| 6,866,650 B2 | 3/2005 | Stevens et al. |
| 6,879,126 B2 | 4/2005 | Paden et al. |
| 6,884,210 B2 | 4/2005 | Nose et al. |
| 6,908,280 B2 | 6/2005 | Yamazaki |
| 6,908,435 B1 | 6/2005 | Mueller et al. |
| 6,929,632 B2 | 8/2005 | Nita et al. |
| 6,929,660 B1 | 8/2005 | Ainsworth et al. |
| 6,942,672 B2 | 9/2005 | Heilman et al. |
| 6,945,978 B1 | 9/2005 | Hyde |
| 6,949,066 B2 | 9/2005 | Beamson et al. |
| 6,969,345 B2 | 11/2005 | Jassawalla et al. |
| 6,981,942 B2 | 1/2006 | Khaw et al. |
| 7,022,100 B1 | 4/2006 | Aboul Hosn et al. |
| 7,025,742 B2 | 4/2006 | Rubenstein et al. |
| 7,027,875 B2 | 4/2006 | Siess et al. |
| 7,029,483 B2 | 4/2006 | Schwartz |
| 7,037,253 B2 | 5/2006 | French et al. |
| 7,048,747 B2 | 5/2006 | Arcia et al. |
| 7,074,018 B2 | 7/2006 | Chang |
| 7,108,652 B2 | 9/2006 | Stenberg et al. |
| 7,118,525 B2 | 10/2006 | Coleman et al. |
| 7,122,151 B2 | 10/2006 | Reeder et al. |
| 7,125,376 B2 | 10/2006 | Viole et al. |
| 7,126,310 B1 | 10/2006 | Barron |
| 7,150,711 B2 | 12/2006 | Nüsser et al. |
| 7,155,291 B2 | 12/2006 | Zarinetchi et al. |
| 7,172,551 B2 | 2/2007 | Leasure |

(56)                    References Cited

U.S. PATENT DOCUMENTS

| | | | |
|---|---|---|---|
| 7,189,260 B2 | 3/2007 | Horvath et al. |
| 7,220,275 B2 | 5/2007 | Davidson et al. |
| 7,229,258 B2 | 6/2007 | Wood et al. |
| 7,229,402 B2 | 6/2007 | Diaz et al. |
| 7,238,151 B2 | 7/2007 | Frazier |
| 7,244,224 B2 | 7/2007 | Tsukahara et al. |
| 7,247,166 B2 | 7/2007 | Pienknagura |
| 7,303,581 B2 | 12/2007 | Peralta |
| 7,331,972 B1 | 2/2008 | Cox |
| 7,331,987 B1 | 2/2008 | Cox |
| 7,361,726 B2 | 4/2008 | Pacetti et al. |
| 7,377,927 B2 | 5/2008 | Burdulis et al. |
| 7,392,077 B2 | 6/2008 | Mueller et al. |
| 7,393,181 B2 | 7/2008 | McBride et al. |
| 7,396,327 B2 | 7/2008 | Morello |
| 7,479,102 B2 | 1/2009 | Jarvik |
| 7,520,850 B2 | 4/2009 | Brockway |
| 7,524,277 B1 | 4/2009 | Wang et al. |
| 7,541,000 B2 | 6/2009 | Stringer et al. |
| 7,544,160 B2 | 6/2009 | Gross |
| 7,547,391 B2 | 6/2009 | Petrie |
| 7,585,322 B2 | 9/2009 | Azzolina |
| 7,588,530 B2 | 9/2009 | Heilman et al. |
| 7,588,549 B2 | 9/2009 | Eccleston |
| 7,591,199 B2 | 9/2009 | Weldon et al. |
| 7,611,478 B2 | 11/2009 | Lucke et al. |
| 7,628,756 B2 | 12/2009 | Hacker et al. |
| 7,713,259 B2 | 5/2010 | Gosiengfiao et al. |
| RE41,394 E | 6/2010 | Bugge et al. |
| 7,731,664 B1 | 6/2010 | Millar |
| 7,736,296 B2 | 6/2010 | Siess et al. |
| 7,736,375 B2 | 6/2010 | Crow |
| 7,758,492 B2 | 7/2010 | Weatherbee |
| 7,776,991 B2 | 8/2010 | Pacetti et al. |
| 7,780,628 B1 | 8/2010 | Keren et al. |
| 7,794,419 B2 | 9/2010 | Paolini et al. |
| 7,794,743 B2 | 9/2010 | Simhambhatla et al. |
| 7,819,834 B2 | 10/2010 | Paul |
| 7,828,710 B2 | 11/2010 | Shifflette |
| 7,833,239 B2 | 11/2010 | Nash |
| 7,841,976 B2 | 11/2010 | McBride et al. |
| 7,850,594 B2 | 12/2010 | Sutton et al. |
| 7,862,501 B2 | 1/2011 | Woodard |
| 7,878,967 B1 | 2/2011 | Khanal |
| 7,914,436 B1 | 3/2011 | Kung |
| 7,922,657 B2 | 4/2011 | Gillinov et al. |
| 7,942,804 B2 | 5/2011 | Khaw |
| 7,963,905 B2 | 6/2011 | Salmonsen et al. |
| 7,972,122 B2 | 7/2011 | LaRose et al. |
| 7,972,291 B2 | 7/2011 | Ibragimov |
| 7,985,442 B2 | 7/2011 | Gong |
| 7,988,728 B2 | 8/2011 | Ayre |
| 7,993,259 B2 | 8/2011 | Kang et al. |
| 7,993,260 B2 | 8/2011 | Bolling |
| 7,993,358 B2 | 8/2011 | O'Brien |
| 7,998,054 B2 | 8/2011 | Bolling |
| 7,998,190 B2 | 8/2011 | Gharib et al. |
| 8,012,079 B2 | 9/2011 | Delgado |
| 8,012,194 B2 | 9/2011 | Edwin et al. |
| 8,012,508 B2 | 9/2011 | Ludwig |
| 8,029,728 B2 | 10/2011 | Lindsay |
| 8,034,098 B1 | 10/2011 | Callas et al. |
| 8,048,442 B1 | 11/2011 | Hossainy et al. |
| 8,052,749 B2 | 11/2011 | Salahieh et al. |
| 8,070,742 B2 | 12/2011 | Woo |
| 8,070,804 B2 | 12/2011 | Hyde et al. |
| 8,075,472 B2 | 12/2011 | Zilbershlag et al. |
| 8,079,948 B2 | 12/2011 | Shifflette |
| 8,083,726 B1 | 12/2011 | Wang |
| 8,123,669 B2 | 2/2012 | Siess et al. |
| 8,123,674 B2 | 2/2012 | Kuyava |
| 8,133,272 B2 | 3/2012 | Hyde |
| RE43,299 E | 4/2012 | Siess |
| 8,152,035 B2 | 4/2012 | Eart |
| 8,152,845 B2 | 4/2012 | Bourque |
| 8,153,083 B2 | 4/2012 | Briggs |
| 8,157,719 B1 | 4/2012 | Ainsworth et al. |
| 8,157,721 B2 | 4/2012 | Sugiura |
| 8,157,758 B2 | 4/2012 | Pecor et al. |
| 8,158,062 B2 | 4/2012 | Dykes et al. |
| 8,162,021 B2 | 4/2012 | Tomasetti et al. |
| 8,167,589 B2 | 5/2012 | Hidaka et al. |
| 8,172,783 B1 | 5/2012 | Ray |
| 8,177,750 B2 | 5/2012 | Steinbach et al. |
| 8,187,324 B2 | 5/2012 | Webler et al. |
| 8,197,463 B2 | 6/2012 | Intoccia |
| 8,210,829 B2 | 7/2012 | Horvath et al. |
| 8,241,199 B2 | 8/2012 | Maschke |
| 8,257,258 B2 | 9/2012 | Zocchi |
| 8,257,375 B2 | 9/2012 | Maschke |
| 8,266,943 B2 | 9/2012 | Miyakoshi et al. |
| D669,585 S | 10/2012 | Bourque |
| 8,277,476 B2 | 10/2012 | Taylor et al. |
| 8,282,359 B2 | 10/2012 | Ayre et al. |
| 8,292,908 B2 | 10/2012 | Nieman et al. |
| D671,646 S | 11/2012 | Bourque et al. |
| 8,303,482 B2 | 11/2012 | Schima et al. |
| 8,323,173 B2 | 12/2012 | Benkowski et al. |
| 8,323,203 B2 | 12/2012 | Thornton |
| 8,328,750 B2 | 12/2012 | Peters et al. |
| 8,329,114 B2 | 12/2012 | Temple |
| 8,329,158 B2 | 12/2012 | Hossainy et al. |
| 8,366,599 B2 | 2/2013 | Tansley et al. |
| 8,372,137 B2 | 2/2013 | Pienknagura |
| 8,377,033 B2 | 2/2013 | Basu et al. |
| 8,377,083 B2 | 2/2013 | Mauch et al. |
| 8,382,695 B1 | 2/2013 | Patel |
| 8,388,565 B2 | 3/2013 | Shifflette |
| 8,388,649 B2 | 3/2013 | Woodard et al. |
| 8,419,609 B2 | 4/2013 | Shambaugh et al. |
| 8,419,944 B2 | 4/2013 | Alkanhal |
| 8,439,909 B2 | 5/2013 | Wang et al. |
| 8,449,444 B2 | 5/2013 | Poirier |
| 8,454,683 B2 | 6/2013 | Rafiee et al. |
| 8,485,961 B2 | 7/2013 | Campbell et al. |
| 8,496,874 B2 | 7/2013 | Gellman et al. |
| 8,500,620 B2 | 8/2013 | Lu et al. |
| 8,506,471 B2 | 8/2013 | Bourque |
| 8,535,211 B2 | 9/2013 | Campbell et al. |
| 8,535,212 B2 | 9/2013 | Robert |
| 8,538,515 B2 | 9/2013 | Atanasoska et al. |
| 8,545,382 B2 | 10/2013 | Suzuki et al. |
| 8,545,447 B2 | 10/2013 | Demarais et al. |
| 8,562,509 B2 | 10/2013 | Bates |
| 8,568,289 B2 | 10/2013 | Mazur |
| 8,579,858 B2 | 11/2013 | Reitan et al. |
| 8,579,967 B2 | 11/2013 | Webler et al. |
| 8,585,572 B2 | 11/2013 | Mehmanesh |
| 8,586,527 B2 | 11/2013 | Singh |
| 8,591,393 B2 | 11/2013 | Walters et al. |
| 8,591,394 B2 | 11/2013 | Peters et al. |
| 8,591,449 B2 | 11/2013 | Hudson |
| 8,591,538 B2 | 11/2013 | Gellman |
| 8,591,539 B2 | 11/2013 | Gellman |
| D696,769 S | 12/2013 | Schenck et al. |
| 8,597,170 B2 | 12/2013 | Walters et al. |
| 8,608,661 B1 | 12/2013 | Mandrusov et al. |
| 8,613,777 B2 | 12/2013 | Siess et al. |
| 8,613,892 B2 | 12/2013 | Stafford |
| 8,617,239 B2 | 12/2013 | Reitan |
| 8,631,680 B2 | 1/2014 | Fleischli et al. |
| 8,632,449 B2 | 1/2014 | Masuzawa et al. |
| 8,641,594 B2 | 2/2014 | LaRose et al. |
| 8,657,871 B2 | 2/2014 | Limon |
| 8,657,875 B2 | 2/2014 | Kung et al. |
| 8,668,473 B2 | 3/2014 | LaRose et al. |
| 8,684,903 B2 | 4/2014 | Nour |
| 8,690,749 B1 | 4/2014 | Nunez |
| 8,690,823 B2 | 4/2014 | Yribarren et al. |
| 8,697,058 B2 | 4/2014 | Basu et al. |
| 8,708,948 B2 | 4/2014 | Consigny et al. |
| 8,715,151 B2 | 5/2014 | Poirier |
| 8,715,156 B2 | 5/2014 | Jayaraman |
| 8,715,707 B2 | 5/2014 | Hossainy et al. |

(56)                    References Cited

U.S. PATENT DOCUMENTS

| | | | |
|---|---|---|---|
| 8,721,516 B2 | 5/2014 | Scheckel |
| 8,721,517 B2 | 5/2014 | Zeng et al. |
| 8,734,331 B2 | 5/2014 | Evans et al. |
| 8,734,508 B2 | 5/2014 | Hastings et al. |
| 8,739,727 B2 | 6/2014 | Austin et al. |
| 8,740,920 B2 | 6/2014 | Goldfarb et al. |
| 8,741,287 B2 | 6/2014 | Brophy et al. |
| 8,758,388 B2 | 6/2014 | Pah |
| 8,766,788 B2 | 7/2014 | D'Ambrosio |
| 8,777,832 B1 | 7/2014 | Wang et al. |
| 8,790,399 B2 | 7/2014 | Frazier et al. |
| 8,795,576 B2 | 8/2014 | Tao et al. |
| 8,814,543 B2 | 8/2014 | Liebing |
| 8,814,776 B2 | 8/2014 | Hastie et al. |
| 8,814,933 B2 | 8/2014 | Siess |
| 8,815,274 B2 | 8/2014 | DesNoyer et al. |
| 8,821,366 B2 | 9/2014 | Farnan et al. |
| 8,837,096 B2 | 9/2014 | Seebruch |
| 8,840,539 B2 | 9/2014 | Zilbershlag |
| 8,840,566 B2 | 9/2014 | Seibel et al. |
| 8,849,398 B2 | 9/2014 | Evans |
| 8,862,232 B2 | 10/2014 | Zarinetchi et al. |
| 8,864,642 B2 | 10/2014 | Scheckel |
| 8,876,685 B2 | 11/2014 | Crosby et al. |
| 8,882,744 B2 | 11/2014 | Dormanen et al. |
| 8,888,675 B2 | 11/2014 | Stankus et al. |
| 8,894,387 B2 | 11/2014 | White |
| 8,894,561 B2 | 11/2014 | Callaway et al. |
| 8,897,873 B2 | 11/2014 | Schima et al. |
| 8,900,060 B2 | 12/2014 | Liebing |
| 8,905,910 B2 | 12/2014 | Reichenbach et al. |
| 8,927,700 B2 | 1/2015 | McCauley et al. |
| 8,932,141 B2 | 1/2015 | Liebing |
| 8,932,197 B2 | 1/2015 | Gregoric et al. |
| 8,934,956 B2 | 1/2015 | Glenn et al. |
| 8,942,828 B1 | 1/2015 | Schecter |
| 8,944,748 B2 | 2/2015 | Liebing |
| 8,945,159 B2 | 2/2015 | Nussbaum |
| 8,956,402 B2 | 2/2015 | Cohn |
| 8,961,387 B2 | 2/2015 | Duncan |
| 8,961,466 B2 | 2/2015 | Steinbach |
| 8,971,980 B2 | 3/2015 | Mace et al. |
| 8,974,519 B2 | 3/2015 | Gennrich et al. |
| 8,992,406 B2 | 3/2015 | Corbett |
| 8,997,349 B2 | 4/2015 | Mori et al. |
| 9,002,468 B2 | 4/2015 | Shea et al. |
| 9,023,010 B2 | 5/2015 | Chiu et al. |
| 9,028,216 B2 | 5/2015 | Schumacher et al. |
| 9,028,392 B2 | 5/2015 | Shifflette |
| 9,028,859 B2 | 5/2015 | Hossainy et al. |
| 9,033,863 B2 | 5/2015 | Jarvik |
| 9,033,909 B2 | 5/2015 | Aihara |
| 9,039,595 B2 | 5/2015 | Ayre et al. |
| 9,044,236 B2 | 6/2015 | Nguyen et al. |
| 9,056,159 B2 | 6/2015 | Medvedev et al. |
| 9,066,992 B2 | 6/2015 | Stankus et al. |
| 9,067,005 B2 | 6/2015 | Ozaki et al. |
| 9,067,006 B2 | 6/2015 | Toellner |
| 9,072,825 B2 | 7/2015 | Pfeffer et al. |
| 9,078,692 B2 | 7/2015 | Shturman et al. |
| 9,089,329 B2 | 7/2015 | Hoarau et al. |
| 9,089,634 B2 | 7/2015 | Schumacher et al. |
| 9,089,635 B2 | 7/2015 | Reichenbach et al. |
| 9,089,670 B2 | 7/2015 | Scheckel |
| 9,095,428 B2 | 8/2015 | Kabir et al. |
| 9,096,703 B2 | 8/2015 | Li et al. |
| 9,101,302 B2 | 8/2015 | Mace et al. |
| 9,125,977 B2 | 9/2015 | Nishimura et al. |
| 9,127,680 B2 | 9/2015 | Yanai et al. |
| 9,138,516 B2 | 9/2015 | Vischer et al. |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,168,361 B2 | 10/2015 | Ehrenreich et al. |
| 9,180,227 B2 | 11/2015 | Ludwig et al. |
| 9,180,235 B2 | 11/2015 | Forsell |
| 9,192,705 B2 | 11/2015 | Yanai et al. |
| 9,199,020 B2 | 12/2015 | Siess |
| 9,217,442 B2 | 12/2015 | Wiessler et al. |
| D746,975 S | 1/2016 | Schenck et al. |
| 9,227,002 B1 | 1/2016 | Giridharan et al. |
| 9,239,049 B2 | 1/2016 | Jarnagin et al. |
| 9,265,870 B2 | 2/2016 | Reichenbach et al. |
| 9,278,189 B2 | 3/2016 | Corbett |
| 9,283,314 B2 | 3/2016 | Prasad et al. |
| 9,291,591 B2 | 3/2016 | Simmons et al. |
| 9,295,550 B2 | 3/2016 | Nguyen et al. |
| 9,295,767 B2 | 3/2016 | Schmid et al. |
| 9,308,302 B2 | 4/2016 | Zeng |
| 9,308,304 B2 | 4/2016 | Peters et al. |
| 9,314,558 B2 | 4/2016 | Er |
| 9,314,559 B2 | 4/2016 | Smith et al. |
| 9,328,741 B2 | 5/2016 | Liebing |
| 9,333,284 B2 | 5/2016 | Thompson et al. |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,255 B2 | 6/2016 | Weber |
| 9,364,592 B2 | 6/2016 | McBride et al. |
| 9,370,613 B2 | 6/2016 | Hsu et al. |
| 9,375,445 B2 | 6/2016 | Hossainy et al. |
| 9,381,285 B2 | 7/2016 | Ozaki et al. |
| 9,387,284 B2 | 7/2016 | Heilman et al. |
| 9,409,012 B2 | 8/2016 | Eidenschink et al. |
| 9,416,783 B2 | 8/2016 | Schumacher et al. |
| 9,416,791 B2 | 8/2016 | Toellner |
| 9,421,311 B2 | 8/2016 | Tanner et al. |
| 9,433,713 B2 | 9/2016 | Corbett et al. |
| 9,435,450 B2 | 9/2016 | Muennich |
| 9,446,179 B2 | 9/2016 | Keenan et al. |
| 9,452,249 B2 | 9/2016 | Kearsley et al. |
| 9,474,840 B2 | 10/2016 | Siess |
| 9,486,565 B2 | 11/2016 | Göllner et al. |
| 9,492,601 B2 | 11/2016 | Casas et al. |
| 9,504,491 B2 | 11/2016 | Callas et al. |
| 9,511,179 B2 | 12/2016 | Casas et al. |
| 9,512,839 B2 | 12/2016 | Liebing |
| 9,522,257 B2 | 12/2016 | Webler |
| 9,526,818 B2 | 12/2016 | Kearsley et al. |
| 9,533,084 B2 | 1/2017 | Siess et al. |
| 9,533,085 B2 | 1/2017 | Hanna |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,555,177 B2 | 1/2017 | Curtis et al. |
| 9,556,873 B2 | 1/2017 | Yanai et al. |
| 9,561,309 B2 | 2/2017 | Glauser et al. |
| 9,561,313 B2 | 2/2017 | Taskin |
| 9,592,328 B2 | 3/2017 | Jeevanandam et al. |
| 9,603,983 B2 | 3/2017 | Roehn et al. |
| 9,603,984 B2 | 3/2017 | Romero et al. |
| 9,611,743 B2 | 4/2017 | Toellner et al. |
| 9,612,182 B2 | 4/2017 | Olde et al. |
| 9,616,157 B2 | 4/2017 | Akdis |
| 9,616,159 B2 | 4/2017 | Anderson et al. |
| 9,623,163 B1 | 4/2017 | Fischi |
| 9,631,754 B2 | 4/2017 | Richardson et al. |
| 9,642,984 B2 | 5/2017 | Schumacher et al. |
| 9,656,010 B2 | 5/2017 | Burke |
| 9,656,030 B1 | 5/2017 | Webler et al. |
| 9,662,211 B2 | 5/2017 | Hodson et al. |
| 9,669,141 B2 | 6/2017 | Parker et al. |
| 9,669,142 B2 | 6/2017 | Spanier et al. |
| 9,669,143 B2 | 6/2017 | Guerrero |
| 9,675,450 B2 | 6/2017 | Straka et al. |
| 9,675,738 B2 | 6/2017 | Tanner et al. |
| 9,675,739 B2 | 6/2017 | Tanner et al. |
| 9,675,742 B2 | 6/2017 | Casas et al. |
| 9,687,596 B2 | 6/2017 | Poirier |
| 9,687,630 B2 | 6/2017 | Basu et al. |
| 9,700,659 B2 | 7/2017 | Kantrowitz et al. |
| 9,713,662 B2 | 7/2017 | Rosenberg et al. |

(56)                    References Cited

U.S. PATENT DOCUMENTS

| | | | |
|---|---|---|---|
| 9,713,663 B2 | 7/2017 | Medvedev et al. |
| 9,715,839 B2 | 7/2017 | Pybus et al. |
| 9,717,615 B2 | 8/2017 | Grandt |
| 9,717,832 B2 | 8/2017 | Taskin et al. |
| 9,717,839 B2 | 8/2017 | Hashimoto |
| 9,726,195 B2 | 8/2017 | Cecere et al. |
| 9,731,058 B2 | 8/2017 | Siebenhaar et al. |
| 9,731,101 B2 | 8/2017 | Bertrand et al. |
| 9,737,361 B2 | 8/2017 | Magana et al. |
| 9,737,651 B2 | 8/2017 | Wampler |
| 9,744,280 B2 | 8/2017 | Schade et al. |
| 9,744,287 B2 | 8/2017 | Bulent et al. |
| 9,750,859 B2 | 9/2017 | Bulent et al. |
| 9,757,502 B2 | 9/2017 | Burke et al. |
| 9,770,202 B2 | 9/2017 | Ralston et al. |
| 9,770,543 B2 | 9/2017 | Tanner et al. |
| 9,771,801 B2 | 9/2017 | Schumacher et al. |
| 9,775,930 B2 | 10/2017 | Michal et al. |
| 9,782,279 B2 | 10/2017 | Kassab |
| 9,782,527 B2 | 10/2017 | Thomas et al. |
| 9,795,780 B2 | 10/2017 | Serna et al. |
| 9,801,987 B2 | 10/2017 | Faman et al. |
| 9,801,992 B2 | 10/2017 | Giordano et al. |
| 9,821,098 B2 | 11/2017 | Horvath et al. |
| 9,821,146 B2 | 11/2017 | Tao et al. |
| 9,827,356 B2 | 11/2017 | Muller et al. |
| 9,833,314 B2 | 12/2017 | Corbett |
| 9,833,550 B2 | 12/2017 | Siess |
| 9,833,551 B2 | 12/2017 | Criscione et al. |
| 9,839,734 B1 | 12/2017 | Menon et al. |
| 9,844,618 B2 | 12/2017 | Muller-Spanka et al. |
| 9,850,906 B2 | 12/2017 | Ozaki et al. |
| 9,855,437 B2 | 1/2018 | Nguyen et al. |
| 9,861,504 B2 | 1/2018 | Abunassar et al. |
| 9,861,731 B2 | 1/2018 | Tamburino |
| 9,872,948 B2 | 1/2018 | Siess |
| 9,878,087 B2 | 1/2018 | Richardson et al. |
| 9,878,169 B2 | 1/2018 | Hossainy |
| 9,889,242 B2 | 2/2018 | Pfeffer et al. |
| 9,895,244 B2 | 2/2018 | Papp et al. |
| 9,895,475 B2 | 2/2018 | Toellner et al. |
| 9,907,890 B2 | 3/2018 | Muller |
| 9,907,892 B2 | 3/2018 | Broen et al. |
| 9,913,937 B2 | 3/2018 | Schwammenthal et al. |
| 9,918,822 B2 | 3/2018 | Abunassar et al. |
| 9,919,085 B2 | 3/2018 | Throckmorton et al. |
| 9,919,088 B2 | 3/2018 | Bonde et al. |
| 9,919,089 B2 | 3/2018 | Garrigue |
| 9,950,101 B2 | 4/2018 | Smith et al. |
| 9,956,410 B2 | 5/2018 | Deem et al. |
| 9,962,258 B2 | 5/2018 | Seguin et al. |
| 9,974,893 B2 | 5/2018 | Toellner |
| 9,974,894 B2 | 5/2018 | Morello |
| 9,981,078 B2 | 5/2018 | Jin et al. |
| 9,985,374 B2 | 5/2018 | Hodges |
| 9,987,407 B2 | 6/2018 | Grant et al. |
| 10,010,273 B2 | 7/2018 | Sloan et al. |
| 10,022,499 B2 | 7/2018 | Galasso |
| 10,028,835 B2 | 7/2018 | Kermode et al. |
| 10,029,037 B2 | 7/2018 | Muller et al. |
| 10,029,038 B2 | 7/2018 | Hodges |
| 10,029,039 B2 | 7/2018 | Dague et al. |
| 10,031,124 B2 | 7/2018 | Galasso |
| 10,034,972 B2 | 7/2018 | Wampler et al. |
| 10,039,873 B2 | 8/2018 | Siegenthaler |
| 10,046,146 B2 | 8/2018 | Manderfeld et al. |
| 10,052,419 B2 | 8/2018 | Er |
| 10,058,349 B2 | 8/2018 | Gunderson et al. |
| 10,058,641 B2 | 8/2018 | Mollison et al. |
| 10,058,652 B2 | 8/2018 | Tsoukalis |
| 10,058,653 B2 | 8/2018 | Wang et al. |
| 10,077,777 B2 | 9/2018 | Horvath et al. |
| 10,080,828 B2 | 9/2018 | Wiesener et al. |
| 10,080,834 B2 | 9/2018 | Federspiel et al. |
| 10,080,871 B2 | 9/2018 | Schumacher et al. |

| | | | |
|---|---|---|---|
| 10,208,763 B2 | 2/2019 | Schumacher et al. |
| 10,357,598 B2 | 7/2019 | Aboul-Hosn et al. |
| 10,569,005 B2 | 2/2020 | Solem et al. |
| 10,722,631 B2 | 7/2020 | Salahieh et al. |
| 10,881,770 B2 | 1/2021 | Tuval et al. |
| 10,894,115 B2 | 1/2021 | Pfeffer et al. |
| 11,123,538 B2 | 9/2021 | Epple et al. |
| 11,185,677 B2 | 11/2021 | Salahieh et al. |
| 11,229,784 B2 | 1/2022 | Salahieh et al. |
| 11,268,521 B2 | 3/2022 | Toellner |
| 11,280,345 B2 | 3/2022 | Bredenbreuker et al. |
| 11,850,413 B2 | 12/2023 | Zeng et al. |
| 12,017,056 B2 | 6/2024 | Guo et al. |
| 2001/0003802 A1 | 6/2001 | Vitale |
| 2001/0023369 A1 | 9/2001 | Chobotov |
| 2001/0046380 A1 | 11/2001 | LeFebvre |
| 2001/0053928 A1 | 12/2001 | Edelman et al. |
| 2002/0057989 A1 | 5/2002 | Afzal et al. |
| 2002/0058971 A1 | 5/2002 | Zarinetchi et al. |
| 2002/0068848 A1 | 6/2002 | Zadini et al. |
| 2002/0072679 A1 | 6/2002 | Schock et al. |
| 2002/0072779 A1 | 6/2002 | Loeb |
| 2002/0128709 A1 | 9/2002 | Pless |
| 2002/0147495 A1 | 10/2002 | Petroff |
| 2003/0069465 A1 | 4/2003 | Benkowski et al. |
| 2003/0088151 A1 | 5/2003 | Kung et al. |
| 2003/0131995 A1 | 7/2003 | de Rouffignac et al. |
| 2003/0155111 A1 | 8/2003 | Vinegar et al. |
| 2003/0173081 A1 | 9/2003 | Vinegar et al. |
| 2003/0173082 A1 | 9/2003 | Vinegar et al. |
| 2003/0173085 A1 | 9/2003 | Vinegar et al. |
| 2003/0178191 A1 | 9/2003 | Maher et al. |
| 2003/0209348 A1 | 11/2003 | Ward et al. |
| 2003/0217957 A1 | 11/2003 | Bowman et al. |
| 2003/0236493 A1* | 12/2003 | Mauch .............. A61M 25/0147 |
| | | | 604/95.04 |
| 2004/0024285 A1 | 2/2004 | Muckter |
| 2004/0040715 A1 | 3/2004 | Wellington et al. |
| 2004/0047753 A1* | 3/2004 | Horvath ............. A61M 60/232 |
| | | | 417/423.12 |
| 2004/0097782 A1 | 5/2004 | Korakianitis et al. |
| 2004/0097783 A1 | 5/2004 | Peters et al. |
| 2004/0228724 A1 | 11/2004 | Capone et al. |
| 2004/0249363 A1 | 12/2004 | Burke et al. |
| 2005/0010077 A1 | 1/2005 | Calderon |
| 2005/0043805 A1 | 2/2005 | Chudik |
| 2005/0049696 A1 | 3/2005 | Siess et al. |
| 2005/0060036 A1 | 3/2005 | Schultz et al. |
| 2005/0113632 A1 | 5/2005 | Ortiz et al. |
| 2005/0119599 A1 | 6/2005 | Kanz et al. |
| 2005/0187616 A1 | 8/2005 | Realyvasquez |
| 2005/0209617 A1 | 9/2005 | Koven et al. |
| 2005/0220636 A1 | 10/2005 | Henein et al. |
| 2005/0246010 A1 | 11/2005 | Alexander et al. |
| 2005/0254976 A1 | 11/2005 | Carrier et al. |
| 2005/0256540 A1 | 11/2005 | Silver et al. |
| 2005/0277803 A1 | 12/2005 | Pecor |
| 2006/0111641 A1 | 5/2006 | Manera et al. |
| 2006/0116700 A1 | 6/2006 | Crow |
| 2006/0129082 A1 | 6/2006 | Rozga |
| 2006/0155158 A1 | 7/2006 | Aboul Hosn |
| 2006/0177343 A1 | 8/2006 | Brian et al. |
| 2006/0195098 A1 | 8/2006 | Schumacher |
| 2006/0257355 A1 | 11/2006 | Stewart et al. |
| 2006/0293664 A1 | 12/2006 | Schumacher |
| 2007/0106274 A1 | 5/2007 | Ayre et al. |
| 2007/0167091 A1 | 7/2007 | Schumacher |
| 2007/0203453 A1 | 8/2007 | Mori et al. |
| 2007/0213690 A1 | 9/2007 | Phillips et al. |
| 2007/0250148 A1 | 10/2007 | Perry et al. |
| 2007/0253842 A1 | 11/2007 | Horvath et al. |
| 2007/0265673 A1 | 11/2007 | Ransbury et al. |
| 2007/0270633 A1* | 11/2007 | Cook .................. A61M 60/824 |
| | | | 600/16 |
| 2007/0299314 A1 | 12/2007 | Bertolero et al. |
| 2008/0045779 A1 | 2/2008 | Rinaldi et al. |
| 2008/0065014 A1 | 3/2008 | Von Oepen et al. |
| 2008/0076101 A1 | 3/2008 | Hyde et al. |
| 2008/0097273 A1 | 4/2008 | Levin et al. |

(56) References Cited

U.S. PATENT DOCUMENTS

| 2008/0097562 A1 | 4/2008 | Tan |
| 2008/0119421 A1 | 5/2008 | Tuszynski et al. |
| 2008/0132748 A1 | 6/2008 | Shifflette |
| 2008/0132749 A1 | 6/2008 | Hegde et al. |
| 2008/0167679 A1 | 7/2008 | Papp |
| 2008/0167711 A1 | 7/2008 | Roorda |
| 2008/0188923 A1 | 8/2008 | Chu |
| 2008/0200750 A1 | 8/2008 | James |
| 2008/0208329 A1 | 8/2008 | Bishop et al. |
| 2008/0228026 A1 | 9/2008 | Manera et al. |
| 2008/0240947 A1 | 10/2008 | Allaire et al. |
| 2008/0243030 A1 | 10/2008 | Seibel et al. |
| 2008/0275295 A1 | 11/2008 | Gertner |
| 2008/0275354 A1 | 11/2008 | Thuramalla et al. |
| 2008/0296433 A1 | 12/2008 | Brenner et al. |
| 2008/0300677 A1 | 12/2008 | Schrayer |
| 2009/0012460 A1 | 1/2009 | Steck et al. |
| 2009/0061072 A1 | 3/2009 | Isch et al. |
| 2009/0063402 A1 | 3/2009 | Hayter |
| 2009/0082723 A1 | 3/2009 | Krogh et al. |
| 2009/0143635 A1 | 6/2009 | Benkowski et al. |
| 2009/0171448 A1 | 7/2009 | Eli |
| 2009/0177028 A1 | 7/2009 | White |
| 2009/0182307 A1 | 7/2009 | Yap et al. |
| 2009/0188964 A1 | 7/2009 | Orlov |
| 2009/0259089 A1 | 10/2009 | Gelbart et al. |
| 2010/0016703 A1 | 1/2010 | Batkin et al. |
| 2010/0022943 A1 | 1/2010 | Mauch et al. |
| 2010/0042037 A1 | 2/2010 | Felt et al. |
| 2010/0076380 A1 | 3/2010 | Hui |
| 2010/0084326 A1 | 4/2010 | Takesawa |
| 2010/0087742 A1 | 4/2010 | Bishop et al. |
| 2010/0105978 A1 | 4/2010 | Matsui et al. |
| 2010/0152523 A1 | 6/2010 | MacDonald et al. |
| 2010/0152525 A1 | 6/2010 | Weizman et al. |
| 2010/0152526 A1 | 6/2010 | Pacella et al. |
| 2010/0160751 A1 | 6/2010 | Hete et al. |
| 2010/0184318 A1 | 7/2010 | Bogart et al. |
| 2010/0185220 A1 | 7/2010 | Naghavi et al. |
| 2010/0222635 A1 | 9/2010 | Poirier |
| 2010/0222878 A1 | 9/2010 | Poirier |
| 2010/0249489 A1 | 9/2010 | Jarvik |
| 2011/0098548 A1 | 4/2011 | Budiman et al. |
| 2011/0106115 A1 | 5/2011 | Haselby et al. |
| 2011/0106120 A1 | 5/2011 | Haselby et al. |
| 2011/0178596 A1 | 7/2011 | Hauck et al. |
| 2011/0224655 A1 | 9/2011 | Asirvatham et al. |
| 2011/0297599 A1 | 12/2011 | Lo et al. |
| 2011/0301625 A1 | 12/2011 | Mauch et al. |
| 2011/0304240 A1 | 12/2011 | Meitav et al. |
| 2012/0022316 A1 | 1/2012 | Aboul-Hosn et al. |
| 2012/0028908 A1 | 2/2012 | Viswanath et al. |
| 2012/0039711 A1 | 2/2012 | Roehn |
| 2012/0109060 A1 | 5/2012 | Kick et al. |
| 2012/0165641 A1 | 6/2012 | Burnett et al. |
| 2012/0179184 A1 | 7/2012 | Orlov |
| 2012/0184803 A1 | 7/2012 | Simon et al. |
| 2012/0190918 A1 | 7/2012 | Oepen et al. |
| 2012/0239139 A1 | 9/2012 | Wnendt et al. |
| 2012/0252709 A1 | 10/2012 | Felts et al. |
| 2012/0289928 A1 | 11/2012 | Wright et al. |
| 2012/0302458 A1 | 11/2012 | Adamczyk et al. |
| 2012/0330683 A1 | 12/2012 | Ledwidge et al. |
| 2013/0023373 A1 | 1/2013 | Janek |
| 2013/0040407 A1 | 2/2013 | Brophy et al. |
| 2013/0053693 A1 | 2/2013 | Breznock et al. |
| 2013/0144144 A1 | 6/2013 | Laster et al. |
| 2013/0211489 A1 | 8/2013 | Makower et al. |
| 2013/0233798 A1 | 9/2013 | Wiktor et al. |
| 2013/0245360 A1 | 9/2013 | Schumacher |
| 2013/0267892 A1 | 10/2013 | Woolford |
| 2013/0281761 A1 | 10/2013 | Kapur |
| 2013/0289696 A1 | 10/2013 | Maggard et al. |
| 2013/0310845 A1 | 11/2013 | Thor et al. |
| 2013/0317604 A1 | 11/2013 | Min et al. |
| 2013/0344047 A1 | 12/2013 | Pacetti et al. |
| 2014/0017200 A1 | 1/2014 | Michal et al. |
| 2014/0039465 A1 | 2/2014 | Schulz et al. |
| 2014/0039603 A1 | 2/2014 | Wang |
| 2014/0051908 A1 | 2/2014 | Khanal et al. |
| 2014/0058190 A1 | 2/2014 | Gohean et al. |
| 2014/0066693 A1 | 3/2014 | Goldfarb et al. |
| 2014/0128659 A1 | 5/2014 | Heuring et al. |
| 2014/0128795 A1 | 5/2014 | Keren et al. |
| 2014/0142617 A1 | 5/2014 | Larsen et al. |
| 2014/0148638 A1 | 5/2014 | LaRose et al. |
| 2014/0163664 A1 | 6/2014 | Goldsmith |
| 2014/0190523 A1 | 7/2014 | Garvey et al. |
| 2014/0194678 A1 | 7/2014 | Wildhirt et al. |
| 2014/0194717 A1 | 7/2014 | Wildhirt et al. |
| 2014/0199377 A1 | 7/2014 | Stankus et al. |
| 2014/0200655 A1 | 7/2014 | Webler et al. |
| 2014/0207232 A1 | 7/2014 | Garrigue |
| 2014/0228741 A1 | 8/2014 | Frankowski et al. |
| 2014/0243970 A1 | 8/2014 | Yanai |
| 2014/0255176 A1 | 9/2014 | Bredenbreuker et al. |
| 2014/0260551 A1 | 9/2014 | Gray et al. |
| 2014/0275721 A1 | 9/2014 | Yanai et al. |
| 2014/0275725 A1 | 9/2014 | Schenck et al. |
| 2014/0288354 A1 | 9/2014 | Timms et al. |
| 2014/0309481 A1 | 10/2014 | Medvedev et al. |
| 2014/0336444 A1 | 11/2014 | Bonde |
| 2014/0336486 A1 | 11/2014 | Ouyang et al. |
| 2014/0336747 A1 | 11/2014 | Rapoza et al. |
| 2014/0341726 A1 | 11/2014 | Wu et al. |
| 2014/0350328 A1 | 11/2014 | Mohl |
| 2014/0355938 A1 | 12/2014 | Pilla et al. |
| 2014/0370073 A1 | 12/2014 | Tang et al. |
| 2015/0005571 A1 | 1/2015 | Jeffery et al. |
| 2015/0018747 A1 | 1/2015 | Michal et al. |
| 2015/0031938 A1 | 1/2015 | Crosby et al. |
| 2015/0051437 A1 | 2/2015 | Miyakoshi et al. |
| 2015/0068069 A1 | 3/2015 | Tran et al. |
| 2015/0080639 A1 | 3/2015 | Radziemski et al. |
| 2015/0080743 A1 | 3/2015 | Siess |
| 2015/0087890 A1 | 3/2015 | Spanier et al. |
| 2015/0101645 A1 | 4/2015 | Neville et al. |
| 2015/0112210 A1 | 4/2015 | Webler |
| 2015/0119859 A1 | 4/2015 | Cajamarca et al. |
| 2015/0120323 A1 | 4/2015 | Galasso et al. |
| 2015/0134048 A1 | 5/2015 | Ding |
| 2015/0152878 A1 | 6/2015 | McBride et al. |
| 2015/0159643 A1 | 6/2015 | Koob |
| 2015/0174060 A1 | 6/2015 | Heit et al. |
| 2015/0191607 A1 | 7/2015 | McDaniel |
| 2015/0207331 A1 | 7/2015 | Petersen |
| 2015/0216685 A1 | 8/2015 | Spence et al. |
| 2015/0222128 A1 | 8/2015 | Hansen |
| 2015/0222139 A1 | 8/2015 | Petersen et al. |
| 2015/0226691 A1 | 8/2015 | Wang et al. |
| 2015/0230709 A1 | 8/2015 | Milner et al. |
| 2015/0231317 A1 | 8/2015 | Schima et al. |
| 2015/0238671 A1 | 8/2015 | Mesallum |
| 2015/0265757 A1 | 9/2015 | Dowling et al. |
| 2015/0283027 A1 | 10/2015 | Lampe et al. |
| 2015/0285258 A1 | 10/2015 | Foster |
| 2015/0290370 A1 | 10/2015 | Crunkleton et al. |
| 2015/0290377 A1 | 10/2015 | Kearsley et al. |
| 2015/0306291 A1 | 10/2015 | Bonde et al. |
| 2015/0320926 A1 | 11/2015 | Fitzpatrick et al. |
| 2015/0328382 A1 | 11/2015 | Corbett et al. |
| 2015/0335803 A1 | 11/2015 | Yamane |
| 2015/0364861 A1 | 12/2015 | Lucke et al. |
| 2015/0366495 A1 | 12/2015 | Gable, III et al. |
| 2015/0367050 A1 | 12/2015 | Bulent et al. |
| 2015/0368335 A1 | 12/2015 | Banerjee et al. |
| 2015/0374892 A1 | 12/2015 | Yanai et al. |
| 2016/0022887 A1 | 1/2016 | Wampler |
| 2016/0022890 A1 | 1/2016 | Schwammenthal et al. |
| 2016/0030649 A1 | 2/2016 | Zeng |
| 2016/0038315 A1 | 2/2016 | Consigny et al. |
| 2016/0045098 A1 | 2/2016 | Tsubouchi |
| 2016/0045652 A1 | 2/2016 | Cornen |
| 2016/0045654 A1 | 2/2016 | Connor |

(56) References Cited

U.S. PATENT DOCUMENTS

| | | | |
|---|---|---|---|
| 2016/0053763 A1 | 2/2016 | Toellner |
| 2016/0058434 A1 | 3/2016 | Delaloye et al. |
| 2016/0067395 A1 | 3/2016 | Jimenez et al. |
| 2016/0085714 A1 | 3/2016 | Goodnow et al. |
| 2016/0175044 A1 | 6/2016 | Abunassar et al. |
| 2016/0182158 A1 | 6/2016 | Lee et al. |
| 2016/0184499 A1 | 6/2016 | Ricci et al. |
| 2016/0199543 A1 | 7/2016 | Venkateswara-Rao |
| 2016/0199556 A1 | 7/2016 | Ayre et al. |
| 2016/0199557 A1 | 7/2016 | Bluvshtein et al. |
| 2016/0203275 A1 | 7/2016 | Benjamin et al. |
| 2016/0206798 A1 | 7/2016 | Williams et al. |
| 2016/0213827 A1* | 7/2016 | Tanner ................ A61M 60/808 |
| 2016/0220269 A1 | 8/2016 | Labropoulos et al. |
| 2016/0220785 A1 | 8/2016 | Fabro |
| 2016/0222969 A1 | 8/2016 | Heide et al. |
| 2016/0250399 A1 | 9/2016 | Tiller et al. |
| 2016/0250400 A1 | 9/2016 | Schumacher |
| 2016/0251720 A1 | 9/2016 | Schulze et al. |
| 2016/0256620 A1 | 9/2016 | Scheckel et al. |
| 2016/0263299 A1 | 9/2016 | Xu et al. |
| 2016/0271161 A1 | 9/2016 | Dobson |
| 2016/0271309 A1 | 9/2016 | Throckmorton et al. |
| 2016/0279310 A1 | 9/2016 | Scheckel et al. |
| 2016/0303301 A1 | 10/2016 | Bluvshtein et al. |
| 2016/0308403 A1 | 10/2016 | Bluvshtein et al. |
| 2016/0317291 A1 | 11/2016 | Bishop et al. |
| 2016/0317333 A1 | 11/2016 | Ainsworth et al. |
| 2016/0325034 A1 | 11/2016 | Wiktor et al. |
| 2016/0348688 A1 | 12/2016 | Schumacher et al. |
| 2016/0354526 A1 | 12/2016 | Whisenant et al. |
| 2016/0375187 A1 | 12/2016 | Lee et al. |
| 2017/0000361 A1 | 1/2017 | Meyering et al. |
| 2017/0000935 A1 | 1/2017 | Vasilyev et al. |
| 2017/0007552 A1 | 1/2017 | Slepian |
| 2017/0007762 A1 | 1/2017 | Hayter et al. |
| 2017/0014401 A1 | 1/2017 | Dalton et al. |
| 2017/0014562 A1 | 1/2017 | Liebing |
| 2017/0021074 A1 | 1/2017 | Opfermann et al. |
| 2017/0028114 A1 | 2/2017 | Göllner et al. |
| 2017/0028115 A1 | 2/2017 | Muller |
| 2017/0035952 A1 | 2/2017 | Muller |
| 2017/0035954 A1 | 2/2017 | Muller et al. |
| 2017/0037860 A1 | 2/2017 | Toellner |
| 2017/0043076 A1 | 2/2017 | Wampler et al. |
| 2017/0063143 A1 | 3/2017 | Hoarau et al. |
| 2017/0080136 A1 | 3/2017 | Janeczek et al. |
| 2017/0100527 A1 | 4/2017 | Schwammenthal et al. |
| 2017/0112984 A1 | 4/2017 | Vargas Fonseca |
| 2017/0119945 A1 | 5/2017 | Neumann |
| 2017/0119946 A1 | 5/2017 | McChrystal et al. |
| 2017/0136165 A1 | 5/2017 | Hansen et al. |
| 2017/0136225 A1 | 5/2017 | Siess et al. |
| 2017/0143883 A1 | 5/2017 | Spence |
| 2017/0143952 A1 | 5/2017 | Siess et al. |
| 2017/0157309 A1 | 6/2017 | Begg et al. |
| 2017/0173242 A1 | 6/2017 | Anderson et al. |
| 2017/0193184 A1 | 7/2017 | Hayter et al. |
| 2017/0196638 A1 | 7/2017 | Serna et al. |
| 2017/0202575 A1 | 7/2017 | Stanfield et al. |
| 2017/0215918 A1 | 8/2017 | Tao et al. |
| 2017/0224896 A1 | 8/2017 | Graham et al. |
| 2017/0232168 A1 | 8/2017 | Reichenbach et al. |
| 2017/0232169 A1 | 8/2017 | Muller |
| 2017/0232172 A1 | 8/2017 | Mesallum |
| 2017/0239407 A1 | 8/2017 | Hayward |
| 2017/0250575 A1 | 8/2017 | Wong et al. |
| 2017/0265994 A1 | 9/2017 | Krone |
| 2017/0274128 A1 | 9/2017 | Tamburino et al. |
| 2017/0281025 A9 | 10/2017 | Glover et al. |
| 2017/0281841 A1 | 10/2017 | Larose et al. |
| 2017/0281842 A1 | 10/2017 | Larose et al. |
| 2017/0290964 A1 | 10/2017 | Barry |
| 2017/0296227 A1 | 10/2017 | Osypka |
| 2017/0296725 A1 | 10/2017 | Peters et al. |
| 2017/0312106 A1 | 11/2017 | Gomez et al. |
| 2017/0312416 A1 | 11/2017 | Strueber |
| 2017/0312492 A1 | 11/2017 | Fantuzzi et al. |
| 2017/0319113 A1 | 11/2017 | Hurd et al. |
| 2017/0323713 A1 | 11/2017 | Moeller et al. |
| 2017/0325943 A1 | 11/2017 | Robin et al. |
| 2017/0333607 A1 | 11/2017 | Zarins |
| 2017/0333673 A1 | 11/2017 | Tuval et al. |
| 2017/0340788 A1 | 11/2017 | Korakianitis et al. |
| 2017/0340789 A1 | 11/2017 | Bonde et al. |
| 2017/0340790 A1 | 11/2017 | Wiesener et al. |
| 2017/0348470 A1 | 12/2017 | D'Ambrosio et al. |
| 2017/0360309 A1 | 12/2017 | Moore et al. |
| 2017/0361001 A1 | 12/2017 | Canatella et al. |
| 2017/0361011 A1 | 12/2017 | Muennich et al. |
| 2017/0363103 A1 | 12/2017 | Canatella et al. |
| 2017/0363210 A1 | 12/2017 | Durst et al. |
| 2017/0363620 A1 | 12/2017 | Beshiri et al. |
| 2017/0368246 A1 | 12/2017 | Criscione et al. |
| 2017/0370365 A1 | 12/2017 | Fritz et al. |
| 2018/0001003 A1 | 1/2018 | Moran et al. |
| 2018/0001007 A1 | 1/2018 | Stratton |
| 2018/0001012 A1 | 1/2018 | Ardehali |
| 2018/0001062 A1 | 1/2018 | O'Carrol et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0021497 A1 | 1/2018 | Nunez et al. |
| 2018/0028736 A1 | 2/2018 | Wong et al. |
| 2018/0035926 A1 | 2/2018 | Stafford |
| 2018/0040418 A1 | 2/2018 | Hansen et al. |
| 2018/0047282 A1 | 2/2018 | He et al. |
| 2018/0050139 A1 | 2/2018 | Siess et al. |
| 2018/0050140 A1 | 2/2018 | Siess et al. |
| 2018/0050142 A1 | 2/2018 | Siess et al. |
| 2018/0055383 A1 | 3/2018 | Manera |
| 2018/0055983 A1 | 3/2018 | Bourque |
| 2018/0058437 A1 | 3/2018 | Eilers et al. |
| 2018/0064862 A1 | 3/2018 | Keenan et al. |
| 2018/0071020 A1 | 3/2018 | Laufer et al. |
| 2018/0078159 A1 | 3/2018 | Edelman et al. |
| 2018/0080326 A1 | 3/2018 | Schumacher et al. |
| 2018/0085505 A1 | 3/2018 | Casas |
| 2018/0085507 A1 | 3/2018 | Casas et al. |
| 2018/0085509 A1 | 3/2018 | Petersen |
| 2018/0093026 A1 | 4/2018 | Angwin et al. |
| 2018/0097368 A1 | 4/2018 | Hansen |
| 2018/0099076 A1 | 4/2018 | Larose |
| 2018/0099078 A1 | 4/2018 | Tuseth et al. |
| 2018/0100507 A1 | 4/2018 | Wu et al. |
| 2018/0103611 A1 | 4/2018 | Mainini et al. |
| 2018/0103870 A1 | 4/2018 | Limaye et al. |
| 2018/0108275 A1 | 4/2018 | Newberry et al. |
| 2018/0110514 A1 | 4/2018 | Hoarau et al. |
| 2018/0114426 A1 | 4/2018 | Lee |
| 2018/0133380 A1 | 5/2018 | Liebing |
| 2018/0140759 A1 | 5/2018 | Kaiser et al. |
| 2018/0140801 A1 | 5/2018 | Voss et al. |
| 2018/0146968 A1 | 5/2018 | Nitzan et al. |
| 2018/0149164 A1 | 5/2018 | Siess |
| 2018/0149165 A1 | 5/2018 | Siess et al. |
| 2018/0154051 A1 | 6/2018 | Hossainy et al. |
| 2018/0154128 A1 | 6/2018 | Woo et al. |
| 2018/0161540 A1 | 6/2018 | Fantuzzi et al. |
| 2018/0161555 A1 | 6/2018 | Zhadkevich |
| 2018/0168469 A1 | 6/2018 | Granegger |
| 2018/0169312 A1 | 6/2018 | Barry |
| 2018/0169313 A1* | 6/2018 | Schwammenthal ........................ A61M 60/808 |
| 2018/0193543 A1 | 7/2018 | Sun |
| 2018/0193614 A1 | 7/2018 | Nitzan et al. |
| 2018/0193616 A1 | 7/2018 | Nitzan et al. |
| 2018/0200420 A1 | 7/2018 | Di Paola et al. |
| 2018/0200422 A1 | 7/2018 | Nguyen et al. |
| 2018/0202962 A1 | 7/2018 | Simmons et al. |
| 2018/0207334 A1 | 7/2018 | Siess |
| 2018/0207337 A1 | 7/2018 | Spence et al. |
| 2018/0207338 A1 | 7/2018 | Bluvshtein et al. |
| 2018/0226997 A1 | 8/2018 | Jia |

(56) References Cited

U.S. PATENT DOCUMENTS

| | | |
|---|---|---|
| 2018/0228953 A1 | 8/2018 | Siess et al. |
| 2018/0228957 A1 | 8/2018 | Colella |
| 2018/0242891 A1 | 8/2018 | Bernstein et al. |
| 2018/0242976 A1 | 8/2018 | Kizuka |
| 2018/0243086 A1 | 8/2018 | Barbarino et al. |
| 2018/0243488 A1 | 8/2018 | Callaway et al. |
| 2018/0243489 A1 | 8/2018 | Haddadi |
| 2018/0243490 A1 | 8/2018 | Kallenbach et al. |
| 2018/0243492 A1 | 8/2018 | Salys |
| 2018/0250457 A1 | 9/2018 | Morello et al. |
| 2018/0250458 A1 | 9/2018 | Petersen et al. |
| 2018/0256242 A1 | 9/2018 | Bluvshtein et al. |
| 2018/0256794 A1 | 9/2018 | Rodefeld |
| 2018/0256795 A1 | 9/2018 | Schade et al. |
| 2018/0256797 A1 | 9/2018 | Schenck et al. |
| 2018/0256798 A1 | 9/2018 | Botterbusch et al. |
| 2018/0256859 A1 | 9/2018 | Korkuch |
| 2018/0264183 A1 | 9/2018 | Jahangir |
| 2018/0264184 A1 | 9/2018 | Jeffries et al. |
| 2018/0269692 A1 | 9/2018 | Petersen et al. |
| 2018/0280598 A1 | 10/2018 | Curran et al. |
| 2018/0280599 A1 | 10/2018 | Harjes et al. |
| 2018/0280600 A1 | 10/2018 | Harjes et al. |
| 2018/0280601 A1 | 10/2018 | Harjes et al. |
| 2018/0280604 A1 | 10/2018 | Hobro et al. |
| 2018/0289295 A1 | 10/2018 | Hoss et al. |
| 2018/0289876 A1 | 10/2018 | Nguyen et al. |
| 2018/0289877 A1 | 10/2018 | Schumacher et al. |
| 2018/0296572 A1 | 10/2018 | Deisher |
| 2018/0303990 A1* | 10/2018 | Siess .................. A61M 60/825 |
| 2019/0030231 A1 | 1/2019 | Aboul-Hosn et al. |
| 2019/0070345 A1 | 3/2019 | McBride et al. |
| 2019/0076167 A1 | 3/2019 | Fantuzzi et al. |
| 2019/0083690 A1 | 3/2019 | Siess et al. |
| 2019/0143018 A1 | 5/2019 | Salahieh et al. |
| 2019/0167873 A1 | 6/2019 | Koike et al. |
| 2019/0209751 A1 | 7/2019 | Tuval et al. |
| 2019/0209758 A1* | 7/2019 | Tuval .................. A61M 60/414 |
| 2019/0290822 A1 | 9/2019 | Igarashi |
| 2019/0311850 A1* | 10/2019 | Siess .................. A61M 60/829 |
| 2019/0321531 A1 | 10/2019 | Cambronne et al. |
| 2020/0029951 A1 | 1/2020 | Bessler et al. |
| 2020/0030510 A1 | 1/2020 | Higgins |
| 2020/0038568 A1 | 2/2020 | Higgins et al. |
| 2020/0121835 A1 | 4/2020 | Farago et al. |
| 2020/0237981 A1 | 7/2020 | Tuval et al. |
| 2020/0246527 A1 | 8/2020 | Hildebrand et al. |
| 2020/0316268 A1 | 10/2020 | Antoni et al. |
| 2020/0391014 A1 | 12/2020 | Walters et al. |
| 2021/0008261 A1 | 1/2021 | Calomeni et al. |
| 2021/0023285 A1 | 1/2021 | Brandt |
| 2021/0038786 A1 | 2/2021 | Calomeni et al. |
| 2021/0052794 A1 | 2/2021 | Tuval et al. |
| 2021/0113212 A1 | 4/2021 | Lashinski et al. |
| 2021/0121679 A1 | 4/2021 | Mohl et al. |
| 2021/0138201 A1 | 5/2021 | Schumacher et al. |
| 2021/0236797 A1 | 8/2021 | D'Ambrosio et al. |
| 2021/0244937 A1 | 8/2021 | Calomeni et al. |
| 2021/0252271 A1 | 8/2021 | Wallin et al. |
| 2021/0252274 A1 | 8/2021 | Dhaliwal et al. |
| 2021/0308444 A1 | 10/2021 | Saul et al. |
| 2022/0080178 A1 | 3/2022 | Salahieh et al. |
| 2022/0105337 A1 | 4/2022 | Salahieh et al. |
| 2022/0203084 A1 | 6/2022 | Zarins et al. |
| 2022/0233841 A1 | 7/2022 | Hildebrand et al. |
| 2022/0273933 A1 | 9/2022 | Ryan et al. |
| 2023/0109991 A1 | 4/2023 | Hildebrand et al. |
| 2023/0218886 A1 | 7/2023 | Robinson et al. |
| 2023/0264012 A1 | 8/2023 | Brandt |
| 2023/0390544 A1 | 12/2023 | Hildebrand et al. |
| 2023/0405298 A1 | 12/2023 | Hildebrand et al. |
| 2023/0414920 A1 | 12/2023 | Salahieh et al. |
| 2024/0001101 A1 | 1/2024 | Wallin et al. |
| 2024/0115849 A1 | 4/2024 | Dhaliwal et al. |
| 2024/0139499 A1 | 5/2024 | Salahieh et al. |
| 2024/0149046 A1 | 5/2024 | Calomeni et al. |
| 2024/0157117 A1 | 5/2024 | Ryan et al. |
| 2024/0173540 A1 | 5/2024 | Wallin et al. |
| 2024/0181238 A1 | 6/2024 | Ryan et al. |

FOREIGN PATENT DOCUMENTS

| | | | |
|---|---|---|---|
| CA | 3014105 A1 | 8/2017 | |
| CN | 1040073 A | 2/1990 | |
| CN | 1008307 B | 6/1990 | |
| CN | 1053108 A | 7/1991 | |
| CN | 1105103 A | 7/1995 | |
| CN | 1146329 A | 4/1997 | |
| CN | 1179708 A | 4/1998 | |
| CN | 2326258 Y | 6/1999 | |
| CN | 1222862 A | 7/1999 | |
| CN | 1045058 C | 9/1999 | |
| CN | 1235849 A | 11/1999 | |
| CN | 2361290 Y | 2/2000 | |
| CN | 1254598 A | 5/2000 | |
| CN | 2386827 Y | 7/2000 | |
| CN | 2412579 Y | 1/2001 | |
| CN | 2417173 Y | 1/2001 | |
| CN | 1310647 A | 8/2001 | |
| CN | 1342497 A | 4/2002 | |
| CN | 1088795 C | 8/2002 | |
| CN | 2504815 Y | 8/2002 | |
| CN | 1376523 A | 10/2002 | |
| CN | 1097138 C | 12/2002 | |
| CN | 1105581 C | 4/2003 | |
| CN | 1421248 A | 6/2003 | |
| CN | 2558386 Y | 7/2003 | |
| CN | 1118304 C | 8/2003 | |
| CN | 1436048 A | 8/2003 | |
| CN | 1120729 C | 9/2003 | |
| CN | 2574609 Y | 9/2003 | |
| CN | 1140228 C | 3/2004 | |
| CN | 1161581 C | 8/2004 | |
| CN | 1167472 C | 9/2004 | |
| CN | 1527906 A | 9/2004 | |
| CN | 1559361 A | 1/2005 | |
| CN | 1559626 A | 1/2005 | |
| CN | 1572331 A | 2/2005 | |
| CN | 1202871 C | 5/2005 | |
| CN | 1679974 A | 10/2005 | |
| CN | 1694338 A | 11/2005 | |
| CN | 1705462 A | 12/2005 | |
| CN | 1239133 C | 2/2006 | |
| CN | 1239209 C | 2/2006 | |
| CN | 2754637 Y | 2/2006 | |
| CN | 1244381 C | 3/2006 | |
| CN | 1249339 C | 4/2006 | |
| CN | 2776418 Y | 5/2006 | |
| CN | 2787222 Y | 6/2006 | |
| CN | 1799652 A | 7/2006 | |
| CN | 1806774 A | 7/2006 | |
| CN | 1826463 A | 8/2006 | |
| CN | 1833735 A | 9/2006 | |
| CN | 1833736 A | 9/2006 | |
| CN | 2831716 Y | 10/2006 | |
| CN | 1874805 A | 12/2006 | |
| CN | 1301583 C | 2/2007 | |
| CN | 1921947 A | 2/2007 | |
| CN | 2880096 Y | 3/2007 | |
| CN | 2899800 Y | 5/2007 | |
| CN | 101001765 A | 7/2007 | |
| CN | 1329666 C | 8/2007 | |
| CN | 101024098 A | 8/2007 | |
| CN | 101031302 A | 9/2007 | |
| CN | 101112628 A | 1/2008 | |
| CN | 101121045 A | 2/2008 | |
| CN | 101124002 A | 2/2008 | |
| CN | 101132830 A | 2/2008 | |
| CN | 100382855 C | 4/2008 | |
| CN | 101256992 A | 9/2008 | |
| CN | 100429406 C | 10/2008 | |
| CN | 100439717 C | 12/2008 | |
| CN | 100472042 C | 3/2009 | |
| CN | 201208423 Y | 3/2009 | |

(56)                    References Cited

FOREIGN PATENT DOCUMENTS

| | | | |
|---|---|---|---|
| CN | 100488577 | C | 5/2009 |
| CN | 201230980 | Y | 5/2009 |
| CN | 201239369 | Y | 5/2009 |
| CN | 201246310 | Y | 5/2009 |
| CN | 101448535 | A | 6/2009 |
| CN | 101522115 | A | 9/2009 |
| CN | 101534883 | A | 9/2009 |
| CN | 201308666 | Y | 9/2009 |
| CN | 101563605 | A | 10/2009 |
| CN | 100558416 | C | 11/2009 |
| CN | 100566765 | C | 12/2009 |
| CN | 101595276 | A | 12/2009 |
| CN | 101631578 | A | 1/2010 |
| CN | 101652069 | A | 2/2010 |
| CN | 101678025 | A | 3/2010 |
| CN | 101687791 | A | 3/2010 |
| CN | 101244296 | B | 6/2010 |
| CN | 101730552 | A | 6/2010 |
| CN | 101208058 | B | 8/2010 |
| CN | 101808515 | A | 8/2010 |
| CN | 101401981 | B | 9/2010 |
| CN | 101843528 | A | 9/2010 |
| CN | 101232952 | B | 11/2010 |
| CN | 101361994 | B | 11/2010 |
| CN | 201618200 | U | 11/2010 |
| CN | 201710717 | U | 1/2011 |
| CN | 101417155 | B | 2/2011 |
| CN | 101581307 | B | 4/2011 |
| CN | 102065923 | A | 5/2011 |
| CN | 101269245 | B | 7/2011 |
| CN | 101618240 | B | 8/2011 |
| CN | 102166379 | A | 8/2011 |
| CN | 101484093 | B | 9/2011 |
| CN | 102292053 | A | 12/2011 |
| CN | 102422018 | A | 4/2012 |
| CN | 102438673 | A | 5/2012 |
| CN | 102475923 | A | 5/2012 |
| CN | 202218993 | U | 5/2012 |
| CN | 101983732 | B | 7/2012 |
| CN | 102553005 | A | 7/2012 |
| CN | 101590295 | B | 8/2012 |
| CN | 101822854 | B | 9/2012 |
| CN | 101822855 | B | 9/2012 |
| CN | 101189431 | B | 10/2012 |
| CN | 101810891 | B | 10/2012 |
| CN | 102711862 | A | 10/2012 |
| CN | 102711894 | A | 10/2012 |
| CN | 102869318 | A | 1/2013 |
| CN | 102917748 | A | 2/2013 |
| CN | 102088920 | B | 4/2013 |
| CN | 103026234 | A | 4/2013 |
| CN | 103068417 | A | 4/2013 |
| CN | 103172739 | A | 6/2013 |
| CN | 101420993 | B | 7/2013 |
| CN | 103206402 | A | 7/2013 |
| CN | 103228300 | A | 7/2013 |
| CN | 103356306 | A | 10/2013 |
| CN | 103381277 | A | 11/2013 |
| CN | 103432637 | A | 12/2013 |
| CN | 103437951 | A | 12/2013 |
| CN | 103446635 | A | 12/2013 |
| CN | 103458832 | A | 12/2013 |
| CN | 102319457 | B | 1/2014 |
| CN | 103509116 | A | 1/2014 |
| CN | 103541857 | A | 1/2014 |
| CN | 103635212 | A | 3/2014 |
| CN | 203507200 | U | 4/2014 |
| CN | 203539803 | U | 4/2014 |
| CN | 203591299 | U | 5/2014 |
| CN | 102317629 | B | 8/2014 |
| CN | 203756589 | U | 8/2014 |
| CN | 104043153 | A | 9/2014 |
| CN | 203829160 | U | 9/2014 |
| CN | 104105511 | A | 10/2014 |
| CN | 203935281 | U | 11/2014 |
| CN | 104185456 | A | 12/2014 |
| CN | 104208763 | A | 12/2014 |
| CN | 203971002 | U | 12/2014 |
| CN | 204050452 | U | 12/2014 |
| CN | 102271728 | B | 1/2015 |
| CN | 102294057 | B | 1/2015 |
| CN | 104271075 | A | 1/2015 |
| CN | 102588255 | B | 3/2015 |
| CN | 104470454 | A | 3/2015 |
| CN | 102300501 | B | 4/2015 |
| CN | 103055363 | B | 4/2015 |
| CN | 104473676 | A | 4/2015 |
| CN | 104524663 | A | 4/2015 |
| CN | 204293210 | U | 4/2015 |
| CN | 102686316 | B | 5/2015 |
| CN | 104586469 | A | 5/2015 |
| CN | 104602987 | A | 5/2015 |
| CN | 102458275 | B | 6/2015 |
| CN | 102458498 | B | 6/2015 |
| CN | 104684607 | A | 6/2015 |
| CN | 104721899 | A | 6/2015 |
| CN | 204419151 | U | 6/2015 |
| CN | 102397598 | B | 7/2015 |
| CN | 103446634 | B | 7/2015 |
| CN | 104758029 | A | 7/2015 |
| CN | 104771797 | A | 7/2015 |
| CN | 101868628 | B | 8/2015 |
| CN | 103706018 | B | 9/2015 |
| CN | 104955420 | A | 9/2015 |
| CN | 104984425 | A | 10/2015 |
| CN | 104997550 | A | 10/2015 |
| CN | 105007960 | A | 10/2015 |
| CN | 105142719 | A | 12/2015 |
| CN | 105208927 | A | 12/2015 |
| CN | 102176933 | B | 1/2016 |
| CN | 102947092 | B | 1/2016 |
| CN | 103717837 | B | 1/2016 |
| CN | 105228688 | A | 1/2016 |
| CN | 105283149 | A | 1/2016 |
| CN | 204972635 | U | 1/2016 |
| CN | 103228232 | B | 2/2016 |
| CN | 103355925 | B | 2/2016 |
| CN | 105311692 | A | 2/2016 |
| CN | 102257279 | B | 3/2016 |
| CN | 102472719 | B | 3/2016 |
| CN | 103154738 | B | 3/2016 |
| CN | 105451787 | A | 3/2016 |
| CN | 205083494 | U | 3/2016 |
| CN | 103850979 | B | 4/2016 |
| CN | 105477706 | A | 4/2016 |
| CN | 105517589 | A | 4/2016 |
| CN | 205163763 | U | 4/2016 |
| CN | 103002833 | B | 5/2016 |
| CN | 103861163 | B | 5/2016 |
| CN | 105555204 | A | 5/2016 |
| CN | 205215814 | U | 5/2016 |
| CN | 102940911 | B | 6/2016 |
| CN | 105641762 | A | 6/2016 |
| CN | 105641763 | A | 6/2016 |
| CN | 105662439 | A | 6/2016 |
| CN | 105709287 | A | 6/2016 |
| CN | 105722477 | A | 6/2016 |
| CN | 205322884 | U | 6/2016 |
| CN | 104069555 | B | 7/2016 |
| CN | 105744915 | A | 7/2016 |
| CN | 105790453 | A | 7/2016 |
| CN | 105792780 | A | 7/2016 |
| CN | 105792864 | A | 7/2016 |
| CN | 103260666 | B | 8/2016 |
| CN | 103732171 | B | 8/2016 |
| CN | 103928971 | B | 8/2016 |
| CN | 105833370 | A | 8/2016 |
| CN | 205411785 | U | 8/2016 |
| CN | 205460099 | U | 8/2016 |
| CN | 205528886 | U | 8/2016 |
| CN | 103889369 | B | 9/2016 |
| CN | 104849482 | B | 9/2016 |
| CN | 105980660 | A | 9/2016 |
| CN | 106075621 | A | 11/2016 |

(56)          References Cited

FOREIGN PATENT DOCUMENTS

| | | | |
|---|---|---|---|
| CN | 106102657 | A | 11/2016 |
| CN | 205681272 | U | 11/2016 |
| CN | 205698666 | U | 11/2016 |
| CN | 205698725 | U | 11/2016 |
| CN | 205753678 | U | 11/2016 |
| CN | 106214288 | A | 12/2016 |
| CN | 106256321 | A | 12/2016 |
| CN | 205779766 | U | 12/2016 |
| CN | 106334224 | A | 1/2017 |
| CN | 205867186 | U | 1/2017 |
| CN | 205876589 | U | 1/2017 |
| CN | 103281971 | B | 2/2017 |
| CN | 106390218 | A | 2/2017 |
| CN | 103533970 | B | 3/2017 |
| CN | 104826183 | B | 3/2017 |
| CN | 106512117 | A | 3/2017 |
| CN | 106581840 | A | 4/2017 |
| CN | 104068947 | B | 5/2017 |
| CN | 106620912 | A | 5/2017 |
| CN | 106691363 | A | 5/2017 |
| CN | 106716137 | A | 5/2017 |
| CN | 106794293 | A | 5/2017 |
| CN | 104225696 | B | 6/2017 |
| CN | 104918578 | B | 6/2017 |
| CN | 105915005 | B | 6/2017 |
| CN | 106902404 | A | 6/2017 |
| CN | 106955140 | A | 7/2017 |
| CN | 206325049 | U | 7/2017 |
| CN | 206355093 | U | 7/2017 |
| CN | 105377321 | B | 8/2017 |
| CN | 107050543 | A | 8/2017 |
| CN | 107050544 | A | 8/2017 |
| CN | 107080870 | A | 8/2017 |
| CN | 107080871 | A | 8/2017 |
| CN | 107110875 | A | 8/2017 |
| CN | 206414547 | U | 8/2017 |
| CN | 206443963 | U | 8/2017 |
| CN | 103930214 | B | 9/2017 |
| CN | 104619361 | B | 9/2017 |
| CN | 104936550 | B | 9/2017 |
| CN | 105188618 | B | 9/2017 |
| CN | 107115162 | A | 9/2017 |
| CN | 107126299 | A | 9/2017 |
| CN | 107126588 | A | 9/2017 |
| CN | 107134208 | A | 9/2017 |
| CN | 107157623 | A | 9/2017 |
| CN | 103857363 | B | 10/2017 |
| CN | 104768500 | B | 10/2017 |
| CN | 105008841 | B | 10/2017 |
| CN | 105492036 | B | 10/2017 |
| CN | 107252339 | A | 10/2017 |
| CN | 107281567 | A | 10/2017 |
| CN | 206592332 | U | 10/2017 |
| CN | 107349484 | A | 11/2017 |
| CN | 206660203 | U | 11/2017 |
| CN | 105287050 | B | 12/2017 |
| CN | 105597172 | B | 12/2017 |
| CN | 105854097 | B | 12/2017 |
| CN | 107412892 | A | 12/2017 |
| CN | 107440681 | A | 12/2017 |
| CN | 107496054 | A | 12/2017 |
| CN | 104602647 | B | 1/2018 |
| CN | 106061523 | B | 1/2018 |
| CN | 107551341 | A | 1/2018 |
| CN | 206934393 | U | 1/2018 |
| CN | 107693868 | A | 2/2018 |
| CN | 107693869 | A | 2/2018 |
| CN | 107708765 | A | 2/2018 |
| CN | 207018256 | U | 2/2018 |
| CN | 106029120 | B | 3/2018 |
| CN | 107753153 | A | 3/2018 |
| CN | 107754071 | A | 3/2018 |
| CN | 107798980 | A | 3/2018 |
| CN | 107835826 | A | 3/2018 |
| CN | 107837430 | A | 3/2018 |
| CN | 107862963 | A | 3/2018 |
| CN | 207125933 | U | 3/2018 |
| CN | 207136890 | U | 3/2018 |
| CN | 105120796 | B | 4/2018 |
| CN | 105214153 | B | 4/2018 |
| CN | 107865988 | A | 4/2018 |
| CN | 107886825 | A | 4/2018 |
| CN | 107913442 | A | 4/2018 |
| CN | 107921195 | A | 4/2018 |
| CN | 107923311 | A | 4/2018 |
| CN | 108025120 | A | 5/2018 |
| CN | 108025123 | A | 5/2018 |
| CN | 108066834 | A | 5/2018 |
| CN | 207410652 | U | 5/2018 |
| CN | 104470579 | B | 6/2018 |
| CN | 105188604 | B | 6/2018 |
| CN | 105492909 | B | 6/2018 |
| CN | 105498002 | B | 6/2018 |
| CN | 106535824 | B | 6/2018 |
| CN | 108136110 | A | 6/2018 |
| CN | 108144146 | A | 6/2018 |
| CN | 108175884 | A | 6/2018 |
| CN | 106028807 | B | 7/2018 |
| CN | 106310410 | B | 7/2018 |
| CN | 108273148 | A | 7/2018 |
| CN | 108310486 | A | 7/2018 |
| CN | 108348667 | A | 7/2018 |
| CN | 207614108 | U | 7/2018 |
| CN | 105640635 | B | 8/2018 |
| CN | 105923112 | B | 8/2018 |
| CN | 108367106 | A | 8/2018 |
| CN | 108430533 | A | 8/2018 |
| CN | 108457844 | A | 8/2018 |
| CN | 108472138 | A | 8/2018 |
| CN | 108472395 | A | 8/2018 |
| CN | 108472424 | A | 8/2018 |
| CN | 207708246 | U | 8/2018 |
| CN | 207708250 | U | 8/2018 |
| CN | 105407937 | B | 9/2018 |
| CN | 105902298 | B | 9/2018 |
| CN | 106420113 | B | 9/2018 |
| CN | 106510902 | B | 9/2018 |
| CN | 108525039 | A | 9/2018 |
| CN | 108525040 | A | 9/2018 |
| CN | 108601653 | A | 9/2018 |
| CN | 108601872 | A | 9/2018 |
| CN | 108601874 | A | 9/2018 |
| CN | 108601875 | A | 9/2018 |
| CN | 207924984 | U | 9/2018 |
| CN | 106377810 | B | 10/2018 |
| EP | 96495 | B1 | 9/1986 |
| EP | 79373 | B1 | 12/1986 |
| EP | 54049 | B1 | 1/1988 |
| EP | 292510 | A4 | 8/1989 |
| EP | 167562 | B1 | 4/1990 |
| EP | 230532 | B1 | 9/1990 |
| EP | 241950 | B1 | 12/1990 |
| EP | 129779 | B1 | 4/1991 |
| EP | 202649 | B1 | 8/1991 |
| EP | 445782 | A1 | 9/1991 |
| EP | 464714 | A1 | 1/1992 |
| EP | 293592 | B1 | 11/1992 |
| EP | 297723 | B1 | 8/1993 |
| EP | 396575 | B1 | 3/1994 |
| EP | 397668 | B1 | 3/1994 |
| EP | 593574 | A1 | 4/1994 |
| EP | 378251 | B1 | 6/1994 |
| EP | 605621 | A1 | 7/1994 |
| EP | 467999 | B1 | 8/1994 |
| EP | 350282 | B1 | 11/1994 |
| EP | 478635 | B1 | 12/1994 |
| EP | 397720 | B1 | 3/1995 |
| EP | 421558 | B1 | 4/1995 |
| EP | 364799 | B1 | 5/1995 |
| EP | 660726 | A1 | 7/1995 |
| EP | 672386 | A1 | 9/1995 |
| EP | 349581 | B1 | 1/1996 |
| EP | 464973 | B1 | 1/1996 |
| EP | 505270 | B1 | 1/1996 |

(56) References Cited

FOREIGN PATENT DOCUMENTS

| | | | |
|---|---|---|---|
| EP | 480101 | B1 | 5/1996 |
| EP | 583781 | B1 | 5/1996 |
| EP | 583012 | B1 | 7/1996 |
| EP | 756500 | A1 | 2/1997 |
| EP | 0764448 | A2 | 3/1997 |
| EP | 767318 | A2 | 4/1997 |
| EP | 788808 | A2 | 8/1997 |
| EP | 799060 | A1 | 10/1997 |
| EP | 823567 | A1 | 2/1998 |
| EP | 832357 | A1 | 4/1998 |
| EP | 841917 | A1 | 5/1998 |
| EP | 560000 | B1 | 9/1998 |
| EP | 879012 | A1 | 11/1998 |
| EP | 925078 | A1 | 6/1999 |
| EP | 807141 | B1 | 7/1999 |
| EP | 681654 | B1 | 9/1999 |
| EP | 958066 | A1 | 11/1999 |
| EP | 964718 | A1 | 12/1999 |
| EP | 725657 | B1 | 2/2000 |
| EP | 986409 | A1 | 3/2000 |
| EP | 1007140 | A1 | 6/2000 |
| EP | 1009466 | A1 | 6/2000 |
| EP | 1027898 | A1 | 8/2000 |
| EP | 1032437 | A1 | 9/2000 |
| EP | 1045708 | A1 | 10/2000 |
| EP | 1059885 | A2 | 12/2000 |
| EP | 746712 | B1 | 10/2001 |
| EP | 1139862 | A1 | 10/2001 |
| EP | 1147317 | A1 | 10/2001 |
| EP | 1148900 | A1 | 10/2001 |
| EP | 699447 | B1 | 11/2001 |
| EP | 591896 | B1 | 2/2002 |
| EP | 731664 | B1 | 2/2002 |
| EP | 797734 | B1 | 2/2002 |
| EP | 1217954 | A1 | 7/2002 |
| EP | 1231981 | A1 | 8/2002 |
| EP | 950057 | B1 | 11/2002 |
| EP | 751769 | B1 | 1/2003 |
| EP | 1278461 | A1 | 1/2003 |
| EP | 860046 | B1 | 2/2003 |
| EP | 597881 | B2 | 3/2003 |
| EP | 732949 | B1 | 3/2003 |
| EP | 814701 | B1 | 4/2003 |
| EP | 898479 | B1 | 5/2003 |
| EP | 905379 | B1 | 5/2003 |
| EP | 655625 | B1 | 7/2003 |
| EP | 764448 | B1 | 7/2003 |
| EP | 768091 | B1 | 7/2003 |
| EP | 825888 | B1 | 12/2003 |
| EP | 1379197 | A1 | 1/2004 |
| EP | 1382366 | A1 | 1/2004 |
| EP | 868145 | B1 | 2/2004 |
| EP | 895480 | B1 | 5/2004 |
| EP | 1441777 | A2 | 8/2004 |
| EP | 916359 | B1 | 9/2004 |
| EP | 1481698 | A2 | 12/2004 |
| EP | 1482999 | A1 | 12/2004 |
| EP | 1291027 | B1 | 3/2005 |
| EP | 877633 | B1 | 7/2005 |
| EP | 611228 | B2 | 8/2005 |
| EP | 1212516 | B1 | 10/2005 |
| EP | 1597457 | A2 | 11/2005 |
| EP | 1261385 | B1 | 2/2006 |
| EP | 1648309 | A1 | 4/2006 |
| EP | 1354606 | B1 | 6/2006 |
| EP | 1663081 | A1 | 6/2006 |
| EP | 1321166 | B1 | 7/2006 |
| EP | 1191956 | B1 | 9/2006 |
| EP | 1722767 | A2 | 11/2006 |
| EP | 1070510 | B1 | 1/2007 |
| EP | 1317295 | B1 | 1/2007 |
| EP | 1327455 | B1 | 1/2007 |
| EP | 1776095 | A1 | 4/2007 |
| EP | 1141670 | B1 | 7/2007 |
| EP | 1807148 | A2 | 7/2007 |
| EP | 1827448 | A1 | 9/2007 |
| EP | 1374928 | B1 | 12/2007 |
| EP | 1877133 | A2 | 1/2008 |
| EP | 1379294 | B1 | 5/2008 |
| EP | 1930034 | A1 | 6/2008 |
| EP | 1318848 | B1 | 7/2008 |
| EP | 1356859 | B1 | 8/2008 |
| EP | 1955725 | A2 | 8/2008 |
| EP | 2058017 | A2 | 5/2009 |
| EP | 1731957 | B1 | 8/2009 |
| EP | 1173238 | B1 | 10/2009 |
| EP | 2043553 | B1 | 3/2010 |
| EP | 2158491 | A2 | 3/2010 |
| EP | 2178580 | A2 | 4/2010 |
| EP | 2182844 | A1 | 5/2010 |
| EP | 2194278 | A1 | 6/2010 |
| EP | 1471952 | B1 | 7/2010 |
| EP | 2207578 | A1 | 7/2010 |
| EP | 2216059 | A1 | 8/2010 |
| EP | 2218469 | A1 | 8/2010 |
| EP | 2219699 | A1 | 8/2010 |
| EP | 2222635 | A2 | 9/2010 |
| EP | 2222788 | A1 | 9/2010 |
| EP | 2229965 | A1 | 9/2010 |
| EP | 2235204 | A1 | 10/2010 |
| EP | 1280581 | B1 | 11/2010 |
| EP | 2246078 | A1 | 11/2010 |
| EP | 2248544 | A1 | 11/2010 |
| EP | 2252337 | A1 | 11/2010 |
| EP | 2266640 | A1 | 12/2010 |
| EP | 2269670 | A1 | 1/2011 |
| EP | 2297583 | A2 | 3/2011 |
| EP | 2298371 | A1 | 3/2011 |
| EP | 2298372 | A1 | 3/2011 |
| EP | 2298373 | A1 | 3/2011 |
| EP | 2299119 | A1 | 3/2011 |
| EP | 1464348 | B1 | 4/2011 |
| EP | 2314330 | A1 | 4/2011 |
| EP | 2314331 | A1 | 4/2011 |
| EP | 2338539 | A1 | 6/2011 |
| EP | 2338540 | A1 | 6/2011 |
| EP | 2338541 | A1 | 6/2011 |
| EP | 1654027 | B1 | 7/2011 |
| EP | 2343091 | A1 | 7/2011 |
| EP | 2347778 | A1 | 7/2011 |
| EP | 1812094 | B1 | 8/2011 |
| EP | 2349385 | A1 | 8/2011 |
| EP | 2353626 | A1 | 8/2011 |
| EP | 2356458 | A1 | 8/2011 |
| EP | 2363157 | A1 | 9/2011 |
| EP | 2366412 | A2 | 9/2011 |
| EP | 1907049 | B1 | 11/2011 |
| EP | 2388027 | A1 | 11/2011 |
| EP | 2388029 | A1 | 11/2011 |
| EP | 2399639 | A1 | 12/2011 |
| EP | 1514571 | B1 | 1/2012 |
| EP | 2407185 | A1 | 1/2012 |
| EP | 2407186 | A1 | 1/2012 |
| EP | 2407187 | A1 | 1/2012 |
| EP | 2422735 | A1 | 2/2012 |
| EP | 2322600 | B1 | 3/2012 |
| EP | 2429603 | A2 | 3/2012 |
| EP | 2459269 | A1 | 6/2012 |
| EP | 2497521 | A1 | 9/2012 |
| EP | 2140892 | B1 | 10/2012 |
| EP | 2505228 | A1 | 10/2012 |
| EP | 2150811 | B1 | 1/2013 |
| EP | 1833529 | B1 | 2/2013 |
| EP | 2554191 | A1 | 2/2013 |
| EP | 2277463 | B1 | 3/2013 |
| EP | 2564771 | A1 | 3/2013 |
| EP | 2151257 | B1 | 4/2013 |
| EP | 2575922 | A2 | 4/2013 |
| EP | 1623730 | B1 | 5/2013 |
| EP | 2606919 | A1 | 6/2013 |
| EP | 2606920 | A1 | 6/2013 |
| EP | 2607712 | A1 | 6/2013 |
| EP | 1919550 | B1 | 7/2013 |
| EP | 2620173 | A1 | 7/2013 |

(56)          References Cited

FOREIGN PATENT DOCUMENTS

| | | | |
|---|---|---|---|
| EP | 1331017 | B1 | 8/2013 |
| EP | 2101840 | B1 | 9/2013 |
| EP | 2401003 | B1 | 10/2013 |
| EP | 2654878 | A2 | 10/2013 |
| EP | 2654883 | A2 | 10/2013 |
| EP | 2671083 | A1 | 12/2013 |
| EP | 1412001 | B1 | 1/2014 |
| EP | 1942965 | B1 | 1/2014 |
| EP | 2231222 | B1 | 2/2014 |
| EP | 2697890 | A2 | 2/2014 |
| EP | 1017433 | B1 | 3/2014 |
| EP | 1629855 | B1 | 4/2014 |
| EP | 2736581 | A2 | 6/2014 |
| EP | 2744460 | A1 | 6/2014 |
| EP | 2745869 | A1 | 6/2014 |
| EP | 1485613 | B1 | 7/2014 |
| EP | 1605988 | B1 | 8/2014 |
| EP | 2792696 | A2 | 10/2014 |
| EP | 2195043 | B1 | 12/2014 |
| EP | 1962949 | B1 | 2/2015 |
| EP | 2030641 | B1 | 2/2015 |
| EP | 2643927 | B1 | 4/2015 |
| EP | 2868331 | A2 | 5/2015 |
| EP | 1460972 | B1 | 6/2015 |
| EP | 2150569 | B1 | 6/2015 |
| EP | 2152783 | B1 | 6/2015 |
| EP | 2345439 | B1 | 6/2015 |
| EP | 2895215 | A2 | 7/2015 |
| EP | 1761306 | B1 | 8/2015 |
| EP | 2663347 | B1 | 8/2015 |
| EP | 2209508 | B1 | 9/2015 |
| EP | 2915129 | A1 | 9/2015 |
| EP | 2920421 | A2 | 9/2015 |
| EP | 2533732 | B1 | 11/2015 |
| EP | 1317305 | B1 | 12/2015 |
| EP | 1339443 | B1 | 1/2016 |
| EP | 2967284 | A1 | 1/2016 |
| EP | 2967547 | A1 | 1/2016 |
| EP | 2984731 | A1 | 2/2016 |
| EP | 2167158 | B1 | 3/2016 |
| EP | 2061531 | B1 | 4/2016 |
| EP | 2519274 | B1 | 4/2016 |
| EP | 1996252 | B1 | 5/2016 |
| EP | 2464395 | B1 | 5/2016 |
| EP | 3047873 | A1 | 7/2016 |
| EP | 3047911 | A1 | 7/2016 |
| EP | 2643053 | B1 | 8/2016 |
| EP | 2734251 | B1 | 8/2016 |
| EP | 3050537 | A1 | 8/2016 |
| EP | 1942128 | B1 | 9/2016 |
| EP | 2099509 | B1 | 9/2016 |
| EP | 2719403 | B1 | 9/2016 |
| EP | 3072210 | A1 | 9/2016 |
| EP | 3072211 | A1 | 9/2016 |
| EP | 2405140 | B1 | 10/2016 |
| EP | 2197507 | B1 | 11/2016 |
| EP | 2538086 | B1 | 11/2016 |
| EP | 3086834 | A1 | 11/2016 |
| EP | 2806911 | B1 | 12/2016 |
| EP | 3110468 | A1 | 1/2017 |
| EP | 3113808 | A1 | 1/2017 |
| EP | 3119452 | A1 | 1/2017 |
| EP | 3120811 | A2 | 1/2017 |
| EP | 3131595 | A1 | 2/2017 |
| EP | 3131596 | A1 | 2/2017 |
| EP | 3131599 | A1 | 2/2017 |
| EP | 3131600 | A1 | 2/2017 |
| EP | 3131615 | A1 | 2/2017 |
| EP | 2585129 | B1 | 3/2017 |
| EP | 2594799 | B1 | 3/2017 |
| EP | 3146987 | A1 | 3/2017 |
| EP | 3153190 | A1 | 4/2017 |
| EP | 3157597 | A1 | 4/2017 |
| EP | 3173110 | A1 | 5/2017 |
| EP | 2825107 | B1 | 7/2017 |
| EP | 3185924 | A1 | 7/2017 |
| EP | 3185925 | A1 | 7/2017 |
| EP | 3189526 | A1 | 7/2017 |
| EP | 3191164 | A1 | 7/2017 |
| EP | 2618001 | B1 | 8/2017 |
| EP | 3197602 | A1 | 8/2017 |
| EP | 3198677 | A1 | 8/2017 |
| EP | 3204989 | A1 | 8/2017 |
| EP | 3212250 | A1 | 9/2017 |
| EP | 3219339 | A1 | 9/2017 |
| EP | 3223880 | A1 | 10/2017 |
| EP | 3232948 | A1 | 10/2017 |
| EP | 1885409 | B1 | 11/2017 |
| EP | 2292282 | B1 | 11/2017 |
| EP | 2945661 | B1 | 11/2017 |
| EP | 3238764 | A1 | 11/2017 |
| EP | 3244814 | A1 | 11/2017 |
| EP | 3247420 | A1 | 11/2017 |
| EP | 3247421 | A2 | 11/2017 |
| EP | 3248628 | A1 | 11/2017 |
| EP | 2136613 | B1 | 12/2017 |
| EP | 3256183 | A1 | 12/2017 |
| EP | 3256184 | A1 | 12/2017 |
| EP | 3256185 | A1 | 12/2017 |
| EP | 3256186 | A1 | 12/2017 |
| EP | 3007742 | B1 | 1/2018 |
| EP | 3277200 | A1 | 2/2018 |
| EP | 3287155 | A1 | 2/2018 |
| EP | 2482916 | B1 | 3/2018 |
| EP | 2948202 | B1 | 3/2018 |
| EP | 3294367 | A1 | 3/2018 |
| EP | 2945662 | B1 | 4/2018 |
| EP | 3310409 | A1 | 4/2018 |
| EP | 3222301 | B1 | 5/2018 |
| EP | 3222302 | B1 | 5/2018 |
| EP | 3313471 | A1 | 5/2018 |
| EP | 3324840 | A1 | 5/2018 |
| EP | 3325035 | A1 | 5/2018 |
| EP | 3326487 | A1 | 5/2018 |
| EP | 1789129 | B1 | 6/2018 |
| EP | 1990358 | B1 | 6/2018 |
| EP | 3329953 | A1 | 6/2018 |
| EP | 3335647 | A2 | 6/2018 |
| EP | 3341069 | A1 | 7/2018 |
| EP | 3349839 | A1 | 7/2018 |
| EP | 2219698 | B1 | 8/2018 |
| EP | 2890420 | B1 | 8/2018 |
| EP | 3352808 | A1 | 8/2018 |
| EP | 3352835 | A1 | 8/2018 |
| EP | 3360233 | A1 | 8/2018 |
| EP | 3360515 | A1 | 8/2018 |
| EP | 1534381 | B1 | 9/2018 |
| EP | 3108909 | B1 | 9/2018 |
| EP | 3377001 | A1 | 9/2018 |
| EP | 3377002 | A1 | 9/2018 |
| EP | 3377134 | A1 | 9/2018 |
| EP | 3377135 | A1 | 9/2018 |
| EP | 3377136 | A1 | 9/2018 |
| EP | 2249746 | B1 | 10/2018 |
| EP | 2988795 | B1 | 10/2018 |
| EP | 3383300 | A1 | 10/2018 |
| EP | 3383448 | A1 | 10/2018 |
| EP | 3388005 | A1 | 10/2018 |
| EP | 3542835 | A1 | 9/2019 |
| FR | 2331995 | A2 | 6/1977 |
| JP | 64-52472 | A | 2/1989 |
| JP | 02289241 | A | 11/1990 |
| JP | 04176471 | A | 6/1992 |
| JP | 04224760 | A | 8/1992 |
| JP | H05-078996 | U | 10/1993 |
| JP | H11-062856 | A | 3/1999 |
| JP | 02888609 | B2 | 5/1999 |
| JP | 02927460 | B2 | 7/1999 |
| JP | H11-244376 | A | 9/1999 |
| JP | 2000102604 | A | 4/2000 |
| JP | 2000107281 | A | 4/2000 |
| JP | 2000283062 | A | 10/2000 |
| JP | 03131696 | B2 | 2/2001 |
| JP | 2001061957 | A | 3/2001 |

US 12,599,758 B2

Page 14

(56) References Cited

FOREIGN PATENT DOCUMENTS

| JP | 2001090687 | A | 4/2001 |
|----|------------|---|--------|
| JP | 03174338 | B2 | 6/2001 |
| JP | 2001173402 | A | 6/2001 |
| JP | 2001523983 | A | 11/2001 |
| JP | 03278160 | B2 | 4/2002 |
| JP | 2002191123 | A | 7/2002 |
| JP | 03313061 | B2 | 8/2002 |
| JP | 2003047656 | A | 2/2003 |
| JP | 2003070906 | A | 3/2003 |
| JP | 2003205030 | A | 7/2003 |
| JP | 2004011525 | A | 1/2004 |
| JP | 2004016426 | A | 1/2004 |
| JP | 2004028102 | A | 1/2004 |
| JP | 2004073400 | A | 3/2004 |
| JP | 2004209240 | A | 7/2004 |
| JP | 2004278375 | A | 10/2004 |
| JP | 03612581 | B2 | 1/2005 |
| JP | 2005058617 | A | 3/2005 |
| JP | 2005192687 | A | 7/2005 |
| JP | 2005199076 | A | 7/2005 |
| JP | 2005348996 | A | 12/2005 |
| JP | 2006000631 | A | 1/2006 |
| JP | 03786289 | B2 | 6/2006 |
| JP | 03803417 | B2 | 8/2006 |
| JP | 2006280571 | A | 10/2006 |
| JP | 03854972 | B2 | 12/2006 |
| JP | 2007044302 | A | 2/2007 |
| JP | 2007075541 | A | 3/2007 |
| JP | 2007089607 | A | 4/2007 |
| JP | 2007089973 | A | 4/2007 |
| JP | 2007222670 | A | 9/2007 |
| JP | 2007236564 | A | 9/2007 |
| JP | 04016441 | B2 | 12/2007 |
| JP | 04022372 | B2 | 12/2007 |
| JP | 2008018242 | A | 1/2008 |
| JP | 04051812 | B2 | 2/2008 |
| JP | 04072721 | B2 | 4/2008 |
| JP | 04077902 | B2 | 4/2008 |
| JP | 04078245 | B2 | 4/2008 |
| JP | 04084060 | B2 | 4/2008 |
| JP | 04086185 | B2 | 5/2008 |
| JP | 04108054 | B2 | 6/2008 |
| JP | 04121709 | B2 | 7/2008 |
| JP | 04163384 | B2 | 10/2008 |
| JP | 04179634 | B2 | 11/2008 |
| JP | 2008264586 | A | 11/2008 |
| JP | 04198986 | B2 | 12/2008 |
| JP | 04209412 | B2 | 1/2009 |
| JP | 2009090882 | A | 4/2009 |
| JP | 04279494 | B2 | 6/2009 |
| JP | 04308723 | B2 | 8/2009 |
| JP | 2009178570 | A | 8/2009 |
| JP | 2009254436 | A | 11/2009 |
| JP | 2009273214 | A | 11/2009 |
| JP | 04387106 | B2 | 12/2009 |
| JP | 04391680 | B2 | 12/2009 |
| JP | 04414925 | B2 | 2/2010 |
| JP | 04440499 | B2 | 3/2010 |
| JP | 04467187 | B2 | 5/2010 |
| JP | 04468965 | B2 | 5/2010 |
| JP | 04484320 | B2 | 6/2010 |
| JP | 04512150 | B2 | 7/2010 |
| JP | 2010158532 | A | 7/2010 |
| JP | 04523961 | B2 | 8/2010 |
| JP | 04523962 | B2 | 8/2010 |
| JP | 04548450 | B2 | 9/2010 |
| JP | 04549407 | B2 | 9/2010 |
| JP | 2010246941 | A | 11/2010 |
| JP | 04611364 | B2 | 1/2011 |
| JP | 04611365 | B2 | 1/2011 |
| JP | 04646393 | B2 | 3/2011 |
| JP | 04655231 | B2 | 3/2011 |
| JP | 04656332 | B2 | 3/2011 |
| JP | 04674978 | B2 | 4/2011 |
| JP | 2011072533 | A | 4/2011 |
| JP | 2011116765 | A | 6/2011 |
| JP | 04728351 | B2 | 7/2011 |
| JP | 04741242 | B2 | 8/2011 |
| JP | 04741489 | B2 | 8/2011 |
| JP | 2011161401 | A | 8/2011 |
| JP | 04795536 | B2 | 10/2011 |
| JP | 04851333 | B2 | 1/2012 |
| JP | 04865825 | B2 | 2/2012 |
| JP | 04881154 | B2 | 2/2012 |
| JP | 04897811 | B2 | 3/2012 |
| JP | 04907028 | B2 | 3/2012 |
| JP | 04908737 | B2 | 4/2012 |
| JP | 04964854 | B2 | 7/2012 |
| JP | 04987999 | B2 | 8/2012 |
| JP | 05047447 | B2 | 10/2012 |
| JP | 05048749 | B2 | 10/2012 |
| JP | 05093869 | B2 | 12/2012 |
| JP | 05102033 | B2 | 12/2012 |
| JP | 05164558 | B2 | 3/2013 |
| JP | 05185629 | B2 | 4/2013 |
| JP | 05193059 | B2 | 5/2013 |
| JP | 05197636 | B2 | 5/2013 |
| JP | 2013078564 | A | 5/2013 |
| JP | 05215580 | B2 | 6/2013 |
| JP | 05267227 | B2 | 8/2013 |
| JP | 05286268 | B2 | 9/2013 |
| JP | 2013192711 | A | 9/2013 |
| JP | 2014004303 | A | 1/2014 |
| JP | 05427620 | B2 | 2/2014 |
| JP | 05429714 | B2 | 2/2014 |
| JP | 05440528 | B2 | 3/2014 |
| JP | 05440529 | B2 | 3/2014 |
| JP | 05461710 | B2 | 4/2014 |
| JP | 05500348 | B2 | 5/2014 |
| JP | 2014091049 | A | 5/2014 |
| JP | 2014114784 | A | 6/2014 |
| JP | 05539484 | B2 | 7/2014 |
| JP | 05557175 | B2 | 7/2014 |
| JP | 05590213 | B2 | 9/2014 |
| JP | 05596974 | B2 | 10/2014 |
| JP | 05611948 | B2 | 10/2014 |
| JP | 05633512 | B2 | 12/2014 |
| JP | 05656835 | B2 | 1/2015 |
| JP | 05673795 | B2 | 2/2015 |
| JP | 05675786 | B2 | 2/2015 |
| JP | 05676118 | B2 | 2/2015 |
| JP | 05701848 | B2 | 4/2015 |
| JP | 05711245 | B2 | 4/2015 |
| JP | 05750492 | B2 | 7/2015 |
| JP | 05781597 | B2 | 9/2015 |
| JP | 2015159947 | A | 9/2015 |
| JP | 05837162 | B2 | 12/2015 |
| JP | 05868180 | B2 | 2/2016 |
| JP | 05894116 | B2 | 3/2016 |
| JP | 05894678 | B2 | 3/2016 |
| JP | 2016028764 | A | 3/2016 |
| JP | 2016182342 | A | 10/2016 |
| JP | 06034858 | B2 | 11/2016 |
| JP | 06038018 | B2 | 12/2016 |
| JP | 06054106 | B2 | 12/2016 |
| JP | 2016202553 | A | 12/2016 |
| JP | 06083929 | B2 | 2/2017 |
| JP | 2017035323 | A | 2/2017 |
| JP | 2017517306 | A | 6/2017 |
| JP | 2017127675 | A | 7/2017 |
| JP | 06178666 | B2 | 8/2017 |
| JP | 2017159083 | A | 9/2017 |
| JP | 06220867 | B2 | 10/2017 |
| JP | 06236451 | B2 | 11/2017 |
| JP | 06267625 | B2 | 1/2018 |
| JP | 2018020199 | A | 2/2018 |
| JP | 06295204 | B2 | 3/2018 |
| JP | 06329358 | B2 | 5/2018 |
| JP | 06339371 | B2 | 6/2018 |
| JP | 06345112 | B2 | 6/2018 |
| JP | 06353787 | B2 | 7/2018 |
| JP | 06382285 | B2 | 8/2018 |
| JP | 2018122146 | A | 8/2018 |
| JP | 2018523541 | A | 8/2018 |

(56) References Cited

FOREIGN PATENT DOCUMENTS

| | | |
|---|---|---|
| WO | WO87/002894 A2 | 5/1987 |
| WO | WO88/009874 A1 | 12/1988 |
| WO | WO92/002263 A1 | 2/1992 |
| WO | WO92/003181 A1 | 3/1992 |
| WO | WO96/14027 A1 | 5/1995 |
| WO | WO95/031196 A1 | 11/1995 |
| WO | WO96/016684 A1 | 6/1996 |
| WO | WO98/042984 A1 | 10/1998 |
| WO | WO00/019097 A1 | 4/2000 |
| WO | WO00/027446 A1 | 5/2000 |
| WO | WO00/035515 A1 | 6/2000 |
| WO | WO01/017581 A2 | 3/2001 |
| WO | WO01/019444 A1 | 3/2001 |
| WO | WO01/041070 A1 | 6/2001 |
| WO | WO01/074419 A1 | 10/2001 |
| WO | WO01/087176 A1 | 11/2001 |
| WO | WO01/095813 A1 | 12/2001 |
| WO | WO02/47751 A2 | 6/2002 |
| WO | WO02/053226 A2 | 7/2002 |
| WO | WO02/070039 A2 | 9/2002 |
| WO | WO02/072000 A1 | 9/2002 |
| WO | WO02/081021 A1 | 10/2002 |
| WO | WO03/024501 A2 | 3/2003 |
| WO | WO03/061727 A2 | 7/2003 |
| WO | WO03/094716 A1 | 11/2003 |
| WO | WO03/103745 A2 | 12/2003 |
| WO | WO2004/026394 A1 | 4/2004 |
| WO | WO2004/034034 A1 | 4/2004 |
| WO | WO2004/088480 A2 | 10/2004 |
| WO | WO2004/098677 A1 | 11/2004 |
| WO | WO2005/020848 A2 | 3/2005 |
| WO | WO2005/033671 A1 | 4/2005 |
| WO | WO2005/037348 A1 | 4/2005 |
| WO | WO2005/054680 A1 | 6/2005 |
| WO | WO2005/108796 A1 | 11/2005 |
| WO | WO2006/040252 A1 | 4/2006 |
| WO | WO2006/053384 A1 | 5/2006 |
| WO | WO2006/081255 A2 | 8/2006 |
| WO | WO2006/121698 A2 | 11/2006 |
| WO | WO2007/008907 A2 | 1/2007 |
| WO | WO2007/033933 A1 | 3/2007 |
| WO | WO2007/053881 A1 | 5/2007 |
| WO | WO2007/065408 A2 | 6/2007 |
| WO | WO2007/092494 A2 | 8/2007 |
| WO | WO2007/105842 A1 | 9/2007 |
| WO | WO2007/146231 A2 | 12/2007 |
| WO | WO2008/005747 A2 | 1/2008 |
| WO | WO2008/008427 A2 | 1/2008 |
| WO | WO2008/088874 A2 | 7/2008 |
| WO | WO2008/102015 A1 | 8/2008 |
| WO | WO2008/121143 A1 | 10/2008 |
| WO | WO2008/121145 A1 | 10/2008 |
| WO | WO2008/137237 A2 | 11/2008 |
| WO | WO2008/140034 A1 | 11/2008 |
| WO | WO2009/017549 A1 | 2/2009 |
| WO | WO2009035581 A1 | 3/2009 |
| WO | WO2009/046789 A1 | 4/2009 |
| WO | WO2009/075668 A2 | 6/2009 |
| WO | WO2009/096991 A1 | 8/2009 |
| WO | WO2010/025411 A2 | 3/2010 |
| WO | WO2010/119110 A1 | 10/2010 |
| WO | WO2011/003043 A1 | 1/2011 |
| WO | WO2011/024928 A1 | 3/2011 |
| WO | WO2011/035925 A1 | 3/2011 |
| WO | WO2011/039091 A1 | 4/2011 |
| WO | WO2011/081629 A1 | 7/2011 |
| WO | WO2011/082212 A1 | 7/2011 |
| WO | WO2011/085040 A1 | 7/2011 |
| WO | WO2011/117566 A1 | 9/2011 |
| WO | WO2011/119060 A2 | 9/2011 |
| WO | WO2012/037506 A2 | 3/2012 |
| WO | WO2012/051454 A2 | 4/2012 |
| WO | WO2012/064674 A1 | 5/2012 |
| WO | WO2012/075152 A1 | 6/2012 |
| WO | WO2012/075262 A1 | 6/2012 |
| WO | WO2012/087811 A2 | 6/2012 |
| WO | WO2012/094535 A2 | 7/2012 |
| WO | WO2012/094641 A2 | 7/2012 |
| WO | WO2012/096716 A2 | 7/2012 |
| WO | WO2012/112129 A1 | 8/2012 |
| WO | WO2013/034547 A1 | 3/2013 |
| WO | WO2013/093058 A1 | 6/2013 |
| WO | WO2013/127182 A1 | 9/2013 |
| WO | WO2013/134319 A1 | 9/2013 |
| WO | WO2013/148560 A1 | 10/2013 |
| WO | WO2013/148697 A1 | 10/2013 |
| WO | WO2014/070458 A1 | 5/2014 |
| WO | WO2014/096408 A1 | 6/2014 |
| WO | WO2014/106635 A1 | 7/2014 |
| WO | WO2014/116639 A1 | 7/2014 |
| WO | WO2014/142754 A1 | 9/2014 |
| WO | WO2014/143593 A1 | 9/2014 |
| WO | WO2014/164136 A1 | 10/2014 |
| WO | WO2014/164292 A1 | 10/2014 |
| WO | WO2014/166128 A1 | 10/2014 |
| WO | WO2014/169023 A2 | 10/2014 |
| WO | WO2015/119705 A1 | 8/2015 |
| WO | WO2015/160943 A1 | 10/2015 |
| WO | WO2015/160979 A1 | 10/2015 |
| WO | WO2015/171156 A1 | 11/2015 |
| WO | WO2015/175711 A1 | 11/2015 |
| WO | WO2015/175718 A1 | 11/2015 |
| WO | WO2015/177793 A2 | 11/2015 |
| WO | WO2015/187659 A2 | 12/2015 |
| WO | WO2016/100600 A2 | 6/2016 |
| WO | WO2016/113266 A1 | 7/2016 |
| WO | WO2016/116630 A2 | 7/2016 |
| WO | WO2017/001358 A1 | 1/2017 |
| WO | WO2017/011257 A1 | 1/2017 |
| WO | WO2017/032751 A1 | 3/2017 |
| WO | WO2017/048733 A1 | 3/2017 |
| WO | WO2017/060254 A1 | 4/2017 |
| WO | WO2017/060257 A1 | 4/2017 |
| WO | WO2017/075322 A1 | 5/2017 |
| WO | WO2017/087380 A1 | 5/2017 |
| WO | WO2017/120453 A1 | 7/2017 |
| WO | WO2017/133425 A1 | 8/2017 |
| WO | WO2017/134657 A1 | 8/2017 |
| WO | WO2017/139113 A1 | 8/2017 |
| WO | WO2017/139246 A1 | 8/2017 |
| WO | WO2017/147082 A1 | 8/2017 |
| WO | WO2017/147103 A1 | 8/2017 |
| WO | WO2017/147291 A1 | 8/2017 |
| WO | WO2017/151987 A1 | 9/2017 |
| WO | WO2017/156386 A1 | 9/2017 |
| WO | WO2017/159849 A1 | 9/2017 |
| WO | WO2017/165372 A1 | 9/2017 |
| WO | WO2017/178904 A1 | 10/2017 |
| WO | WO2017/183124 A1 | 10/2017 |
| WO | WO2017/190155 A2 | 11/2017 |
| WO | WO2017/192119 A1 | 11/2017 |
| WO | WO2017/196271 A1 | 11/2017 |
| WO | WO2017/205909 A1 | 12/2017 |
| WO | WO2017/210318 A2 | 12/2017 |
| WO | WO2017/214118 A1 | 12/2017 |
| WO | WO2017/214183 A1 | 12/2017 |
| WO | WO2017/217946 A2 | 12/2017 |
| WO | WO2018/007120 A1 | 1/2018 |
| WO | WO2018/007471 A1 | 1/2018 |
| WO | WO2018/017678 A1 | 1/2018 |
| WO | WO2018/017683 A1 | 1/2018 |
| WO | WO2018/017716 A1 | 1/2018 |
| WO | WO2018/026764 A1 | 2/2018 |
| WO | WO2018/026769 A1 | 2/2018 |
| WO | WO2018/031741 A1 | 2/2018 |
| WO | WO2018/035069 A1 | 2/2018 |
| WO | WO2018/039124 A1 | 3/2018 |
| WO | WO2018/039326 A1 | 3/2018 |
| WO | WO2018/041963 A1 | 3/2018 |
| WO | WO2018/045299 A1 | 3/2018 |
| WO | WO2018/051091 A1 | 3/2018 |
| WO | WO2018/052482 A1 | 3/2018 |
| WO | WO2018/057482 A1 | 3/2018 |
| WO | WO2018/057563 A1 | 3/2018 |

(56) References Cited

FOREIGN PATENT DOCUMENTS

| | | |
|---|---|---|
| WO | WO2018/061002 A1 | 4/2018 |
| WO | WO2018/064437 A1 | 4/2018 |
| WO | WO2018/067410 A1 | 4/2018 |
| WO | WO2018/073150 A1 | 4/2018 |
| WO | WO2018/078370 A1 | 5/2018 |
| WO | WO2018/078615 A1 | 5/2018 |
| WO | WO2018/082987 A1 | 5/2018 |
| WO | WO2018/088939 A1 | 5/2018 |
| WO | WO2018/089970 A1 | 5/2018 |
| WO | WO2018/093663 A1 | 5/2018 |
| WO | WO2018/096531 A1 | 5/2018 |
| WO | WO2018/118756 A1 | 6/2018 |
| WO | WO2018/132181 A1 | 7/2018 |
| WO | WO2018/132182 A1 | 7/2018 |
| WO | WO2018/135477 A1 | 7/2018 |
| WO | WO2018/135478 A1 | 7/2018 |
| WO | WO2018/136592 A2 | 7/2018 |
| WO | WO2018/139508 A1 | 8/2018 |
| WO | WO2018/145434 A1 | 8/2018 |
| WO | WO2018/146045 A1 | 8/2018 |
| WO | WO2018/146170 A1 | 8/2018 |
| WO | WO2018/146173 A1 | 8/2018 |
| WO | WO2018/146177 A1 | 8/2018 |
| WO | WO2018/148456 A1 | 8/2018 |
| WO | WO2018/156524 A1 | 8/2018 |
| WO | WO2018/158636 A1 | 9/2018 |
| WO | WO2018/177344 A1 | 10/2018 |
| WO | WO2018/178939 A1 | 10/2018 |
| WO | WO2018/183128 A1 | 10/2018 |
| WO | WO2018/187576 A2 | 10/2018 |
| WO | WO2018/226991 A1 | 12/2018 |
| WO | WO2019/094963 A1 | 5/2019 |
| WO | WO2019/138350 A2 | 7/2019 |
| WO | WO2019/158996 A1 | 8/2019 |
| WO | WO2019/191851 A1 | 9/2019 |
| WO | WO2019/194956 A1 | 10/2019 |
| WO | WO2019/229222 A1 | 12/2019 |
| WO | WO2020/028537 A1 | 2/2020 |
| WO | WO2020/0234785 A1 | 11/2020 |
| WO | WO2021/026469 A1 | 2/2021 |
| WO | WO2021/026472 A1 | 2/2021 |
| WO | WO2021/062260 A1 | 4/2021 |
| WO | WO2021/062265 A1 | 4/2021 |
| WO | WO2021/062270 A1 | 4/2021 |
| WO | WO2021/119478 A1 | 6/2021 |
| WO | WO2021/127503 A1 | 6/2021 |
| WO | WO2021/158967 A1 | 8/2021 |
| WO | WO2021/195617 A1 | 9/2021 |
| WO | WO2021/222403 A1 | 11/2021 |
| WO | WO2021/231574 A1 | 11/2021 |
| WO | WO2021/243263 A1 | 12/2021 |
| WO | WO2022/072944 A1 | 4/2022 |
| WO | WO2022/076862 A1 | 4/2022 |
| WO | WO2022/076948 A1 | 4/2022 |
| WO | WO2022/120270 A1 | 6/2022 |

OTHER PUBLICATIONS

Calomeni et al.; U.S. Appl. No. 18/614,131 entitled "Intravascular blood pumps and methods of manufacture and use," filed Mar. 22, 2024.

Brandt et al.; U.S. Appl. No. 18/554,756 entitled "Catheter blood pump shrouds and assembly thereof," filed Oct. 10, 2023.

Ryan et al.; U.S. Appl. No. 18/559,231 entitled "Intravascular blood pump outflow flow disruptor," filed Nov. 6, 2023.

Salahieh et al.; U.S. Appl. No. 18/615,896 entitled "Intravascular blood pumps and methods of use and manufacture," filed Mar. 25, 2024.

Varghai et al.; U.S. Appl. No. 18/711,528 entitled "Intravascular blood pumps, motors, and fluid control," filed May 17, 2024.

Hildebrand; U.S. Appl. No. 18/710,551 entitled "Intravascular blood pumps and expandable scaffolds with stiffening members" filed May 15, 2024.

Salahieh et al.; U.S. Appl. No. 18/047,076 entitled "Intravascular fluid movement devices, systems, and methods of use," filed Oct. 17, 2022.

Merchant et al.; U.S. Appl. No. 17/997,489 entitled "Intravascular blood pumps and control thereof," filed Oct. 28, 2022.

Saul et al.; U.S. Appl. No. 17/998,614 entitled "Inflatable medical devices, methods of manufacture and use," filed Nov. 11, 2022.

Ryan et al.; U.S. Appl. No. 17/998,624 entitled "Catheter blood pumps and collapsible pump housings," filed Nov. 11, 2022.

Varghai et al.; U.S. Appl. No. 18/000,265 entitled "Intravascular blood pumps," filed Nov. 29, 2022.

Jagani et al.; Dual-propeller cavopulmonary pump for assisting patients with hypoplastic right ventricle; ASAIO Journal (American Society for Artificial Internal Organs); 10 pages; DOI: 10.1097/MAT.0000000000000907; Jan. 2019.

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.

Reitan et al.; First human use of the reitan catheter pump; Asaio Journal; 47(2); p. 124; Mar.-Apr. 2001.

Gupta et al.; U.S. Appl. No. 29/761,852 entitled "Intravascular blood pump external display screen or a portion thereof with graphical user interface," filed Dec. 11, 2020.

Hildebrand et al.; U.S. Appl. No. 17/632,550 entitled Catheter blood pumps and impellers, filed Feb. 3, 2022.

Robinson et al.; U.S. Appl. No. 17/784,758 Descending aorta and vena cava blood pumps, filed Jun. 13, 2022.

* cited by examiner

*1342*   *1340*   *1330*   *1336*   *1332*   *1338*   *1334*

DC Motor

← different pitch than →

DC Motor

DC Motor

Axillary Artery

*152* ascending aorta blood outflow

*155*

*151* aortic valve

*154*

*152* left ventricle

*150*

*154*

*152*

$L_P$ $L_{SP}$

*340*

$L_{SD}$

*345*  *353*  *341*  *349*     *356*     *347*

$D_I$

*361*
*348*  *343*     *346*     *350*  *344*     *352*

$D_P$ $L_C$

P      60      D

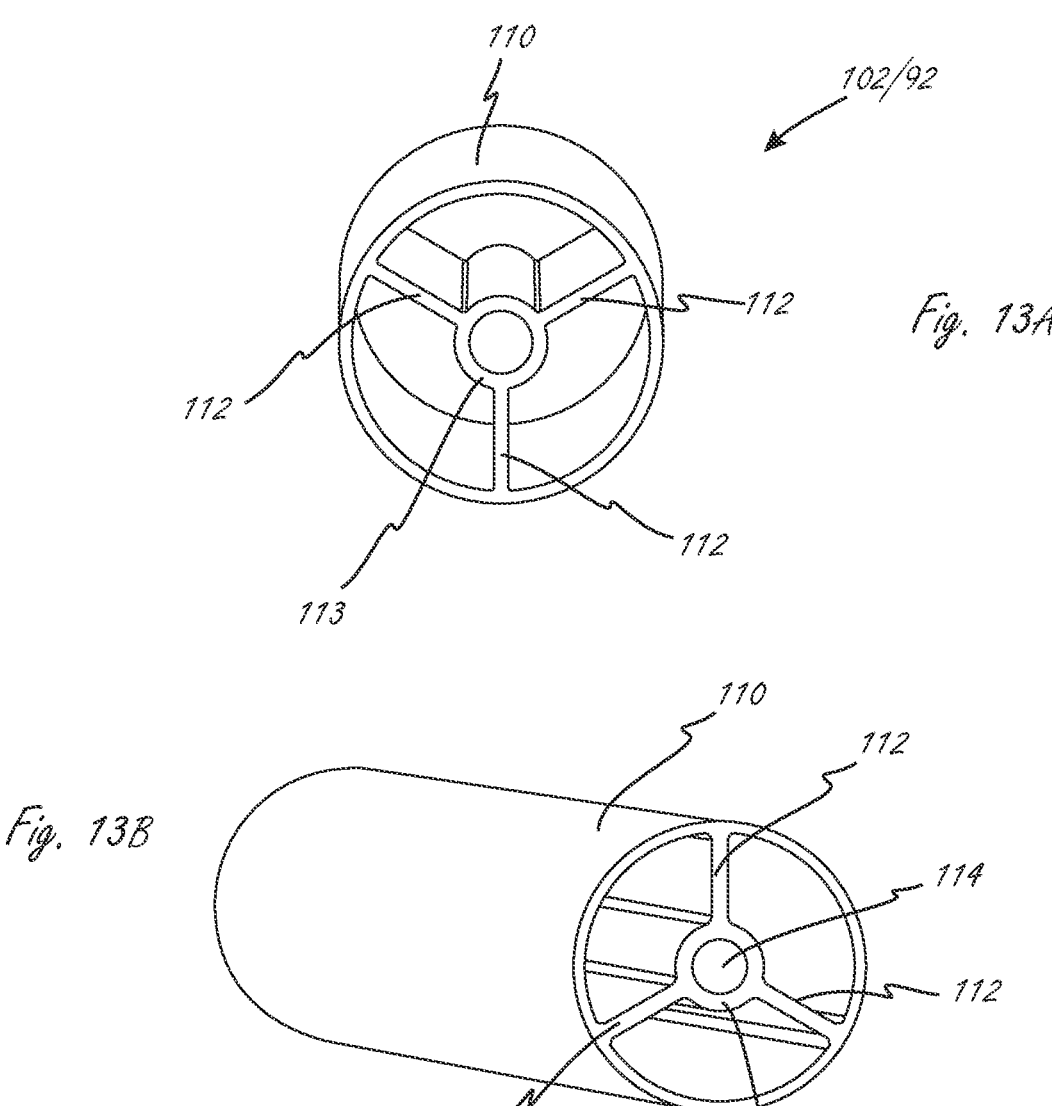
Fig. 13A
Fig. 13B
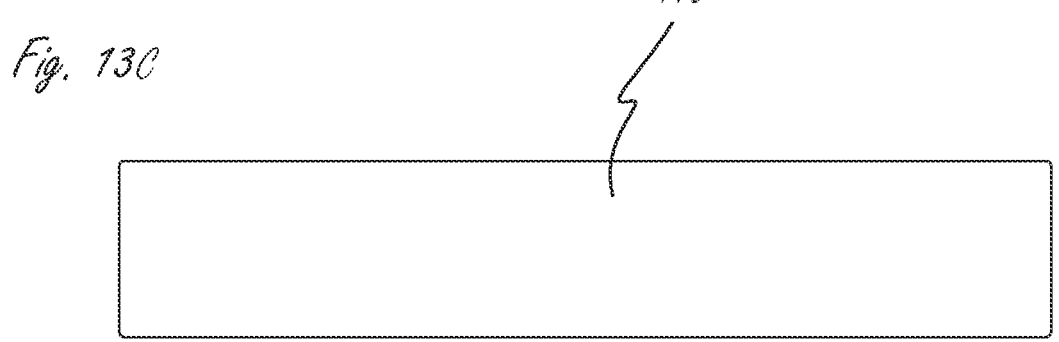
Fig. 13C

*130*

*142*

*143*

*140*

*141*

Purge Inlet Port

*737*

*311*

*133*

*139*

*137*  *135*

*137*

*132*

*134*

*136*

GW & Purge
Outlet Port

Motor

Rotary Lip Seal

*138*

Drive Cable Tube Junction / Optional Alignment Bearing Housing

RO Marker Band

Proximal Bearing Assembly (Alignment and Thrust Bearings on shaft and in Distal Catheter Cap)

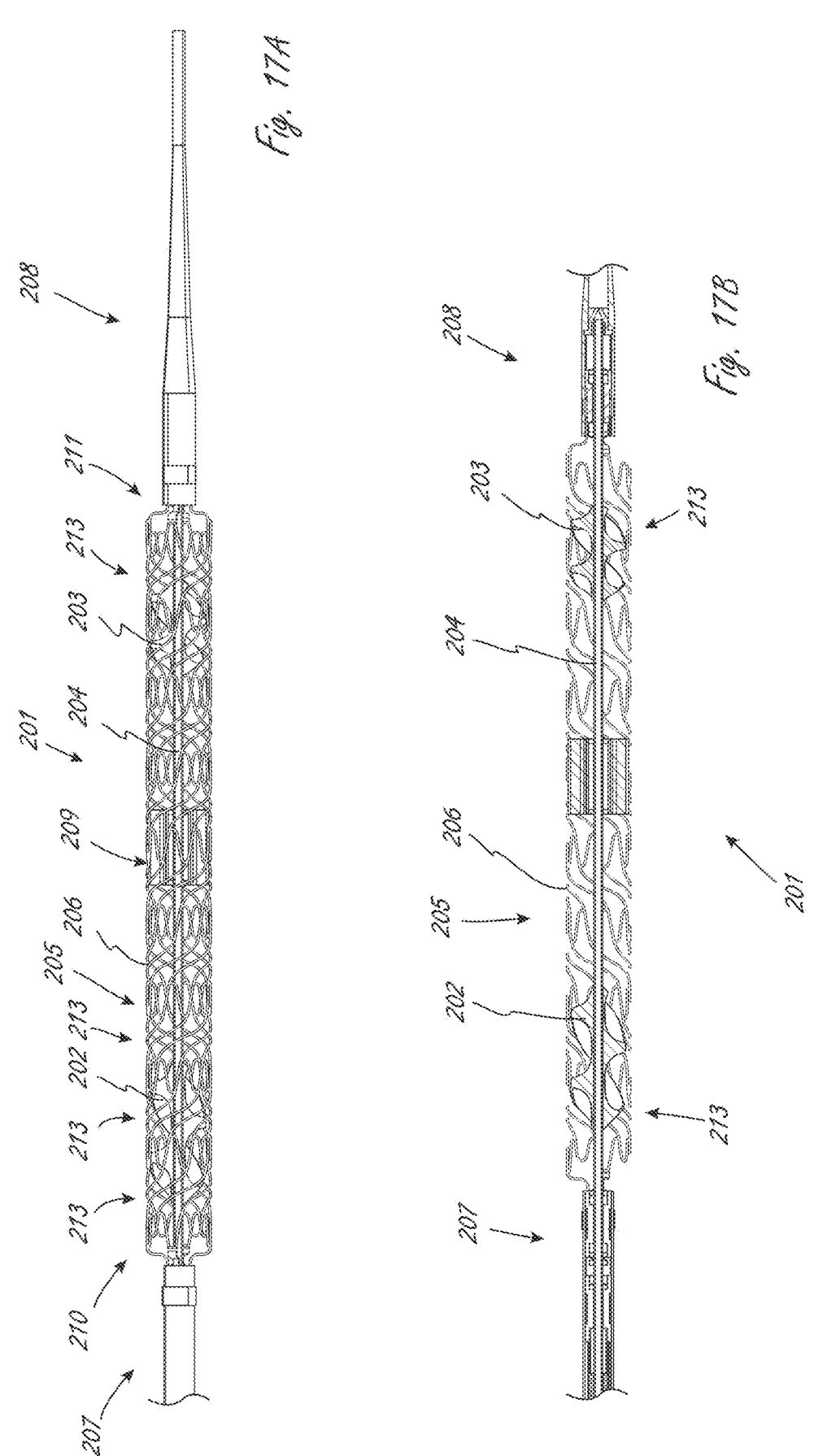

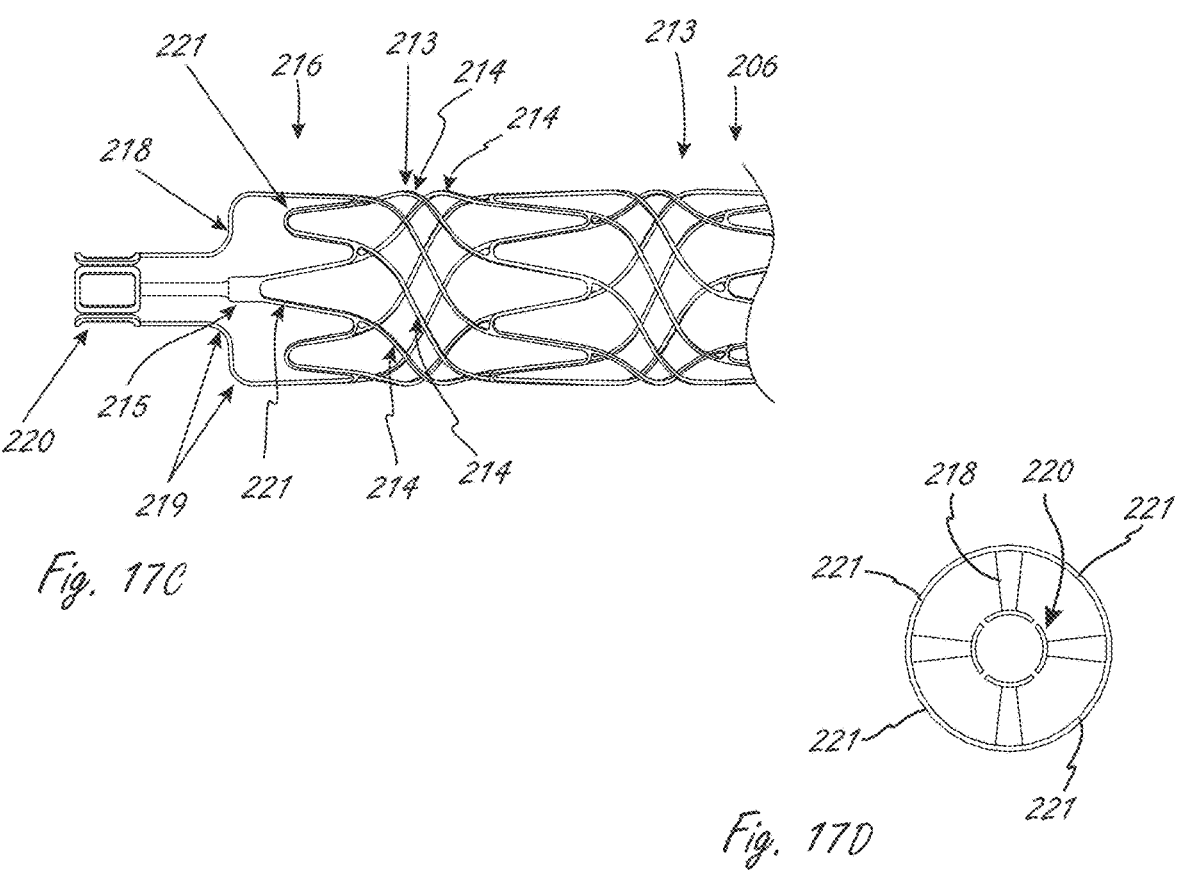
*Fig. 17C*
*Fig. 17D*
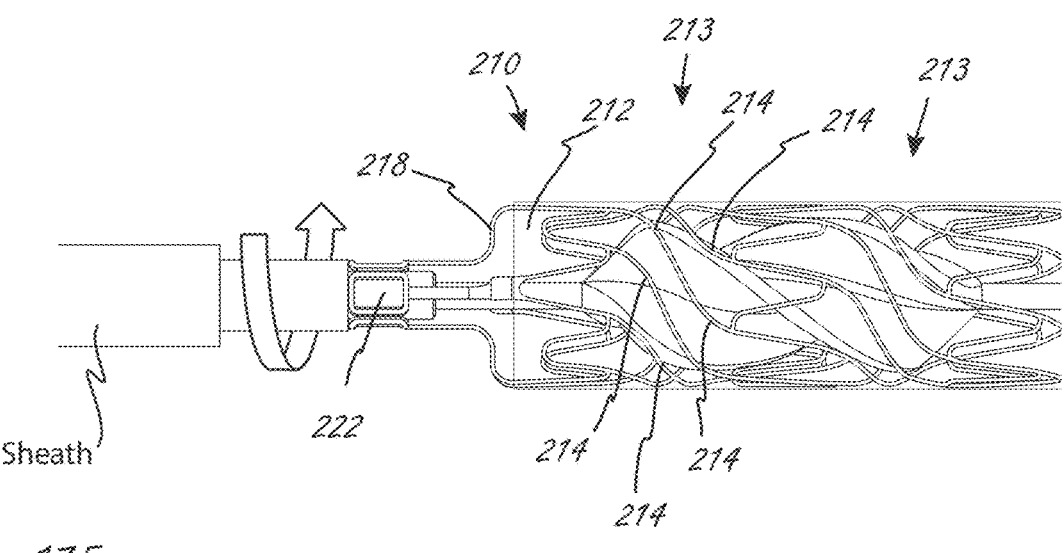
Sheath
*Fig. 17E*

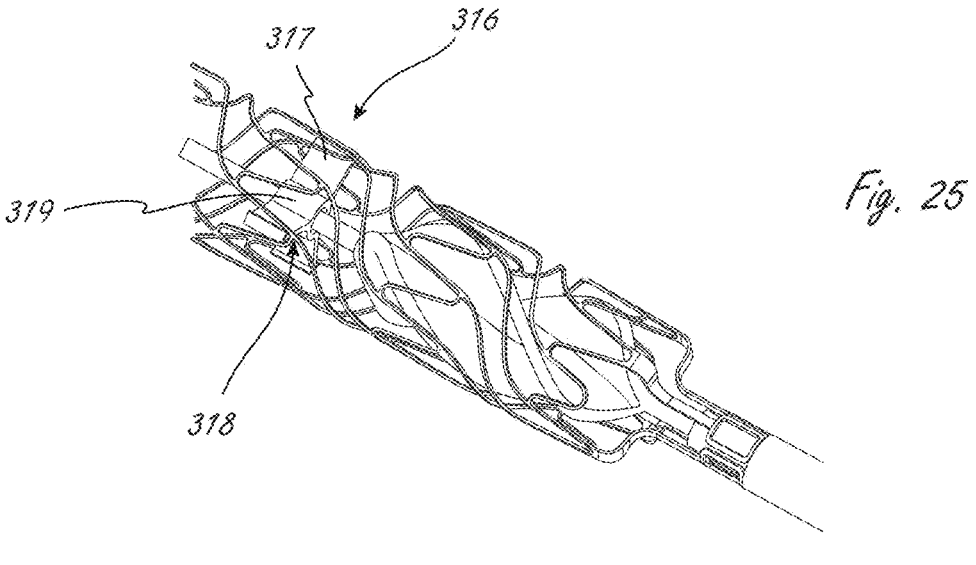
_Fig. 23_
_Fig. 24_
_Fig. 25_

Speed increasers

1

2

1. Simple gearing
- Input shaft (cable)
- Input gear
- Output gear
- Output shaft 2. Multicaptive gearing
- Input shaft (cable)
- Input gear
- Output gear 1
- Output shaft 1
- Input gear 2
- Output gear 2
- Output shaft 2

3. Same general concept but using plaetary gear box.

4. Same general concept but using magnetic gear box.

*140*  *141*

Add tension member,
ending midspan,
to induce bending in
that region

*143*

400

401

402

402

402

402

401

402

402

402

402

420

420

421   421

421

421

420

421

421

421

421

Distal

Proximal

3704

3705

Connections
(e.g. fluid, electrical, etc.)
to console

INTRAVASCULAR BLOOD PUMPS, MOTORS, AND FLUID CONTROL

CROSS REFERENCE TO RELATED APPLICATIONS

This application claims priority to U.S. Provisional Application No. 62/950,685, filed on Dec. 19, 2019, and entitled "INTRAVASCULAR BLOOD PUMPS, MOTORS, AND FLUID CONTROL", which is incorporated herein by reference in its entirety.

This application may be related to International Patent Application No. PCT/US2019/055038, filed on Oct. 7, 2019, published as WO 2020/073047, and entitled "INTRAVASCULAR BLOOD PUMPS AND METHODS OF USE", which is incorporated herein by reference in its entirety. Additionally, the disclosure from any of the following references may be incorporated by reference herein for all purposes: U.S. Pat. Nos. 9,675,739; 5,964,694; 7,027,875; 9,789,238; and 8,814,933.

INCORPORATION BY REFERENCE

All publications and patent applications mentioned in this specification are herein incorporated by reference to the same extent as if each individual publication or patent application was specifically and individually indicated to be incorporated by reference.

FIELD

The disclosure is related generally to intravascular blood pumps, motors that are configured to rotate one or more fluid control members such as one or more impellers, and/or one or more fluid pathways therein (e.g., purge fluid, lubricating fluid).

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously inserted ventricular support device.

There is a need to provide additional improvements to the field of ventricular support devices and similar blood pumps for treating compromised cardiac blood flow.

SUMMARY OF THE DISCLOSURE

The present disclosure relates to fluid movement devices, such as intravascular blood pumps, and their methods of use.

One aspect of the disclosure is an intravascular blood pump, comprising a catheter portion having a distal end including a blood pump, the blood pump having a driveshaft rotationally coupled to one or more impellers of the blood pump; and a motor assembly having a distal portion coupled to the catheter portion, the motor assembly including a motor rotationally coupled to the driveshaft, wherein the motor includes: a fluid impermeable layer disposed between the rotor and the stator; and a return fluid pathway in fluid communication with the blood pump, the return fluid pathway configured to direct fluid from the distal portion of the motor assembly, within an annular space between the fluid impermeable layer and the rotor, and out a proximal portion of the motor assembly, wherein the fluid impermeable layer is arranged to prevent fluid ingress toward the stator.

In this aspect, any of the return fluid pathway may direct fluid through a first bearing at the proximal portion of the motor assembly and a second bearing at a distal portion of the motor assembly, wherein the return fluid pathway directs fluid through spaces between rotational elements of the first and second bearings.

In this aspect, any of the blood pumps may include an expandable blood conduit and proximal and distal impellers within the expandable blood conduit.

In this aspect, the catheter portion may include a clean fluid line configured to direct clean fluid toward the blood pump.

In this aspect, the catheter portion may include a clean fluid pathway configured to direct clean fluid distally toward the blood pump, wherein the blood pump is configured to direct the clean fluid through a catheter of the blood pump and return fluid to the return fluid pathway of the motor assembly.

In this aspect, the clean fluid pathway may direct fluid through one or more of: an impeller of the blood pump, a bearing of the blood pump, a valve of the blood pump.

In this aspect, the motor assembly may be configured to remain outside a patient's body while the blood pump enters the patient's vascular system.

In this aspect, the motor assembly may be part of a handle of the blood pump system.

In this aspect, the catheter portion may include one or more wires configured to provide electrical communication between the blood pump and the motor assembly.

In this aspect, the proximal portion of the motor assembly may be coupled to a return fluid line configured to direct the fluid from the proximal portion of the motor assembly toward a fluid waste reservoir.

In this aspect, the proximal portion of the motor assembly may be coupled to one or more wires configured to provide electrical communication between the motor assembly and a console of the blood pump system.

In this aspect, the catheter portion may include a sheath fluid pathway and a catheter fluid pathway, the sheath fluid pathway configured to direct clean fluid distally within an annular space between an outer sheath and a catheter shaft of the catheter portion, the catheter fluid pathway configured to direct clean fluid distally within an annular space between the catheter shaft and a driveshaft tube of the catheter portion.

In this aspect, the catheter fluid pathway may not be in fluid communication with the sheath fluid pathway within the catheter portion.

In this aspect, the sheath fluid pathway may be configured to prevent blood accumulation in the annular space between the between a sheath and a catheter shaft at a distal end of the sheath.

In this aspect, the sheath fluid pathway may be configured to leak clean fluid into the patient's body at a distal end of the sheath.

In this aspect, the return fluid pathway may be radially within the fluid impermeable layer.

In this aspect, the fluid impermeable layer may have a cylindrical shape.

In this aspect, the fluid impermeable layer may be secured within the motor assembly.

In this aspect, the fluid impermeable layer may be secured in place between at least a first section and a second section of an outer motor assembly housing that are coupled together.

In this aspect, the first and second sections may be welded together.

In this aspect, the fluid impermeable layer may be configured to prevent fluid ingress at a wire entry region of the stator.

In this aspect, the motor assembly may include a first o-ring at a proximal side of the stator and a second o-ring at a distal side of the stator, wherein the first and second o-rings are configured to prevent fluid ingress toward the stator.

In this aspect, the first and second o-rings may be configured to prevent fluid ingress at a wire entry region of the stator.

One aspect of the disclosure is method of circulating fluid within a blood pump system, the blood pump system including a motor assembly coupled to a catheter portion, the motor assembly rotatably and fluidically in communication with a blood pump at a distal end of a catheter portion, the method comprising: receiving return purge fluid at the motor assembly proximally from the blood pump along the catheter portion; and directing the return purge fluid through a return purge fluid pathway within a motor of the motor assembly, wherein the return purge fluid pathway travels in an annular space between a fluid impermeable layer and a rotor of the motor, wherein the fluid impermeable layer is disposed radially inward with respect to the stator to prevent fluid ingress toward the stator.

In this aspect, the method can further comprise delivering clean purge fluid through a clean purge fluid pathway through the blood pump, wherein the clean purge fluid returns from the blood pump to the motor assembly as the return purge fluid.

In this aspect, the clean purge fluid may flow through one or more of: an impeller of the blood pump, a bearing of the blood pump, a valve of the blood pump.

In this aspect, the method may further comprise causing the motor to rotate a driveshaft along the catheter portion to rotate one or more impellers of the blood pump within a patient's vascular system, wherein rotating the one or more impellers pumps the patient's blood.

In this aspect, the method may further comprise inserting a guidewire through the motor toward the blood pump.

In this aspect, directing the return purge fluid through the return purge fluid pathway within the motor may lubricate the motor, flushes the motor of particles, and/or cools the motor.

In this aspect, the return purge fluid pathway may direct fluid through spaces of a rotational portion of a first bearing and a second bearing of the motor assembly, the first bearing at the proximal portion of the motor assembly and the second bearing at a distal portion of the motor assembly.

In this aspect, the method may further comprise expanding an expandable blood conduit of the blood pump, the expandable blood conduit having proximal and distal impellers therein.

In this aspect, expanding the expandable blood conduit may include retracting an outer sheath from an expandable basket of the blood pump.

In this aspect, the method may further comprises: pushing clean fluid distally through a sheath fluid pathway within an annular space between an outer sheath and a catheter shaft of the catheter portion; and pushing clean fluid distally through a catheter fluid pathway within an annular space between the catheter shaft and a driveshaft tube of the catheter portion.

In this aspect, the fluid impermeable layer may have a cylindrical shape.

In this aspect, the fluid impermeable layer may be secured within the motor assembly.

In this aspect, the fluid impermeable layer may be arranged to prevent fluid ingress at a wire entry region of the stator.

In this aspect, the motor assembly may include a first o-ring at a proximal side of the stator and a second o-ring at a distal side of the stator, wherein the first and second o-rings are configured to prevent fluid ingress toward the stator One aspect of the disclosure is a blood pump system, comprising: a motor in rotational communication with a drive shaft, the draft shaft in rotational communication with one or more impellers of a pump portion of a blood pump; a purge fluid inlet and a purge fluid pathway that extends distally from the purge fluid inlet; and a purge fluid return pathway extending proximally through the drive shaft, into the motor, through a lumen defined by a motor rotor and a motor stator, and out a proximal end of the motor, wherein the purge fluid return pathway includes a fluid impermeable layer between the motor rotor and the motor stator that is arranged to prevent fluid ingress toward the stator.

In this aspect, the purge fluid return pathway may further extend to a waste reservoir.

In this aspect, the system may further comprise a valve disposed distal to the rotor, the valve preventing fluid in the fluid return pathway from entering a hollow motor lumen, the valve configured to allow a guidewire to be advanced distally through the valve.

In this aspect, the hollow motor lumen may be sized and configured as part of a guidewire channel.

In this aspect, no amount of return purge fluid may flow radially around the stator.

In this aspect, the only flow path of return purge fluid along a length of the rotor may be between the rotor and the stator.

In this aspect, the flow path of the return purge fluid within the motor may not be outside of the stator and not radially within the rotor.

In this aspect, the system may further comprise a proximal valve disposed proximal to the rotor, the proximal valve controlling fluid into the motor hollow central lumen.

In this aspect, the purge fluid inflow pathway lubricates one or more bearings associated within the one or more impellers.

One aspect of the disclosure is a method of circulating fluid to an intravascular blood pump, comprising: delivering clean purge fluid into the blood pump, distally down a purge inflow pathway that is radially outside of a central guidewire channel defined by a driveshaft; receiving return purge fluid proximally along a return purge fluid pathway that includes the guidewire channel, into a motor adapted and configured to drive the driveshaft, through a motor lumen defined by a motor rotor and a motor stator, and out a proximal region of the motor, wherein the return purge fluid pathway includes a fluid impermeable layer that is disposed radially inward with respect to the motor stator to prevent fluid ingress toward the stator.

In this aspect, the purge fluid return pathway may further extend to a waste reservoir.

In this aspect, the method may further comprise a valve disposed distal to the rotor, the valve preventing fluid in the fluid return pathway from entering a hollow motor lumen, the valve configured to allow a guidewire to be advanced distally through the valve.

This aspect, the hollow motor lumen may be sized and configured as part of a guidewire channel.

In this aspect, no amount of return purge fluid may flow radially around the stator.

In this aspect, the only flow path of return purge fluid along a length of the rotor may be between the rotor and the stator.

In this aspect, the flow path of the return purge fluid within the motor may not be outside of the stator and not radially within the rotor.

In this aspect, the method may further comprise a proximal valve disposed proximal to the rotor, the proximal valve controlling fluid into the motor hollow central lumen.

In this aspect, the purge fluid inflow pathway may lubricate one or more bearings associated within the one or more impellers.

One aspect of this disclosure is a method of circulating fluid to an intravascular blood pump, comprising: delivering clean purge fluid into the blood pump, distally down a purge inflow pathway that is radially outside of a central guidewire channel defined by a driveshaft; receiving return purge fluid proximally along a return purge fluid pathway that includes the guidewire channel, into a motor adapted and configured to drive the driveshaft, through a motor lumen defined by a motor rotor and a motor stator, and out a proximal region of the motor, wherein the return purge fluid pathway includes a fluid impermeable layer that is disposed radially inward with respect to the motor stator to prevent fluid ingress toward the stator.

In this aspect, the method may further comprise lubricating one or more bearings of a pump portion of the blood pump with the purge fluid.

In this aspect, the one or more bearings may be associated with more than one impeller of the pump portion.

In this aspect, the method may further comprise lubricating one or more motor bearings with the return purge fluid.

In this aspect, the method may further comprise preventing return purge fluid from entering a hollow motor lumen.

In this aspect, the hollow motor lumen may be sized and configured as a guidewire channel.

In this aspect, a valve may be disposed distal to the rotor.

In this aspect, the method may further comprise preventing return purge fluid from passing radially outside of the stator.

In this aspect, the method may further comprise directing return purge fluid solely between the stator and rotor.

In this aspect, the return purge fluid may be directed along a length of the rotor and not within a hollow lumen and not radially outside the stator.

In this aspect, the method may further comprise rotating the one or more impellers while the purge fluid is circulating along the inflow path and the return path.

One aspect of the disclosure is a blood pump system, comprising: a catheter portion having a distal end including a blood pump, the blood pump having a driveshaft rotationally coupled to one or more impellers of the blood pump; and a motor assembly having a distal portion coupled to the catheter portion, the motor assembly including a motor rotationally coupled to the driveshaft, wherein the motor includes: a return fluid pathway in fluid communication with the blood pump, the return fluid pathway configured to direct fluid from the distal portion of the motor assembly, within an annular space between the stator and the rotor, and out a proximal portion of the motor assembly.

In this aspect, the return fluid pathway may direct fluid through a first bearing at the proximal portion of the motor assembly and a second bearing at a distal portion of the motor assembly, wherein the return fluid pathway directs fluid through spaces between rotational elements of the first and second bearings.

In this aspect, the blood pump may include an expandable blood conduit and proximal and distal impellers within the expandable blood conduit.

In this aspect, the catheter portion may include a clean fluid line configured to direct clean fluid toward the blood pump.

In this aspect, the catheter portion may include a clean fluid pathway configured to direct clean fluid distally toward the blood pump, wherein the blood pump is configured to direct the clean fluid through a catheter of the blood pump and return fluid to the return fluid pathway of the motor assembly.

In this aspect, the clean fluid pathway may direct fluid through one or more of: an impeller of the blood pump, a bearing of the blood pump, a valve of the blood pump.

In this aspect, the motor assembly may be configured to remain outside a patient's body while the blood pump enters the patient's vascular system.

In this aspect, the motor assembly may be part of a handle of the blood pump system.

In this aspect, the catheter portion may include one or more wires configured to provide electrical communication between the blood pump and the motor assembly.

In this aspect, the proximal portion of the motor assembly may be coupled to a return fluid line configured to direct the fluid from the proximal portion of the motor assembly toward a fluid waste reservoir.

In this aspect, the proximal portion of the motor assembly may be coupled to one or more wires configured to provide electrical communication between the motor assembly and a console of the blood pump system.

In this aspect, the catheter portion may include a sheath fluid pathway and a catheter fluid pathway, the sheath fluid pathway configured to direct clean fluid distally within an annular space between an outer sheath and a catheter shaft of the catheter portion, the catheter fluid pathway configured to direct clean fluid distally within an annular space between the catheter shaft and a driveshaft tube of the catheter portion.

In this aspect, the catheter fluid pathway may not be in fluid communication with the sheath fluid pathway within the catheter portion.

In this aspect, the sheath fluid pathway may be configured to prevent blood accumulation in the annular space between the between a sheath and a catheter shaft at a distal end of the sheath.

In this aspect, the sheath fluid pathway may be configured to leak clean fluid into the patient's body at a distal end of the sheath.

In this aspect, the motor assembly may include a fluid impermeable layer between the rotor and the stator configured to prevent fluid ingress toward the stator.

In this aspect, the return fluid pathway may be radially within the fluid impermeable layer.

In this aspect, the fluid impermeable layer may have a cylindrical shape.

In this aspect, the fluid impermeable layer may be secured within the motor assembly.

In this aspect, the fluid impermeable layer may be secured in place between at least a first section and a second section of an outer motor assembly housing that are coupled together.

In this aspect, the first and a second sections may be welded together.

In this aspect, the fluid impermeable layer may be configured to prevent fluid ingress at a wire entry region of the stator.

In this aspect, the motor assembly may include a first o-ring at a proximal side of the stator and a second o-ring at a distal side of the stator, wherein the first and second o-rings are configured to prevent fluid ingress toward the stator.

In this aspect, the first and second o-rings may be configured to prevent fluid ingress at a wire entry region of the stator.

One aspect of the disclosure is a method of circulating fluid within a blood pump system, the blood pump system including a motor assembly coupled to a catheter portion, the motor assembly rotatably and fluidically in communication with a blood pump at a distal end of a catheter portion, the method comprising: receiving return purge fluid at the motor assembly proximally from the blood pump along the catheter portion; and directing the return purge fluid through a return purge fluid pathway within a motor of the motor assembly, wherein the return purge fluid pathway travels in an annular space between a rotor and a stator of the motor.

In this aspect, the method may further comprise delivering clean purge fluid through a clean purge fluid pathway through the blood pump, wherein the clean purge fluid returns from the blood pump to the motor assembly as the return purge fluid.

In this aspect, the clean purge fluid may flow through one or more of: an impeller of the blood pump, a bearing of the blood pump, a valve of the blood pump.

In this aspect, the method may further comprise causing the motor to rotate a driveshaft along the catheter portion to rotate one or more impellers of the blood pump within a patient's vascular system, wherein rotating the one or more impellers pumps the patient's blood.

In this aspect, the method may further comprise inserting a guidewire through the motor toward the blood pump.

In this aspect, directing the return purge fluid through the return purge fluid pathway within the motor may lubricates the motor, flush the motor of particles and/or cool the motor.

In this aspect, the return purge fluid pathway may direct fluid through spaces of a rotational portion of a first bearing and a second bearing of the motor assembly, the first bearing at the proximal portion of the motor assembly and the second bearing at a distal portion of the motor assembly.

In this aspect, the method may further comprise expanding an expandable blood conduit of the blood pump, the expandable blood conduit having proximal and distal impellers therein.

In this aspect, expanding the expandable blood conduit may include retracting an outer sheath from an expandable basket of the blood pump.

In this aspect, the method may further comprise: pushing clean fluid distally through a sheath fluid pathway within an annular space between an outer sheath and a catheter shaft of the catheter portion; and pushing clean fluid distally through a catheter fluid pathway within an annular space between the catheter shaft and a driveshaft tube of the catheter portion In this aspect, the return purge fluid pathway may direct the return purge fluid within a fluid impermeable layer that is disposed radially inward with respect to the stator to prevent fluid ingress toward the stator.

In this aspect, the fluid impermeable layer may have a cylindrical shape.

In this aspect, the fluid impermeable layer may be secured within the motor assembly.

In this aspect, the fluid impermeable layer may be configured to prevent fluid ingress at a wire entry region of the stator.

In this aspect, the motor assembly may include a first o-ring at a proximal side of the stator and a second o-ring at a distal side of the stator, wherein the first and second o-rings are configured to prevent fluid ingress toward the stator.

These and other aspects are described herein.

BRIEF DESCRIPTION OF THE DRAWINGS

FIG. 6B illustrates at least a portion of an exemplary medical device that has a pump portion, where at least two different impellers can be rotated at different speeds.

FIG. 6C illustrates at least a portion of an exemplary medical device that has a pump portion with at least two impellers with different pitches.

FIG. 7 illustrates at least a portion of an exemplary medical device that has a pump portion.

FIGS. 13A, 13B and 13C illustrate different view of an exemplary central, or intermediate, member.

FIGS. 15A-D illustrates an exemplary blood pump that includes a guidewire pathway and at least one fluid purge pathway.

FIGS. 17A-F illustrate an exemplary pump portion that includes an expandable housing, including an exemplary scaffold design.

FIG. 23 illustrates a portion of an expandable housing with a fluid lumen that has an outwardly flared configuration at at least one end of the fluid lumen.

FIG. 24 illustrates an outer housing that includes one or more blades extending radially inward.

FIG. 25 illustrates a proximal portion of an exemplary pump portion, wherein the pump portion includes one or blades that are sized and configured to interface with a portion of the scaffold.

FIG. 35B illustrates the configuration of the diffusers in the top view, as well as the fluid direction relative to the diffuser.

FIG. 37A shows a cross-section view of the motor showing an exemplary fluid pathway therethrough; and FIG. 37B shows an external side view of the motor.

DETAILED DESCRIPTION

The present disclosure is related to medical devices, systems, and methods of use and manufacture. Medical devices herein may include a pump portion adapted and configured to be disposed within a physiologic vessel, wherein the pump includes one or more components that act upon fluid. For example, pump portions herein may include one or more impellers that are configured such that when rotated, they facilitate the movement of a fluid such as blood.

Figure 1:
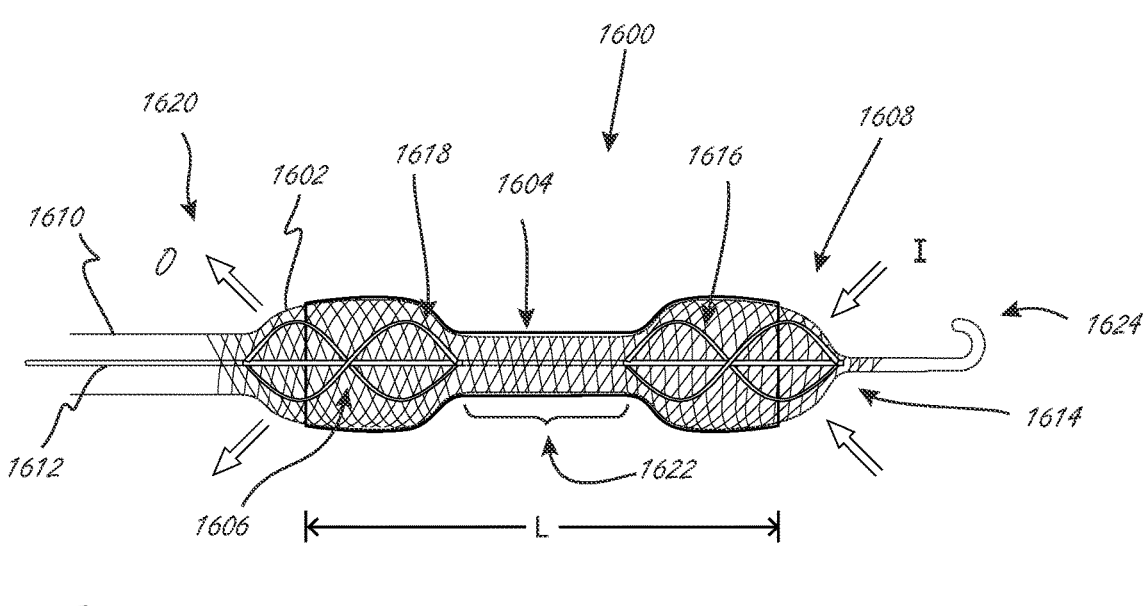
FIG. 1 is a side view of an exemplary pump portion that includes a conduit, a plurality of impellers, an expandable member

FIG. 1 is a side view illustrating a distal portion of an exemplary intravascular fluid pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can in rotational communication with drive cable 1612, directly or indirectly. Drive cable 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Figure 2:
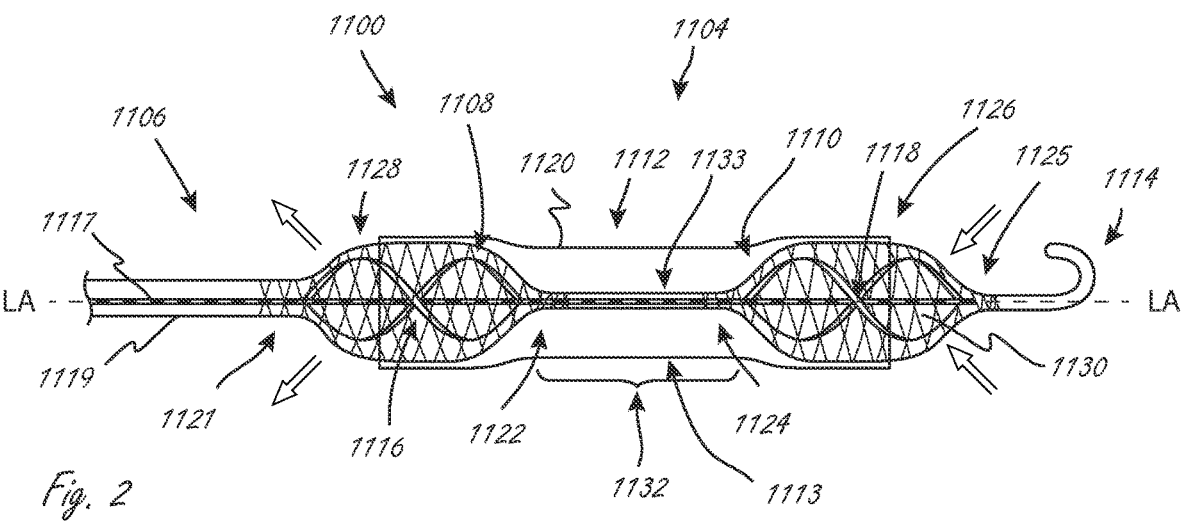
FIG. 2 is a side view of an exemplary pump portion that includes a conduit, a plurality of impellers, and a plurality of expandable members.

FIG. 2 is a side view illustrating a deployed configuration (shown extracorporally) of a distal portion of an exemplary embodiment of a fluid movement system. Exemplary system 1100 includes pump portion 1104 (which as set forth herein may also be referred to herein as a pump portion) and an elongate portion 1106 extending from pump portion 1104. Elongate portion 1106 can extend to a more proximal region of the system, not shown for clarity, and that can include, for example, a motor. Pump portion 1104 includes first expandable member 1108 and second expandable member 1110, axially spaced apart along a longitudinal axis LA of pump portion 1104. Spaced axially in this context refers to the entire first expandable member being axially spaced from the entire second expandable member along a longitudinal axis LA of pump portion 1104. A first end 1122 of first expandable member 1108 is axially spaced from a first end 1124 of second expandable member 1110. Some "expandable members" herein may also be referred to herein as baskets.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Pump portion 1104 also includes blood flow conduit 1112, which in this embodiment is supported by first expandable member 1108 and to second expandable member 1110. Conduit 1112 also extends axially in between first expandable member 1108 and second expandable member 1110 in the deployed configuration. A central region 1113 of conduit 1112 spans an axial distance 1132 where the pump portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a conduit being coupled to an expandable member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations. The conduits herein are considered to create a pathway for fluid to be moved, and may be defined by a one or more components of the pump portion.

Any of the conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as pump portion 1104 is deployed towards the configuration shown in FIG. 2. The conduit may be stretched tightly between the expandable members in some embodiments. The conduit may alternatively be designed with a looseness that causes a greater degree of compliance. This can be desirable when the pump portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the conduits herein, or at least a portion of the conduit, can be impermeable to blood. In FIG. 2, pump portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable members help maintain the conduit in an open configuration by providing radial support for the conduit, while each also creates a working environment for an impeller, described below. Each of the expandable members, when in the deployed configuration, is maintained in a spaced relationship relative to a respective impeller, which allows the impeller to rotate within the expandable member without contacting the expandable member. Pump portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the pump portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this FIG., portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and pump portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Pump portion 1104 is adapted and configured to be collapsed to a smaller profile than its deployed configuration (which is shown in FIG. 2). This allows it to be delivered using a lower profile delivery device (smaller French size) than would be required if none of pump portion 1104 was collapsible. Even if not specifically stated herein, any of the expandable members and impellers may be adapted and configured to be collapsible to some extent to a smaller delivery configuration.

The pump portions herein can be collapsed to a collapsed delivery configuration using conventional techniques, such as with an outer sheath that is movable relative to the pump portion (e.g., by axially moving one or both of the sheath and pump portion). For example without limitation, any of the systems, devices, or methods shown in the following references may be used to facilitate the collapse of a pump portion herein: U.S. Pat. No. 7,841,976 or 8,052,749, the disclosures of which are incorporated by reference herein for all purposes.

Figures 3A, 3B:
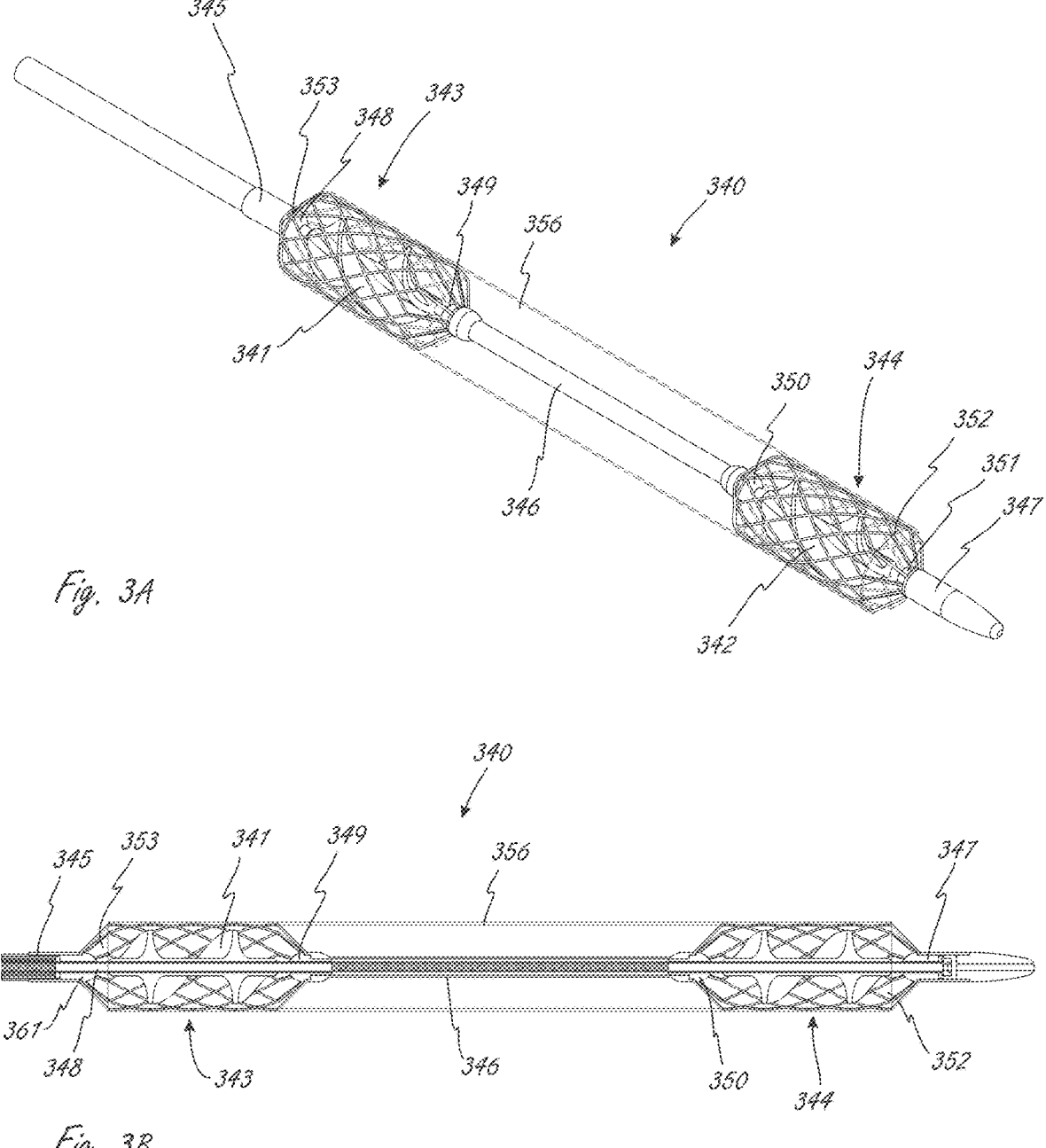
FIGS. 3A, 3B, 3C and 3D illustrate an exemplary pump portion that includes a conduit, a plurality of impellers, and a plurality of expandable members.
Figure 3C:
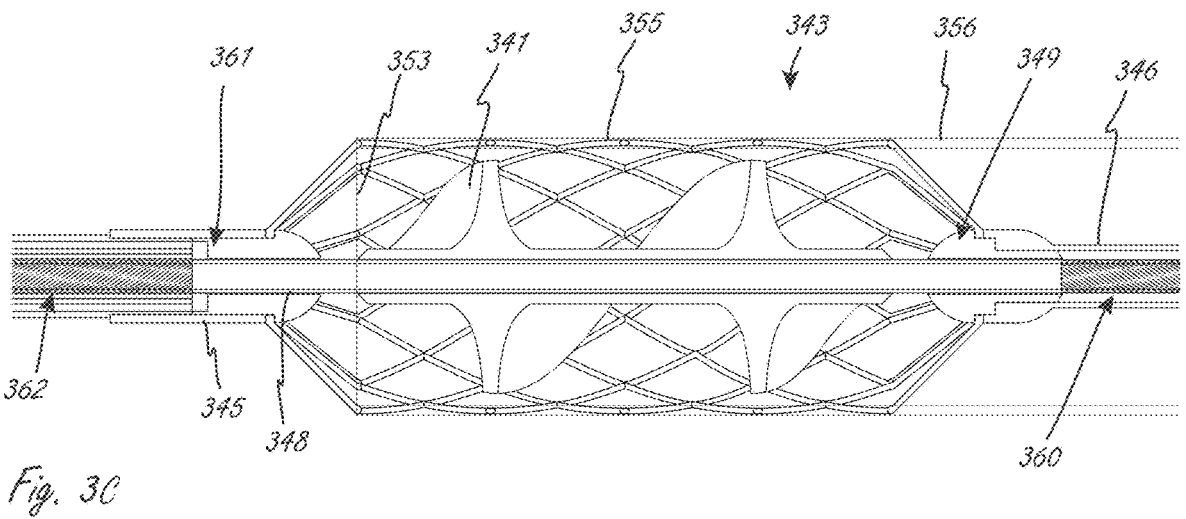
Figure 3D:
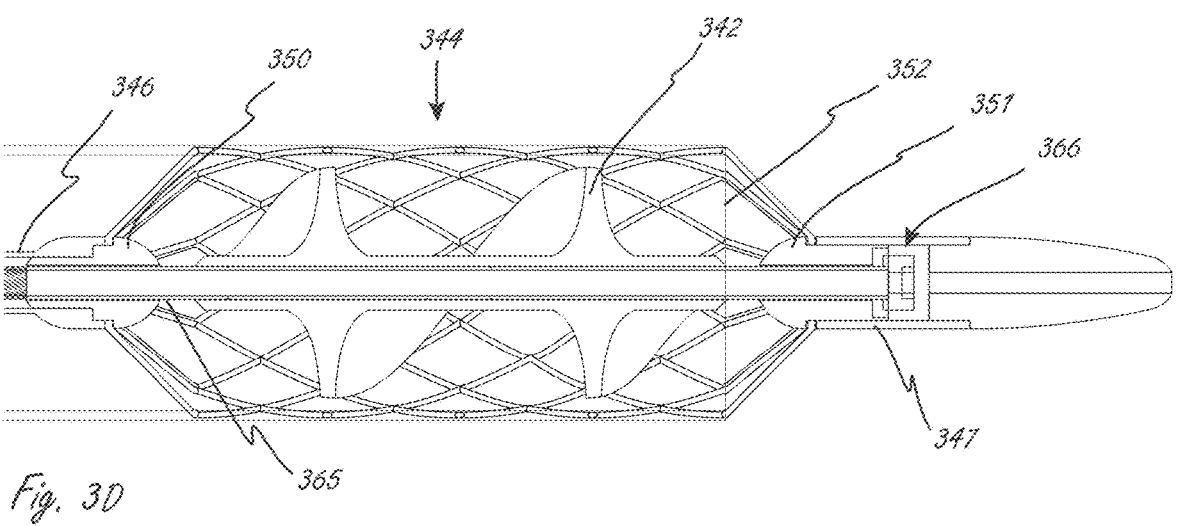

FIGS. 3A-3E show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the pump portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the pump portion, allowing the pump portion to be, for example, advanced over a guidewire for positioning the pump portion. In this embodiment the second and fourth sections can be stiffer than first and third sections. For example, second and fourth can be tubular and first and third sections can be wound material to impart less stiffness.

Pump portion 340 includes a blood flow conduit, proximal expandable member 343 and distal expandable member 344, each of which extends radially outside of one of the impellers. The expandable members have distal and proximal ends that also extend axially beyond distal and proximal ends of the impellers, which can be seen in FIGS. 3B-3D. That pumps also includes conduit 356, which has a proximal end 353 and a distal end 352. The two expandable members each include a plurality of proximal struts and a plurality of distal struts. The proximal struts in proximal expandable member 343 extend to and are secured to shaft section 345, which is coupled to bearing 361, through which the drive cable extends and is configured and sized to rotate. The distal struts of proximal expandable member 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts of distal expandable member 344 extend to and secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts of distal expandable member extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
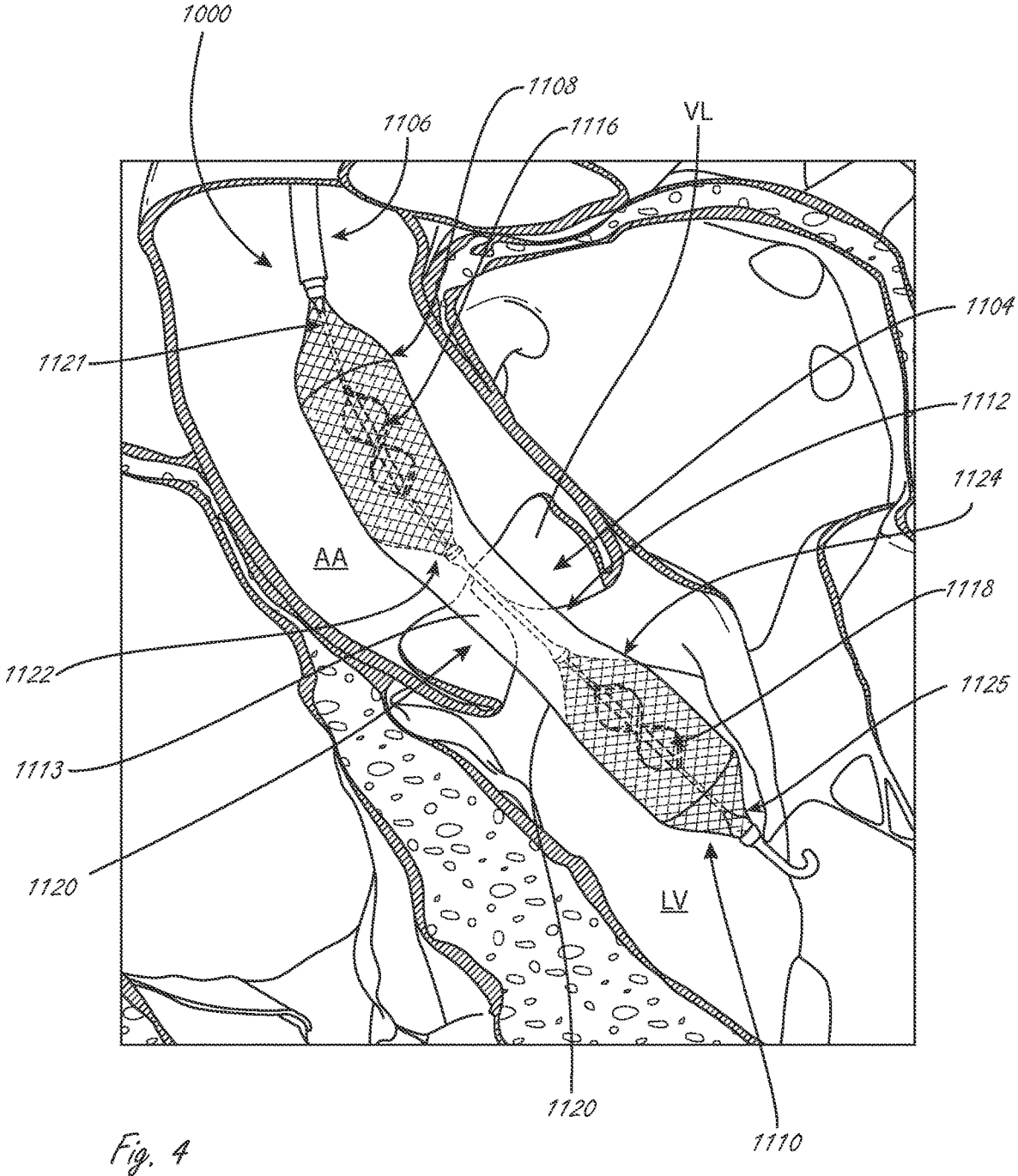
FIG. 4 illustrates an exemplary placement of a pump portion, the pump portion including a conduit, a plurality of expandable members, and a plurality of impellers.

FIG. 4 illustrates an exemplary placement of pump portion 1104 from system 1000 from FIG. 2, and also illustrates an exemplary placement location for any of the pump portions herein. One difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which pump portion 1104 is disposed during delivery to a location near an aortic valve. The sheath or shaft can be moved proximally (towards the ascending aorta "AA" and away from left ventricle "LV") to allow for deployment and expansion of pump portion 1104. For example, the sheath can be withdrawn to allow for expansion of second expandable member 1110, with continued proximal movement allowing first expandable member 1108 to expand.

In this embodiment, second expandable member 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable members 1108 and 1110 causes conduit 1112 to assume a more open configuration, as shown in FIG. 4. Thus, while in this embodiment conduit 1112 does not have the same self-expanding properties as the expandable members, the conduit will assume a deployed, more open configuration when the working end is deployed. At least a portion of central region 1113 of conduit 1112 is positioned at an aortic valve coaptation region. In FIGS. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable member 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable member 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the pump portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the pump at the locations of the impellers, which can allow for more deformation of the pump portion at the location of the leaflets than would occur if an expandable member spanned the aortic valve leaflets. Having a more flexible central region may also cause less damage to the leaflets after the pump portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

Embodiments herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
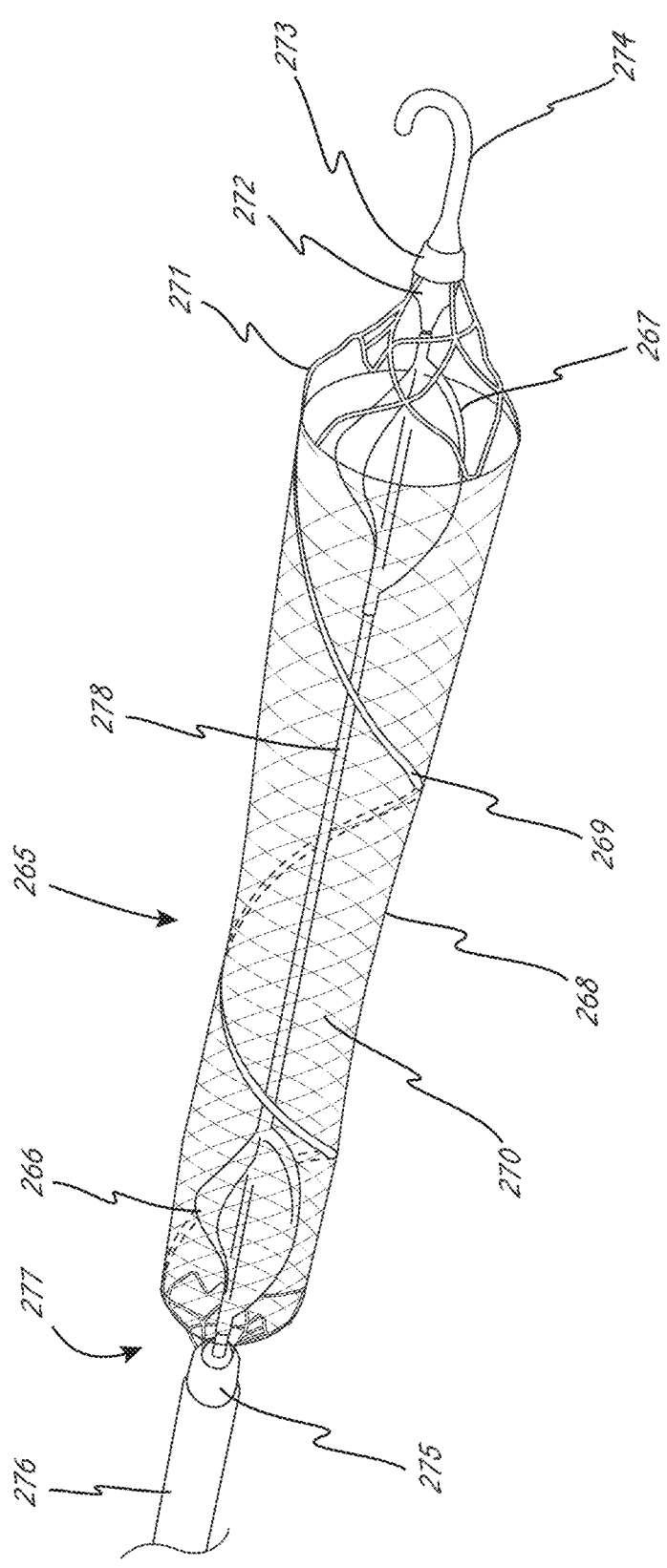
FIG. 5 illustrates an exemplary pump portion.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable member, referred to 270 generally, and conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member.

There are alternative ways to construct the pump portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the conduits herein act to, are configured to, and are made of material(s) that create a fluid lumen therein between an first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit can extend radially within the expandable member so that inner surface of the conduit is radially within the expandable member where it is secured to the expandable member.

Any of the expandable member(s) herein can be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figure 6A:
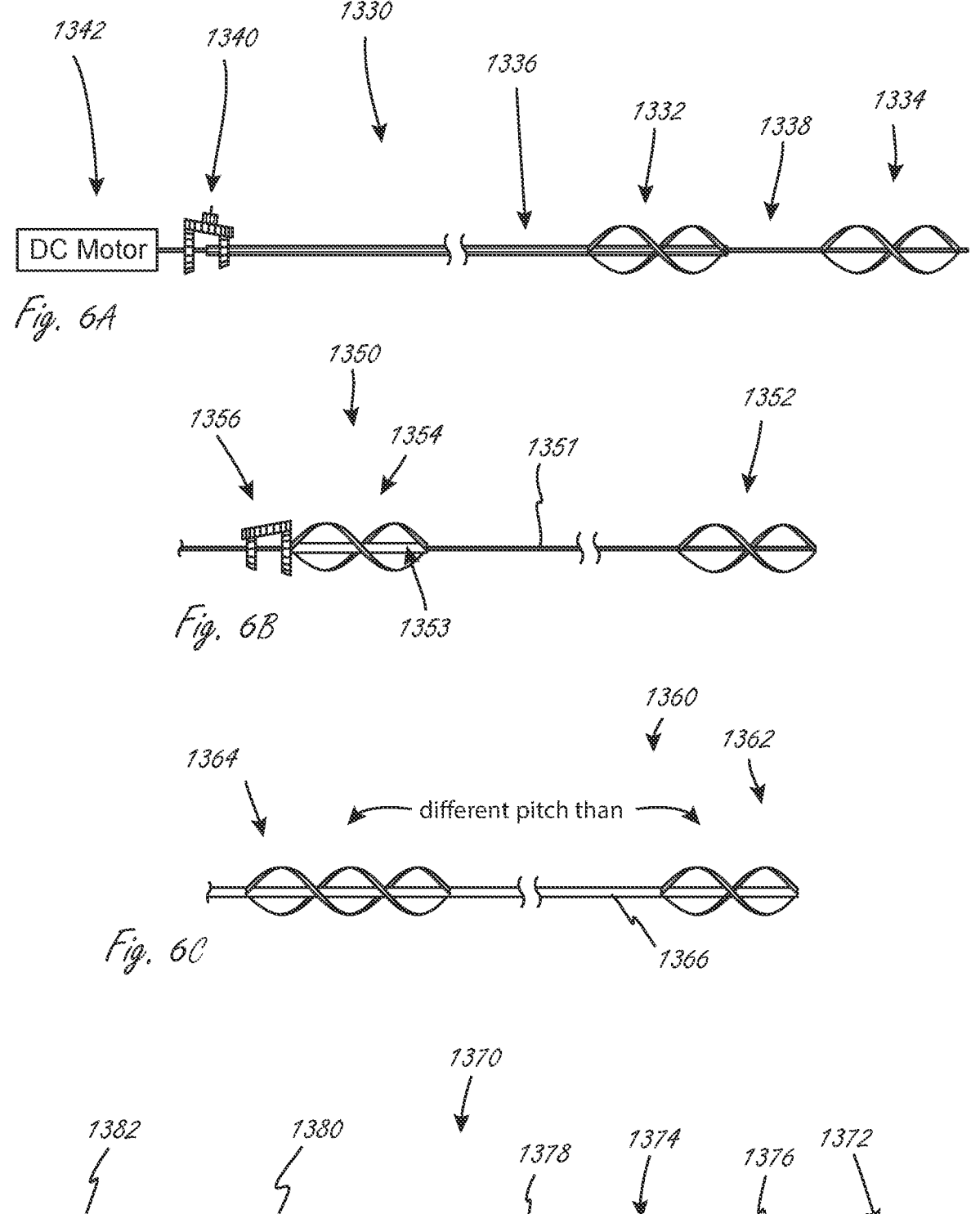
FIG. 6A illustrates at least a portion of an exemplary medical device that has a pump portion, where at least two different impellers can be rotated at different speeds.

In any of the embodiments herein in which the medical device includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

FIG. 7 shows an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

In some embodiments, a common drive cable or shaft can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion can have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figures 8, 9:
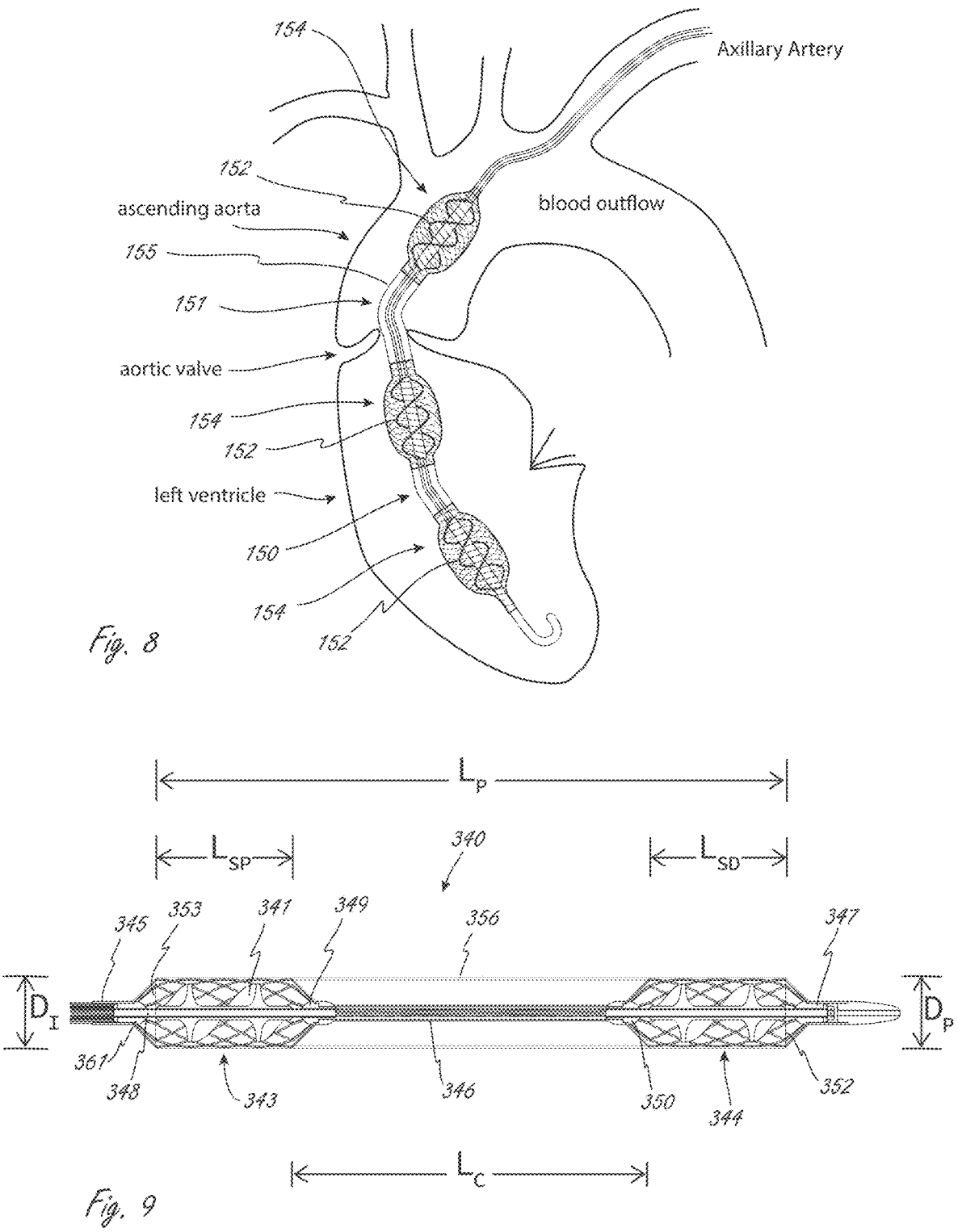
FIG. 8 illustrates a pump portion with multiple impellers, with a bend formed therein between adjacent impellers.
FIG. 9 illustrates a pump portion with a plurality of impellers.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. One will appreciate from the description herein, however, that the pump may be introduced and tracked into position in various manner including a femoral approach over the aortic arch.

One aspect of the disclosure is an intravascular blood pump that includes a distal impeller axially spaced from a proximal impeller. In one embodiment, the distal and proximal impellers are separated from each other. For example, the distal and proximal impellers may be connected solely by their individual attachment to a common driveshaft. This is distinct from an impeller having multiple blade rows. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provides exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein, at least one of a flow diffuser or diffusers and a stator or stators is/are located between two or more impellers along the catheter shaft, any one of which can increase fluid pressure between impellers, reduce swirl of the fluid, and/or increase the efficiency of the multiple impellers as a group.

In any of the embodiments herein, features at the fluid exit of an expandable shroud basket or expandable member are shaped to act as a flow diffuser, such as stent-like struts at the attachments between the catheter shaft outer dimension and the expandable member outer dimension, which can be blade-shaped with a twist directed to change the flow direction of blood. In any of the embodiments herein, one or more portions of the catheter shaft downstream of an impeller may flare to a larger diameter to change the angle of blood flow and cause deceleration of the blood flow to a speed closer to native aortic blood flow. Exemplary locations for a larger diameter downstream of an impeller would be at or near the area where an expandable shroud basket attaches to the catheter shaft, and/or at a bearing housing adjacent the impeller, or on or adjacent an internal motor.

In some embodiments, the pump portion can include one or more central members disposed axially in between proximal and distal impellers. The one or more central members may be coupled directly to one another, or they may not. The one or more central members may provide one or more of the following exemplary functions: structural support, flow modification, and maintaining impeller alignment. If the one or more central members provide structural support, the one or more central members may provide structural support to the outer conduit (which may be referred to herein as a "housing") and/or to one or more impellers. For example, they may help maintain tip gap in one or more impellers. In the description that follows, the one or more central members are not in rotational operation with an impeller, unless indicated to the contrary. As used herein, the term "central member" or derivatives thereof does not imply that the member is located at at least a midpoint between two impellers, but simply that the central member is somewhere axially between the two impellers. "Central member" may thus be used interchangeably herein with the term "intermediate member."

Figure 10:
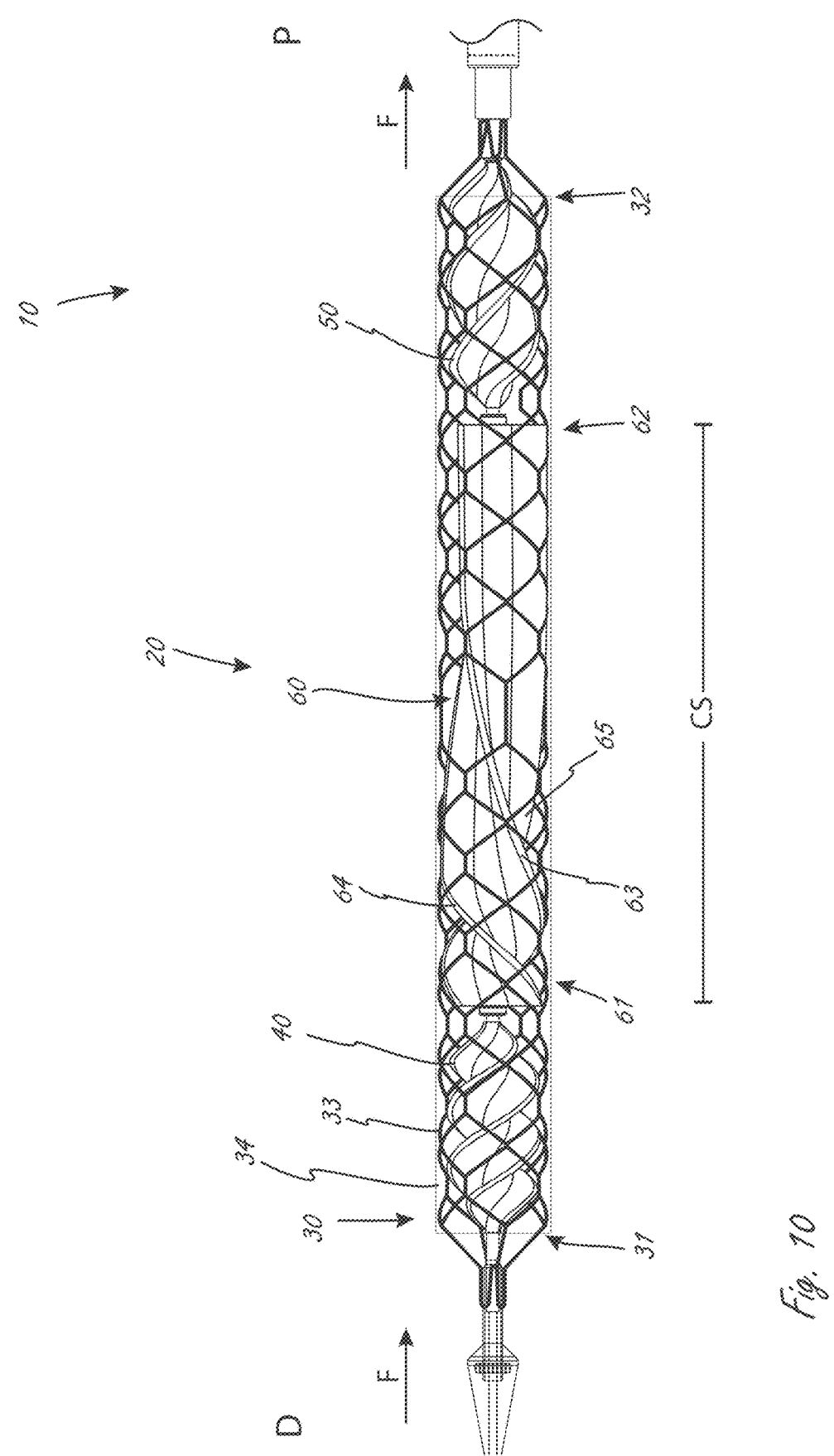
FIG. 10 shows a side view of a portion of a fluid movement device, including a pump portion thereof, that includes a central, or intermediate, member axially spaced between first and second impellers.

FIG. 10 is a side view illustrating an exemplary pump portion 20 of a fluid pumping apparatus 10. The distal direction is indicated with a "D" and the proximal direction is indicated with a "P." Pump portion 20 (and other pump portions herein) may also be referred to as a distal portion herein. Pump portion 20 includes a fluid flow conduit as is described herein, as well as expandable member 30. Pump portion 20 also includes support structure 33 (which may be referred to herein as a scaffold), which in this embodiment is a stent-like member, but can be constructed using any of the examples provided herein. The conduit includes a membrane 34 that has a distal end 31 and proximal end 32. Membrane 34 is coupled to support structure 33. Membrane 34 at least partially creates and defines an internal lumen through which fluid flows when impellers 40 and 50 are activated. Membrane 34 can have any of the properties of any of the conduits that are described herein. When support structure 33 expands to the deployed and expanded configuration shown in FIG. 10, the conduit also assumes the open configuration shown in FIG. 10. Fluid flow is indicated generally in the direction of arrows "F" when impellers 40 and 50 are activated. Impellers 40 and 50 can be any of the impellers described herein and can have any of the properties described herein.

Figures 11A, 11B, 11C:
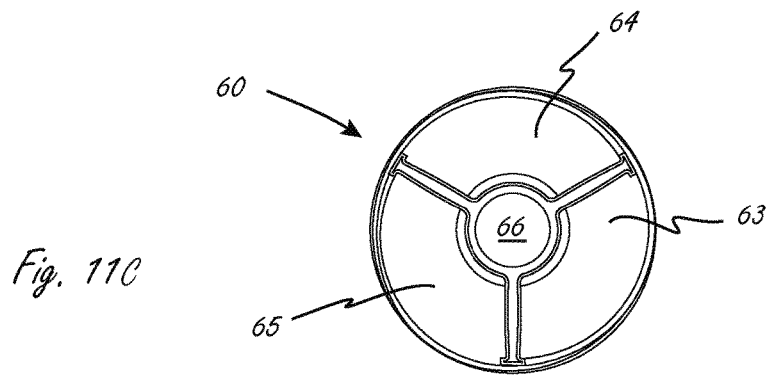
FIGS. 11A, 11B and 11C illustrates an exemplary central, or intermediate, member.

In this embodiment, pump portion 20 includes a central member 60 that is disposed axially between distal impeller 40 and proximal impeller 50. In this embodiment, central member 60 functions at least as a flow control member to modify or control the flow of blood within the fluid lumen. FIGS. 11A, 11B and 11C show perspective, side, and distal end views of central member 60, with the other pump components of the distal portion removed for clarity. Central member 60 includes hub 67 and a plurality of blades extending therefrom, in this embodiment three (i.e., blades 63, 64 and 65), although more or fewer blades may be used. Central member 60 has a distal, or front, region 61 and a back, or proximal, region 62. The blades in distal region 61 are configured to recover pressure from distal impeller 40, while the blades in proximal region 62 are configured to direct flow to proximal impeller 50. The blades in distal region 61 have a higher degree of curvature, relative to the hub, than do the blades in proximal region 62. The degree of curvature generally decreases from the distal end to the proximal end. This creates the transition between the distal region that acts more as a diffuser, to the proximal end, which acts more as a stator or guide vane. Proximal region 62 provides the functionality of a stator in this embodiment.

In addition to controlling flow and creating particular types of flow along its length, central member 60 also imparts structural support to the conduit. Member 60 provides stability in the region that is axially between impellers 40 and 50. The central region in between the impellers may receive a variety of forces thereon, and member 60 can reinforce the central region in response to those forces. For example, distal region 20 may be positioned in a heart, and in particular, the central region between the impellers may be positioned across a heart valve (e.g., aortic valve) where a great deal of motion occurs as valves open and close. The forces from valve coaptation can impart radially inward forces on expandable member 30, and member 60 can reinforce at least some portion of (including substantially the entire portion) the central span of expandable member 30 and keep the lumen open. Additionally, for example, member 60 can also reduce vibrations between the impellers that occur as the impellers rotate. The structural support provided in the central region can help maintain the gap between the tips of the impellers and the expandable member 30. Central member 60 is adapted and configured to be collapsed to a delivery configuration (like the impellers), and when expanded to the state shown in FIG. 10, it engages the expandable member 30 and provides structural support from within the lumen. In alternative embodiments, the central member 60 can be permanently attached to the expandable member, so that they collapse and expand as a unit. In this embodiment, central member 60 is thus both adapted and configured to control and create particular flow along its length in between the impellers, as well as provide structural support to the expandable member.

Any central member (e.g., control member 60) can extend axially almost the entire central span ("CS") between the impellers. The length of central span "CS" is shown in FIG. 10. As discussed above, there are structural support advantages to have a structural support member (e.g., member 60) disposed directly adjacent an impeller, as is the case with both impellers in the embodiment in FIG. 10. If it is desired to have a single central member extend from a distal end to a proximal end (as in the embodiment in FIG. 10), then the central member can extend at least 75% of the central span distance between the impellers, or at least 80%, or at least 85%, or at least 90%, or at least 95%. It is desirable to have a spacing between the impeller and control member, which prevent friction from contact between the rotating impeller and the control member.

Figure 12A:
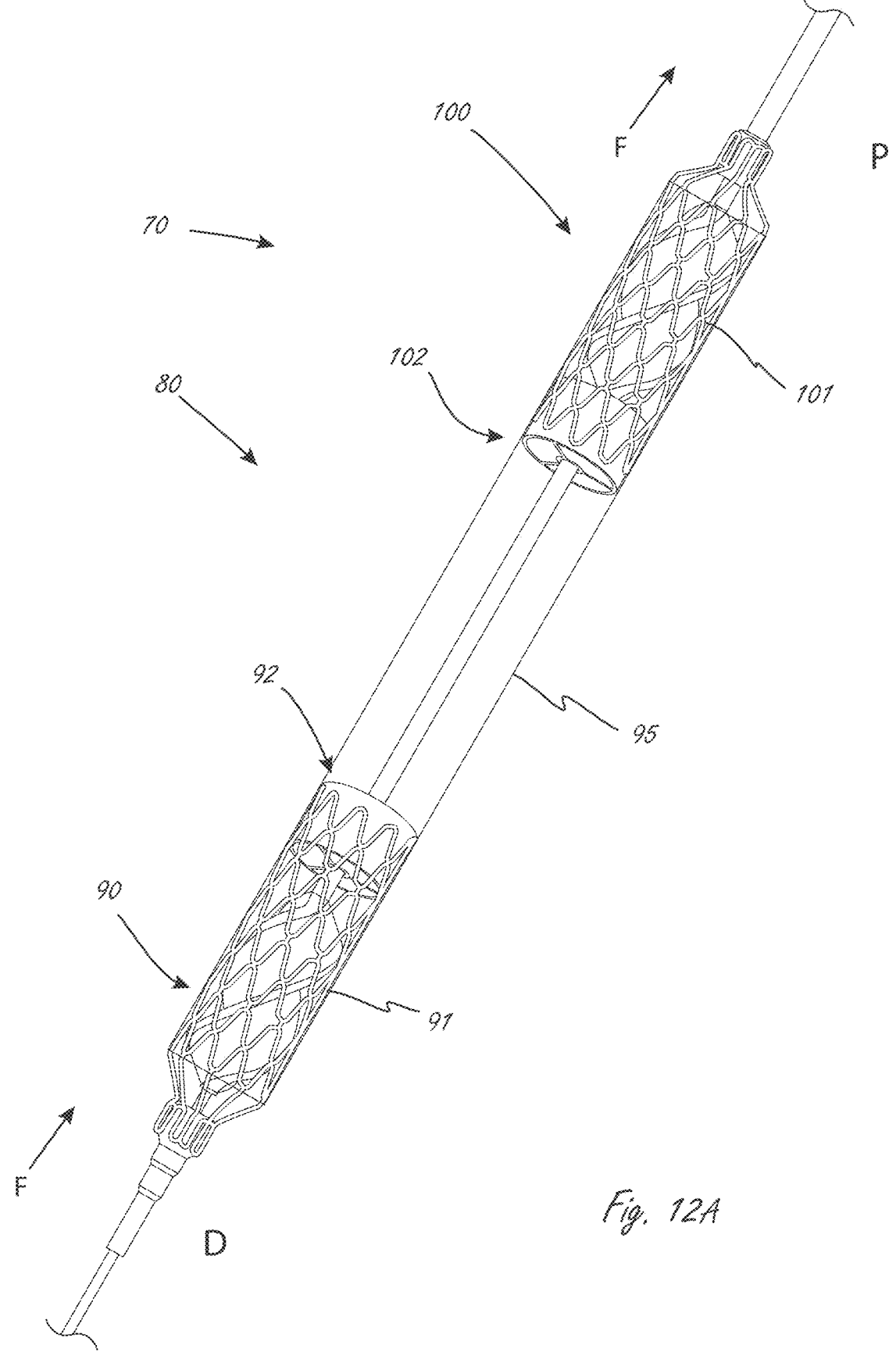
FIGS. 12A, 12B, 12C and 12D illustrate different views of an exemplary medical device, including a pump portion or a portion of a pump portion, that includes a first central (intermediate) member and a second central (intermediate) member.
Figure 12B:
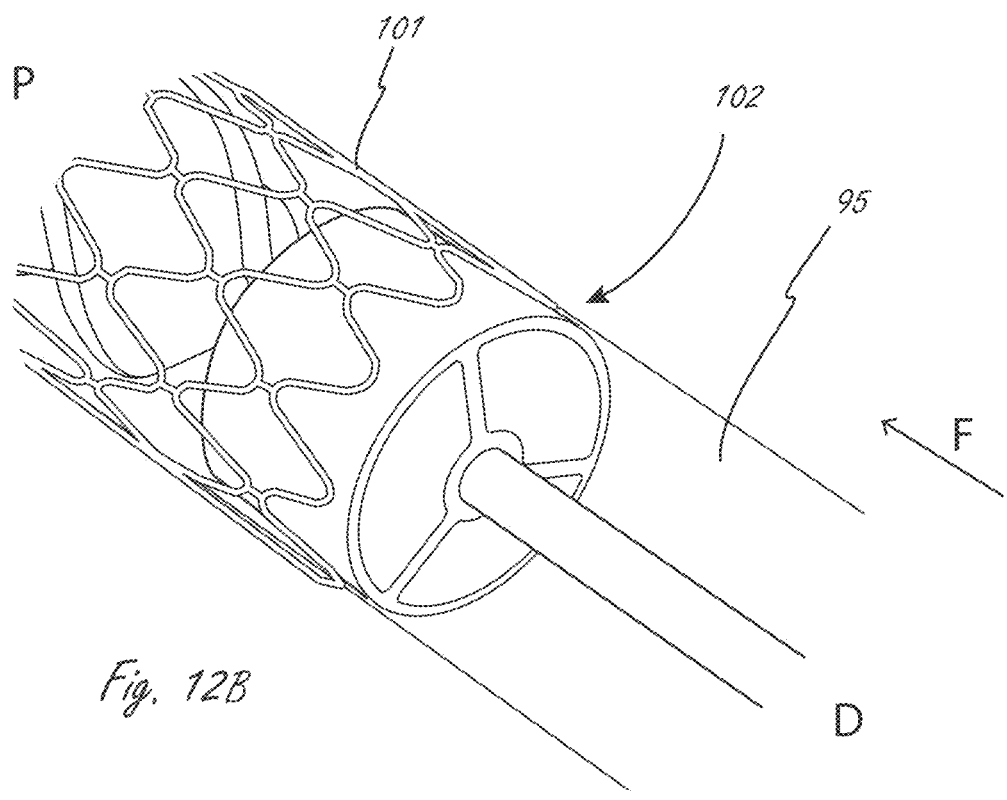
Figure 12C:
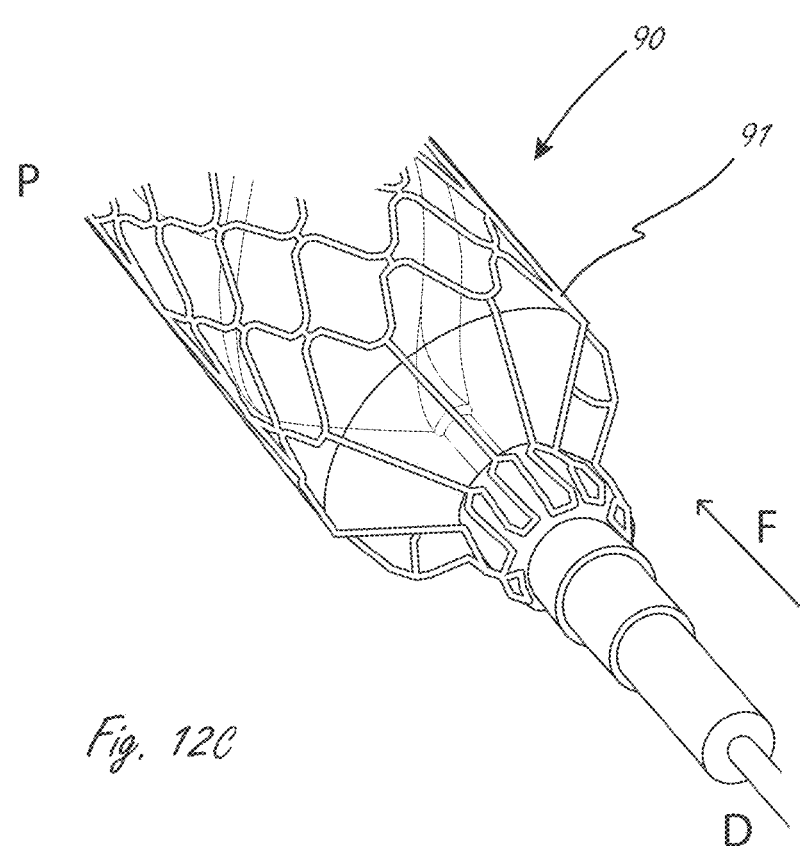
Figure 12D:
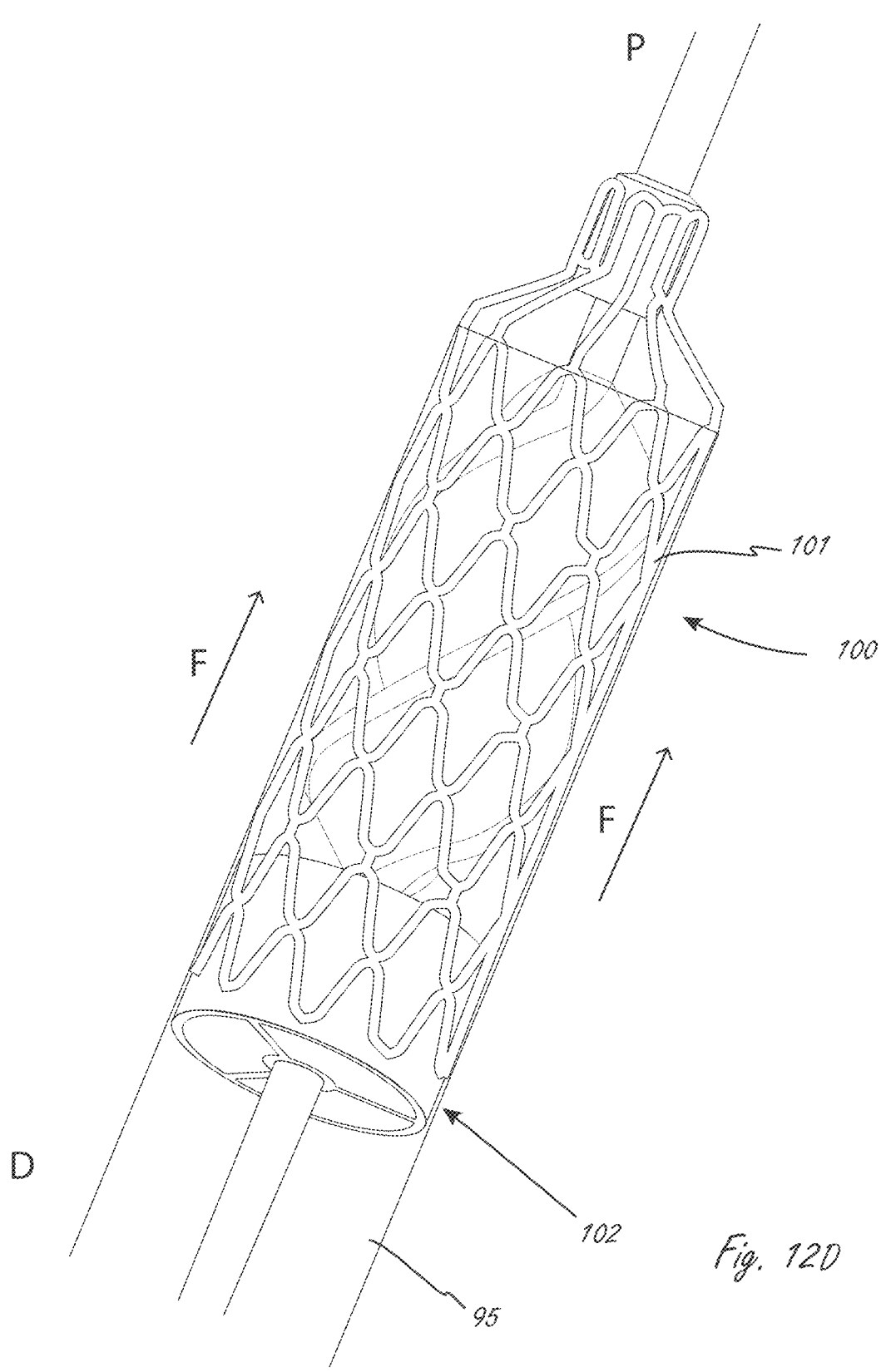

In other embodiments herein, the intermediate member may not extend along a substantial portion of the length between the impellers (see, for example, the intermediate members 92 and 102 in FIG. 12A). In any of the embodiments herein, the central member may extend no more than 5% of the central span between first and second impellers, or no more than 10%, or no more than 15%, or no more than 20%, or no more than 25%, or no more than 30%, or no more than 35%, or no more than 40%, or no more than 45%, or no more than 50%, or no more than 55%, or no more than 60%, or no more than 65%, or no more than 70%, or no more than 75%, or no more than 80%, or no more than 85%, or no more than 90%, or no more than 95%, or no more than 99%.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

The length of one or more central members can be any desired length between first and second impellers.

In some embodiments, at least 50% of the central member, by length, provides functionality that is considered more like a stator than a diffuser. For example only, in the embodiment in FIG. 10, the proximal half of central member 60 functions more as a stator than a diffuser. The diffuser section may have a length sufficient to recover at least 5-50% of pressure from kinetic energy created by the preceding stage (e.g., a distal impeller). The stator section can have sufficient length to direct the flow to the next stage (e.g., a proximal impeller) without creating excessive frictional losses.

While the embodiment in FIGS. 10-11C illustrates a single central member 60 in between the impellers, in some alternative embodiments the distal, or working, portion can include more than one discrete and axially spaced central members disposed in between the impellers. FIGS. 12A-13C illustrates such an exemplary design.

FIG. 12A is a perspective view of exemplary distal portion 80 of pumping apparatus 70. The embodiment in FIGS. 12A-13C is similar in some ways to the dual-impeller design shown herein with a plurality of expandable members (e.g., FIG. 3A). One difference between FIGS. 12A-13C and FIG. 3A is that distal portion 80 includes a distal central member 92 and a proximal central member 102, each of which are disposed closely next to one of the impellers. At least a portion of central member 92 is disposed axially within the ends of structural support 91 (e.g., a stent-like device), which is a part of distal expandable member 90. Central member 92 is also radially within structural support 91. At least a portion of central member 102 is disposed axially within the ends of structural support 101 (e.g., a stent-like device), which is a part of proximal expandable member 100. Central member 102 is also radially within structural support 101. Conduit 95 (which can have any of the conduit properties described herein) extends from a distal end to a proximal end, including extending axially between central member 92 and central member 102.

FIGS. 13A, 13B and 13C show end perspective, perspective, and side views of central members 92 and 102 (the other components are not shown for clarity). The central member include an outer annular member 110 and an inner annular member 113, between which a plurality of blades 112 extend.

Similar to central member 60 in FIG. 10, central members 92 and 102 are adapted and configured to provide fluid control and to provide structural support. Central members 92 and 102 are each disposed radially within and at least partially axially within the expandable members 90 and 100. The annular member 110 and radially extending blades 112 provides radial reinforcement and support, and can thus help keep the lumen open, maintain tip gap, and reduce vibrations between the impellers. In this embodiment, the blades are also configured such that central members 92 and 102 act as stators. For example, proximal central member 102 can direct the flow before it reaches the proximal impeller. Distal central member 92 can also help to recover pressure. "Direct the flow" and derivatives thereof as used herein can include altering the ratio of axial to radial flow components. For example, any stator functionality (and any components that function a stator) herein can increase axial flow components and reduce radial flow components.

In this embodiment a portion of the central span between the impellers does not include an expandable member or a support member, but does include conduit 95 (e.g., a flexible membrane). This is similar to the embodiment in FIG. 3A. Deformable conduit 95 may allow the central region to deform to some extent where valve leaflets are coapting. Support members 92 and 102, however, help reinforce the ends of the expandable members 90 and 100 even though the conduit 95 can deform in more central regions.

An additional difference between the embodiment in FIGS. 3A and 12A-13C is that in FIGS. 12A-13C, the expandable members do not have struts on the inner portion (closer to the middle along the longitudinal axis) of the expandable members. Central members 92 and 102 replace those struts.

Central members 92 and 102 are collapsible and expandable, just as are the impellers herein. Central members 92 and 102 are secured to a component passing through lumen 114 (see FIG. 13B), and are secured so that they do not rotate when the impellers rotate. A rotatable axle passes through the central members 92 and 102. Central members 92 and 102 are directly adjacent to the impellers, but spaced just enough to prevent any friction between the parts.

In other embodiments there can be more than two central members axially spaced apart and in between the impellers. For example, one or more separate central members could be disposed between central members 92 and 102, and, for example, secured to the same elongate shaft to which central members 92 and 102 are secured.

Central members 92 and 102 can be permanently affixed to expandable member 90 and 100, respectively, such that they expand and collapse together. For example, the radially outer surface of annular section 110 can be secured to the expandable member. Alternatively, central members 92 and 102 are not affixed to the expandable members, but the central members are sized to contact/engage the expandable members when both are in the their deployed configurations.

An axle that is operably connected to the impellers can extend through a shaft to which the central members 92 and 102 are secured, such that the axle can rotate within the non-rotating elongate shaft to drive the rotation of the impellers without causing rotation of the central members.

In some alternative embodiments not shown, aspects of the central members 92 and 102 can be incorporated into a single central member design. For example, the annular outer region 110 from which the blades 112 extend can also be incorporated into all or some portion of the length of a single central member. For example, in some alternative embodiments to FIG. 10, the central member 60 can include one or more annular outer regions anywhere along the length of central member 60. For example, central member 60 could include a single outer annular region that extends along its length, and blades 63, 64, and 65 can extend from the single outer annular region. Or, for example, central member 60 could include a plurality of annular outer regions disposed at any location along its length. For example, distal and proximal end regions of central member 60 can each include a discrete annular outer region from which the blades 63, 64, and 65 extend. The discrete annular outer regions can be of any desired length and occupy any desired percentage of the axial span between the impellers. Or, for example, the central member could also include a third discrete annular outer region in the center of central member 60. Additional discrete outer annular regions can be axially spaced apart along the length of central member 60 (or any other single central member).

In some alternative embodiments not shown, aspects of the central member 60 can be incorporated into a design that includes a plurality of central members (e.g., central members 92 and 102). For example, blades 112 in central members 92 and 102 (shown in FIGS. 13A and 13B) need not have straight configurations, but can be curved to some extent like portions of the blades 63, 64, and 65 shown in FIG. 10. Or, portions of the blades 112 can be straight and portions can be curved, such as are the blades 63-65 in FIG. 10. For example, distal central member 92 can have blades with curved portions, while proximal central member 102 can have straight blades. In these designs, central member 92 could act more to recover pressure, and proximal central member 102 could function more like a stator that directs flow.

Additionally, distal central member 92 need not have the same configuration as proximal central member 102.

Additionally still, in other embodiments, aspects of the distal regions 20 and 80 in FIGS. 10 and 12A can be incorporated with the other distal region. For example, in FIG. 10, support structure 33 extends across the entire central span between the impellers. In distal region 80 shown in FIG. 12A, a support structure can similarly extend across the span between central members 92 and 102. For example, distal support structure 91 could extend proximally into the central span and also form the proximal support structure 101.

The fluid pumps described with respect to FIGS. 10-13C can be positioned in any anatomical location described herein. In exemplary methods of use, the fluid pumps can be used in methods that position the devices as is shown in FIG. 4 when in use. The entirety of the description herein related to FIG. 4 is incorporated by reference for all purposes for the embodiments in FIGS. 10-13C. For example, fluid pump 10 can be placed across an aortic valve so the distal impeller is positioned in a left ventricle and the proximal impeller is positioned in an ascending aorta. In this position, the central region of the distal portion, including a portion of the control member 60, is positioned at the location of the aortic valve.

Any of the pump portions herein that include a plurality of impellers may also include more than two impellers, such as three, four, or five impellers (for example).

While some of the embodiments above describe pump portions or components that are collapsible and expandable (or at least movable between collapsed and expanded configurations), in any of those embodiments the components and expandable outer housing may also be non-expandable and non-collapsible. That is, any of the components in those embodiments may be present, but the components may be non-expandable variations of those components. For example, the impellers above may be non-expandable rather than expandable.

Figure 14A:
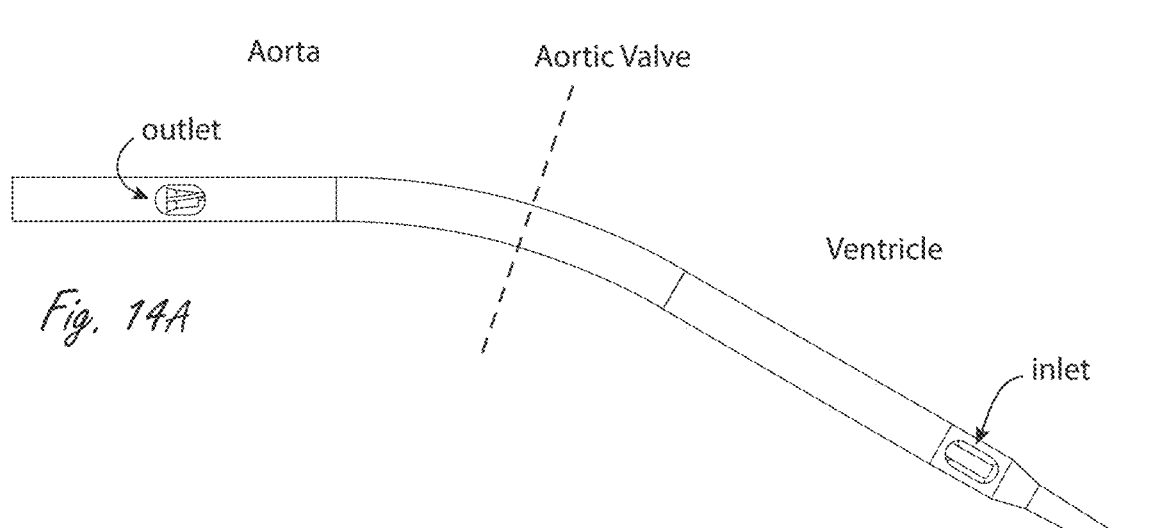
FIGS. 14A and 14B illustrate an exemplary blood pump in which at least the components that are shown are non-collapsible and are not collapsed for delivery.
Figure 14B:
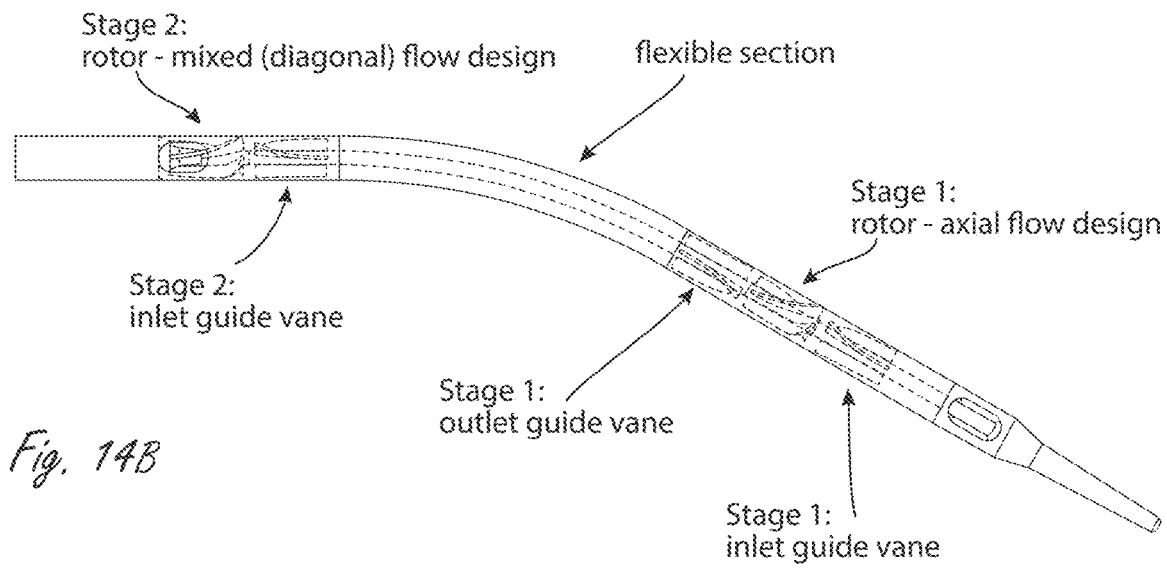

FIGS. 14A and 14B show side views of a distal portion of an exemplary embodiment of a blood pump in which the components are not expandable and collapsible. All the components in this embodiment can be rigid, fixed pieces.

FIG. 14B illustrates internal components that cannot be seen in FIG. 14A. The descriptions in FIGS. 14A and 14B are illustrative and not limiting. The pump portion shown in FIGS. 14A and 14B includes a Stage 1 section and a Stage 2 section, axially spaced apart along the length of the pump portion. In this embodiment the central section between the two stages (labeled generally as "Flexible section") has a bend formed therein, which may extend along any portion of the central section between the stages, such as at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The bend can be manufactured into the central region so that extracorporeally the bend is present, but the central region can be flexible enough so that it can reconfigured to a straightened delivery configuration within a delivery device such as a delivery sheath or introducer.

The pump portion includes a plurality of axially aligned inlet apertures distal to the Stage 1 components. There are two inlet apertures in FIGS. 14A and 14B, but there may be more than two inlet apertures. There are also two outlet apertures that are axially aligned with a portion of the Stage 2 rotor. The inlet and outlet apertures extend through a radially outer wall of the pump portion. Distal is to the right in the FIGS., and proximal is to the left in the FIGS. In various embodiments the pump portion includes a set of inlet apertures distal the Stage 1 components and a set of outlet apertures proximal the Stage 2 components. In various embodiments the pump portion includes a set of inlet apertures distal the distal pump and a set of outlet apertures proximal the proximal pump. In various embodiments, no apertures (for inlet or outlet) are between the Stage 1 and Stage 2 components. In various embodiments, no apertures (for inlet or outlet) are between the distal and proximal pump impellers.

Stage 1 in this embodiment includes a distal impeller (labeled as Rotor), an inlet guide vane distal to the rotor, and an outlet guide vane proximal to the distal rotor. The vanes (and any vanes herein) are considered generally to be flow modification elements or a derivative as that term is used herein. Any of the vanes and rotors can include a hub and extending blades as shown, or can include other known impeller and stator/vane designs. The vanes (and any flow modification components herein) are positioned closely next to the distal impeller, such as less than 10 mm away (along the length of the device), or less than 9 mm away, or less than 8 mm away, or less than 7 mm away, or less than 6 mm away, or less than 5 mm away, or less than 4 mm away, or less than 3 mm away, or less than 2 mm away, or less than 1 mm away. "Closely" as used herein can include any of these axial distances. "Closely" as used herein can also refer to a distance less than two times a diameter of the central lumen.

Stage 2 in this embodiment includes a proximal impeller (rotor) and an inlet guide vane distal to the proximal impeller. All of the disclosure above related to the vanes in Stage 1 is incorporated and can be incorporated into Stage 2 vanes.

In this example, the Stage 1 (distal) rotor is configured as an axial flow impeller, and proximal impeller (Stage 2) is configured as a mixed (diagonal) flow impeller, but these are illustrative and other impeller designs can be used for either impeller.

The pump portion in this embodiment includes a flexible outer housing between the stages. The flexible outer housing can be, for example, a flexible polymeric material that is formed with a slightly degree of curvature and can be straightened for delivery, and is coupled to the distal stage and proximal stage sections. In some embodiments the flexible central section could be a very thin walled rigid material, which imparts some flexibility. In other embodiments, for example, the flexible section could include a plurality of elongate support members (e.g., nitinol wires) to which a flexible membrane is attached. The elongate support members can be formed with bends therein and spaced around the periphery of the flexible section, so that the flexible membrane forms a lumen therethrough. In some embodiments, the flexible section can include a laser cut tube (e.g., laser cut polymeric or metallic material, e.g., nitinol) with one or more slots cut out in at least a section to impart flexibility (e.g., creating a spine along one side with ribs extending around at least a portion of the periphery, the ribs formed by cutting out material), and a membrane like material can be affixed to the slotted tubular member to cover the removed material. The flexible material could also include a stent like device that is configured with a bend, and a membrane like material covering the stent apertures.

As used herein, "axially spaced" includes embodiments in which a bend exists in the outer profile (e.g., FIGS. 14A and 14B), wherein a bend can be included in any of the embodiments herein. Axially spaced as that phrase is used anywhere herein is meant to refer to spacing along the device, even if there is a bend in the outer profile of the pump portion (e.g., FIGS. 14A and 14B). It may refer to spacing along a longitudinal axis of the pump portion, for example.

In alternative embodiments to that shown in FIGS. 14A and 14B, not all components shown need to be included. For example, any of the vanes may not be present, depending on flow needs.

Any of the other disclosure herein related to any aspect of a pump device or method of use (e.g., external motors, placement when used) is incorporated by reference into the embodiments in FIGS. 14A and 14B.

The description shown in FIG. 14A illustrates an exemplary placement of the device, showing surrounding/ambient anatomy. The distal impeller can be positioned in the left ventricle while the proximal impeller is positioned in the ascending aorta, and the impellers can be spaced accordingly.

Blood pumps, such as any of the intravascular pumps herein, may benefit from having one or more fluid paths through which fluid can flow through the device. For example without limitation, blood pumps may benefit from having one or more fluid paths through which fluid can flow to perform any of these exemplary functions: cooling rotating components (e.g., a drive cable) to prevent their overheating; flushing small particulates that may break off rotating components (e.g., a drive cable) to prevent the rotating parts from being damaged by the small particulates; lubricating rotating components (e.g., one or more bearings), and preventing blood ingress into the pump (e.g., near or at a distal end of the pump). Fluid delivery through the one or more flow paths may provide any number of these functions.

Figure 15A:
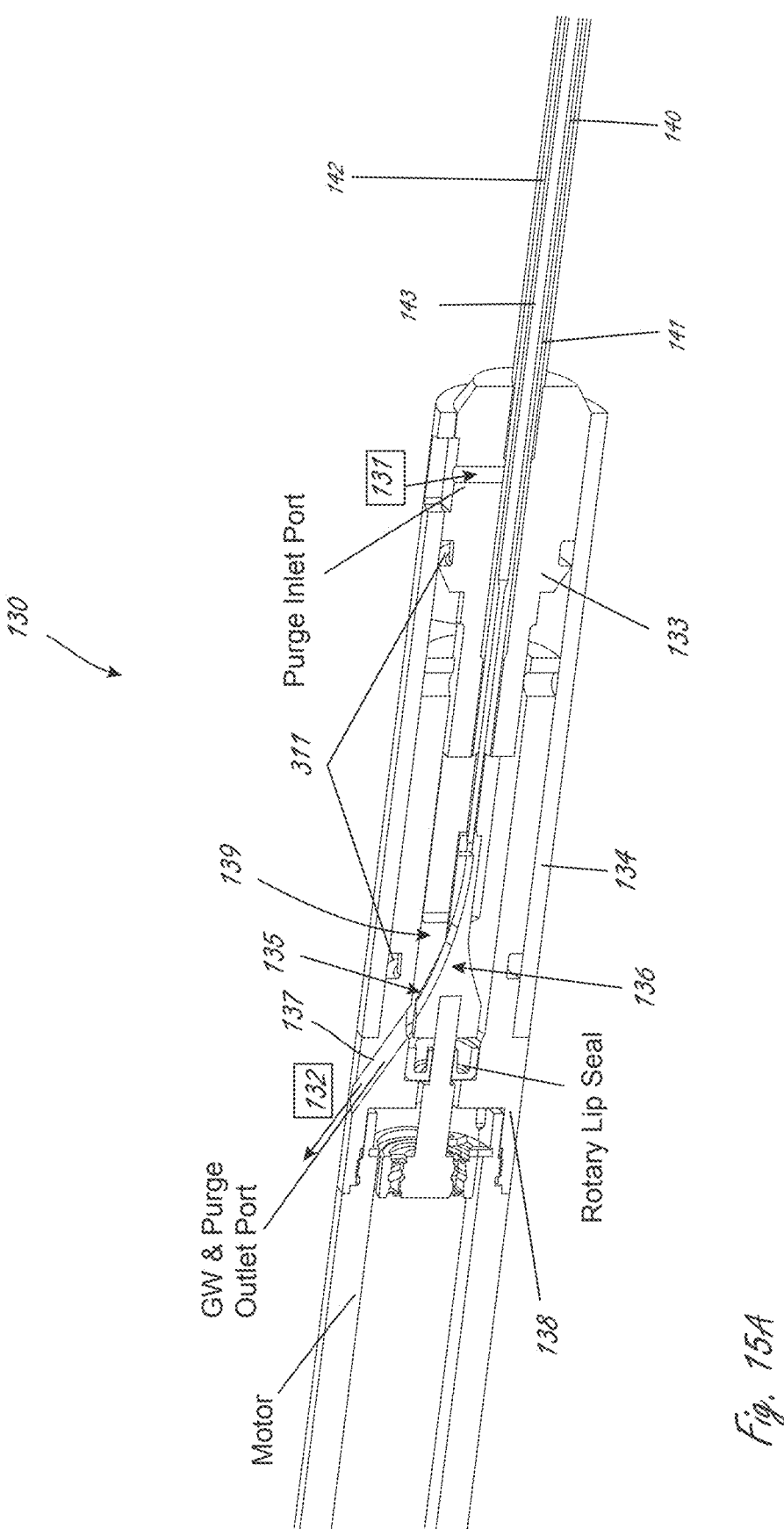

FIGS. 15A-15D illustrate an exemplary embodiment of a fluid delivery system incorporated into an exemplary fluid pump (e.g., blood pump) with a fluid inlet port and a fluid outlet port. FIG. 15A illustrates a portion of the device that is proximal to the one or more impellers, and in this embodiment includes a proximal end of a catheter, a motor assembly that causes the rotation of a drive cable and impeller(s), a fluid inlet port, and fluid outlet port, and a guidewire port that allows access to a guidewire pathway or lumen.

Figure 15B:
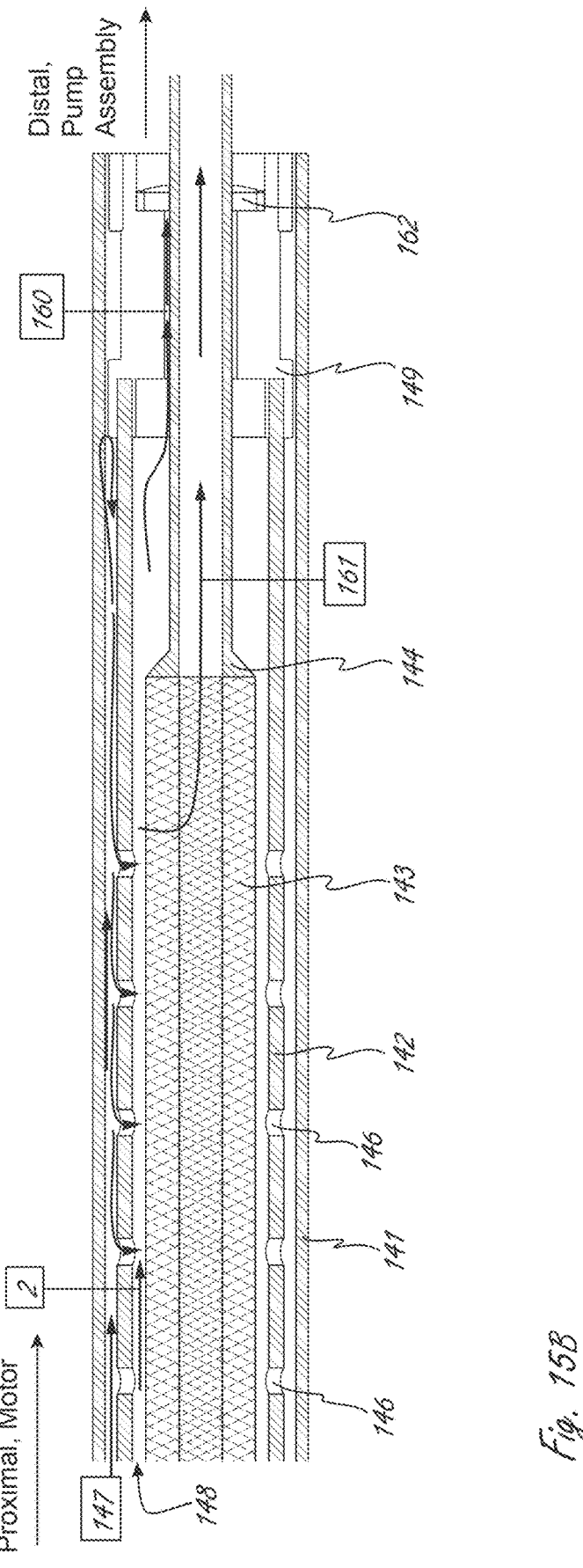
Figure 15C:
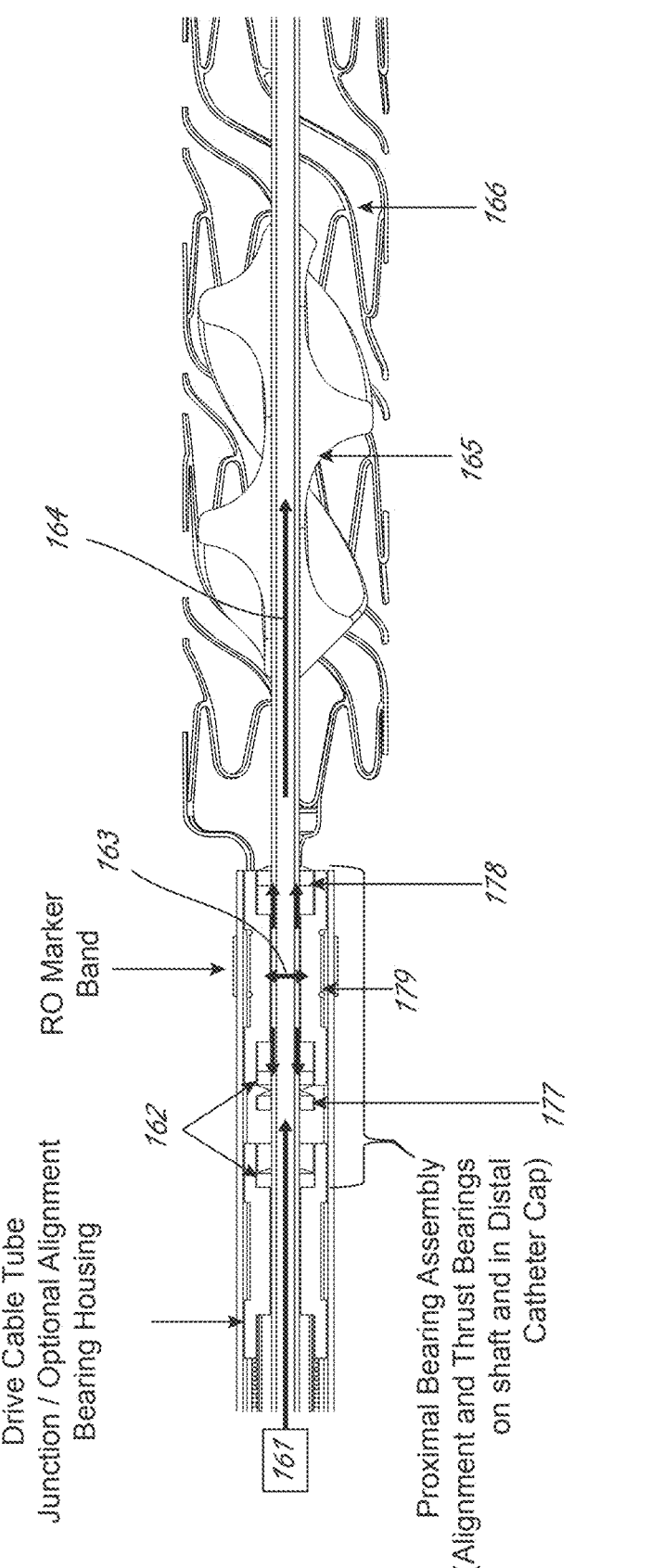
Figure 150:
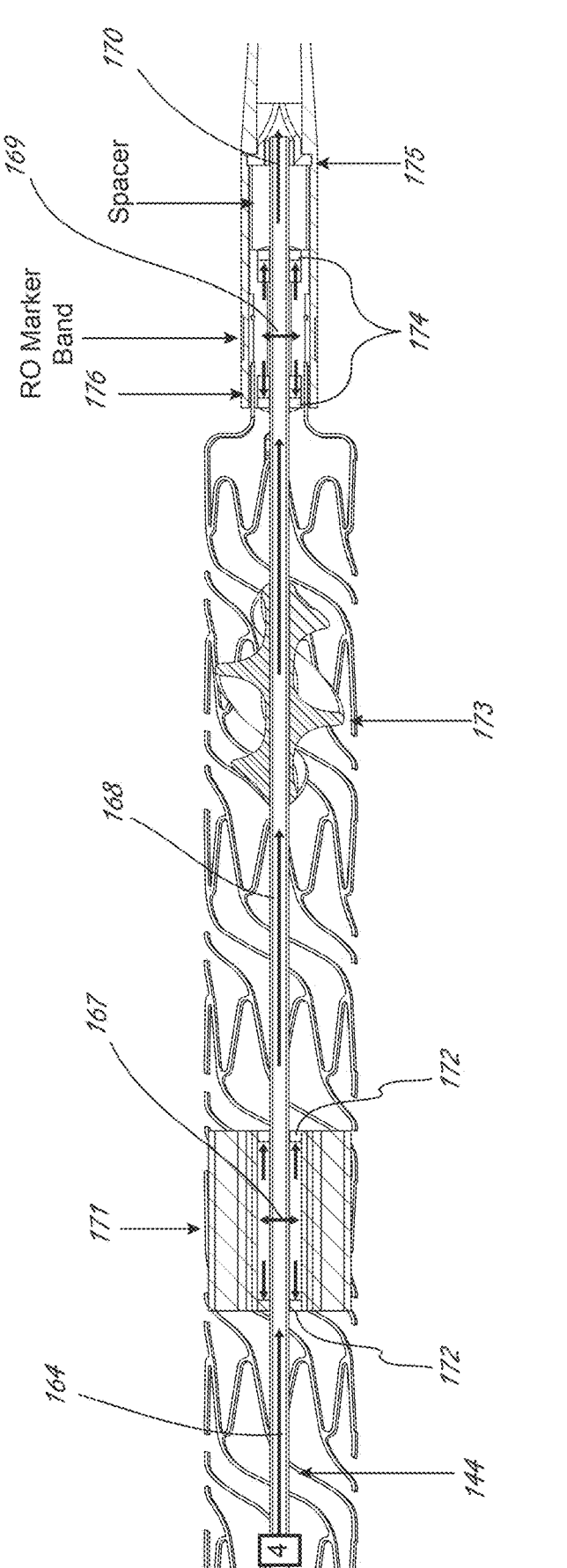

FIG. 15B shows a region of the device that is distal to the region shown in FIG. 15A, but includes some of the catheter components that are shown in FIG. 15A. FIG. 15C shows a region of the device distal to the region in FIG. 15B, and FIG. 15D shows a region of the device distal to the view in FIG. 15C.

While FIGS. 15A-15D illustrate different sections of an exemplary blood pumping device, it is understood that in alternative embodiments aspects of the system can vary. For example, in alternative embodiments the portion of the device with the impellers can vary and could only include a single impeller, or the expandable housing around the impeller could have a wide variety of configurations. It is understood that individual regions of the device can be incorporated by themselves into a variety of different types of blood pumps.

One aspect of this exemplary embodiment includes a guidewire access port that also functions as a fluid port, and in this embodiment a fluid outlet port. A motor sealing cap 138 includes, formed therein, a guidewire channel 137, including a guidewire port in a radially side surface that provides access from outside the device to channel 137. The motor sealing cap may be an optional component, and the guidewire channel 137 can alternatively be formed in a different part of the device (e.g., which may not function as a motor sealing cap). The device also includes drive cable coupler 135, which includes formed therein a guidewire channel 136, which is a portion of a guidewire pathway. Drive cable coupler 135 is rotated by the motor, and causes the rotation of drive cable 143, which causes rotation of the one or more impellers in the pump portion. These components are thus considered to be in rotational communication. Channel 137, including the guidewire port, is formed in the device and is not adapted to rotate when the motor rotates. Channel 136 formed in drive cable coupler 135 rotates when the drive cable coupler rotates. When drive cable coupler 135 is in the position shown in FIG. 15A, channel 137 is in alignment with channel 136, which allows a guidewire to be advanced through or removed from channel 137 and through channel 136. If the guidewire is being inserted, the guidewire can then be advanced further distally through the entire device and out a distal end, described in more detail below. As is also described in more detail below, the guidewire access port also acts as a fluid outlet port that allows return fluid to flow from return area 139 out of the outlet port.

One of the advantages of having the guidewire access port (part of channel 137) in the location that it is in this embodiment, is that, if needed after the pump portion has already been advanced to a location within the patient, a guidewire can be reinserted into the port and inserted all the way to and out of the distal end. Importantly, the guidewire can be reinserted without having to remove most of the device from the patient like with some rapid exchange designs, and without having to remove the motor assembly. This exemplary embodiment thus allows easy reentry of a guidewire without having to remove the motor assembly, and without having to remove the device from the subject.

Being able to reinsert the guidewire during use can be advantageous because it can, for example without limitation, allow for repositioning of the pump portion if desired or needed. For example, if the pump portion moves out of position relative to an anatomical landmark (e.g., an aortic valve), a guidewire may need to be inserted to safely reposition it relative to the anatomical landmark.

Because the guidewire path extends through a rotational component (e.g., drive cable coupler 135), it is important that the guidewire not be present in the guidewire path when the rotating component is active. The apparatuses herein can also include an automated sensing mechanism to detect the presence of the guidewire in the guidewire pathway, and/or a prevention mechanism that prevents the motor from being activated if the guidewire is in the lumen. For example without limitation, there could be a sensor that can selectively detect the presence of the guidewire in the guidewire pathway, and communicate that to a controller that prevents the motor from being activated.

In this embodiment there is a single fluid inlet channel or lumen 131 into which fluid can be delivered into the device. FIG. 15B illustrates a region of the device and illustrates different pathways the fluid can take after it has been delivered into the device. After the fluid is advanced into fluid inlet port channel 131 (which includes an inlet port), it travels through a space 147 between clean purge tube 141 and drive cable tube 142. This is considered clean input fluid. This pathway deadends at distal catheter cap 149. The fluid passes through the one or more apertures 146 formed in a distal region of drive cable tube 142 as shown in FIG. 15B, entering into an annular space between drive cable tube 142 and drive cable 143. Some of this fluid (optionally most of the fluid) returns in the proximal direction through this annular space, lubricating and cooling drive cable 143 and flushing potential particulate along its path. This return fluid continues to flow proximally and into area 139 shown in FIG. 15A, and continues to flow through channel 137 and out of the fluid port (which is also the guidewire access port). A fluid outlet port thus also functions as a guidewire access port in this embodiment.

While most of the fluid returns proximally to area 139, some of the fluid, after it passes through apertures 146, continues distally beyond the distal end of the drive cable 143. Some of the fluid follows proximal bearing path 160 through alignment bearing 162 to prevent blood ingress. Fluid flow along path 160 to bearing 162 can be controlled by, for example, controlling input flow pressure and throttling of the return fluid at the proximal region of the device.

Some of the fluid, after passing through apertures 146, will flow through drive cable 143, along path 161, and will continue distally through the device (e.g., through hypotube 144) and out holes to lubricate any rotating surfaces and to prevent blood ingress, described in more detail below. Guidewire lumen 145 is thus positioned to also function as a distal bearing fluid flow path.

Some fluid flows distally along path 161, as shown in FIG. 15C, and passes through holes along path 163, to lubricate one or more of bearings 162, thrust bearing 177, and alignment bearing 178. Some of the fluid continues distally in the direction of arrow 164 shown in FIG. 15C, through impeller 165 (which in this embodiment is a proximal impeller). Some of the fluid passes through apertures along path 167 to lubricate optional alignment bearings 172 that support central member 171, which may be any of the collapsible support members, including any of the central or intermediate members herein. Some fluid continues distally through the guidewire lumen in the direction of arrow 168, through optional distal impeller 173. Some fluid passes through holes along path 169 to lubricate bearings 174 that are distal to the distal impeller. Some of the fluid may also flow through valve 175 and out the distal end of the device, helping prevent blood ingress.

In this exemplary embodiment a single flow path flowing through a tubular member (path 161 that extends distally through guidewire lumen shown in FIG. 15B) leads to (is in fluid communication with) at least three distally located bearing lubricating fluid paths, 163, 167, and 169, which lubricated three axially spaced bearing regions. In some alternative embodiments, there may be a single bearing region that is lubricated, two bearing regions that are lubricated, or even more than three bearings regions that are lubricated, depending on the number of structures disposed within the expandable housing that require bearings and thus lubrication.

An exemplary method of using the device in FIGS. 15A-D includes inserting a guidewire near a target location (e.g., into a left ventricle via femoral artery access), then feeding the distal guidewire port over the guidewire and advancing the device over the guidewire towards the target location (e.g., an aortic valve). The method can also include removing the guidewire from the guidewire path, and coupling the proximal portion shown in FIG. 15A to a fluid inlet coupler and a fluid outlet coupler at the inlet and the outlet fluid locations, respectively. The motor can be activated to activate the one or more impellers. If the guidewire needed to be reinserted, the fluid out connector can be removed and a guidewire can be reinserted (e.g., for repositioning). The guidewire can then be removed and the fluid outlet coupler can again be put into fluid communication with the guidewire pathway. These methods or any of them individually can be incorporated into the use of any of the suitable devices herein, such as the device in FIGS. 16A and 16B. Additionally, any of the steps in any of the other exemplary methods of use herein, such as those below, may be incorporated into a use of the blood pump in this embodiment.

Figure 16A:
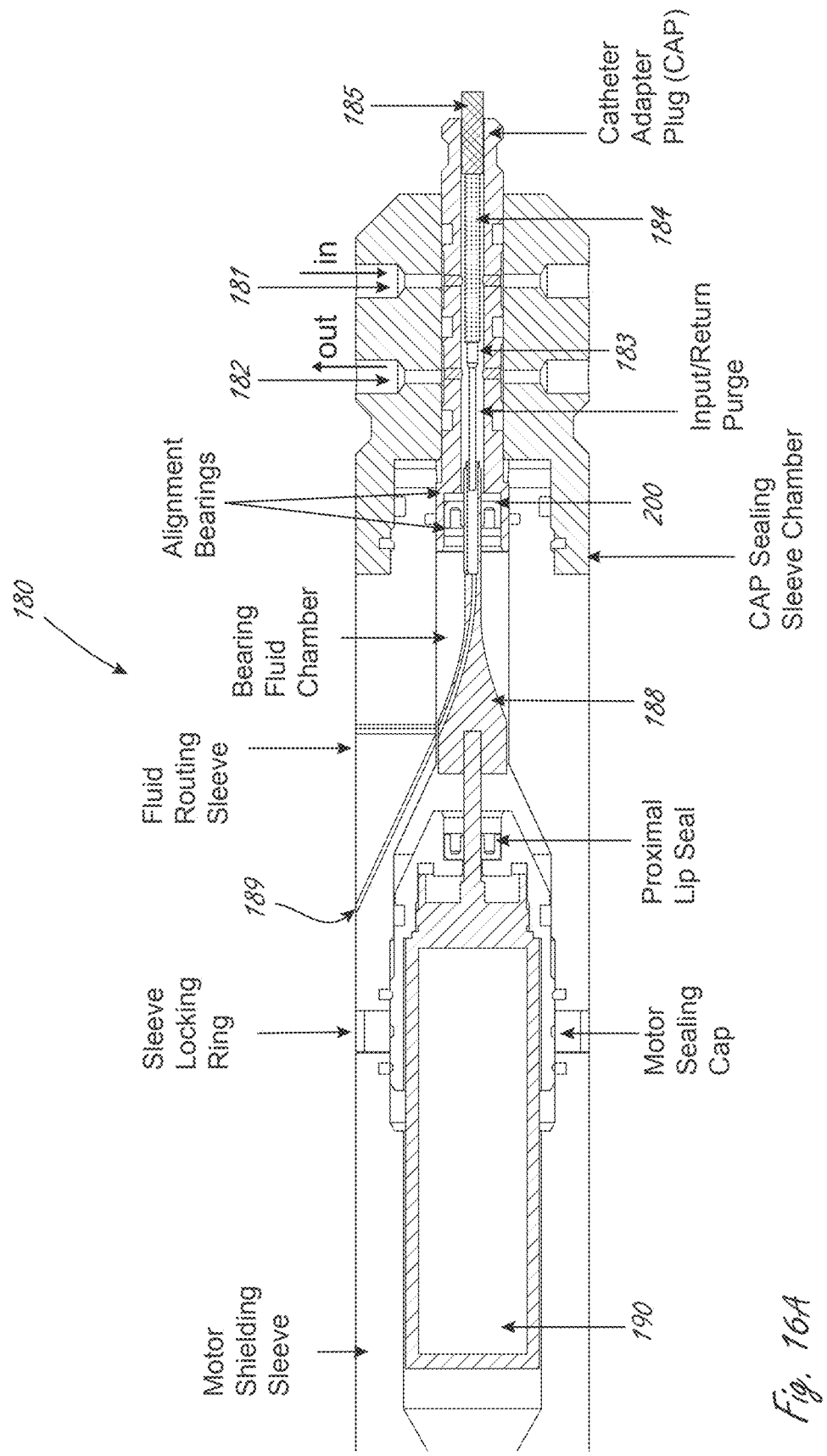
FIGS. 16A and B illustrates an exemplary blood pump that includes a guidewire pathway and at least two fluid purge pathways that are not in fluid communication.
Figure 16B:
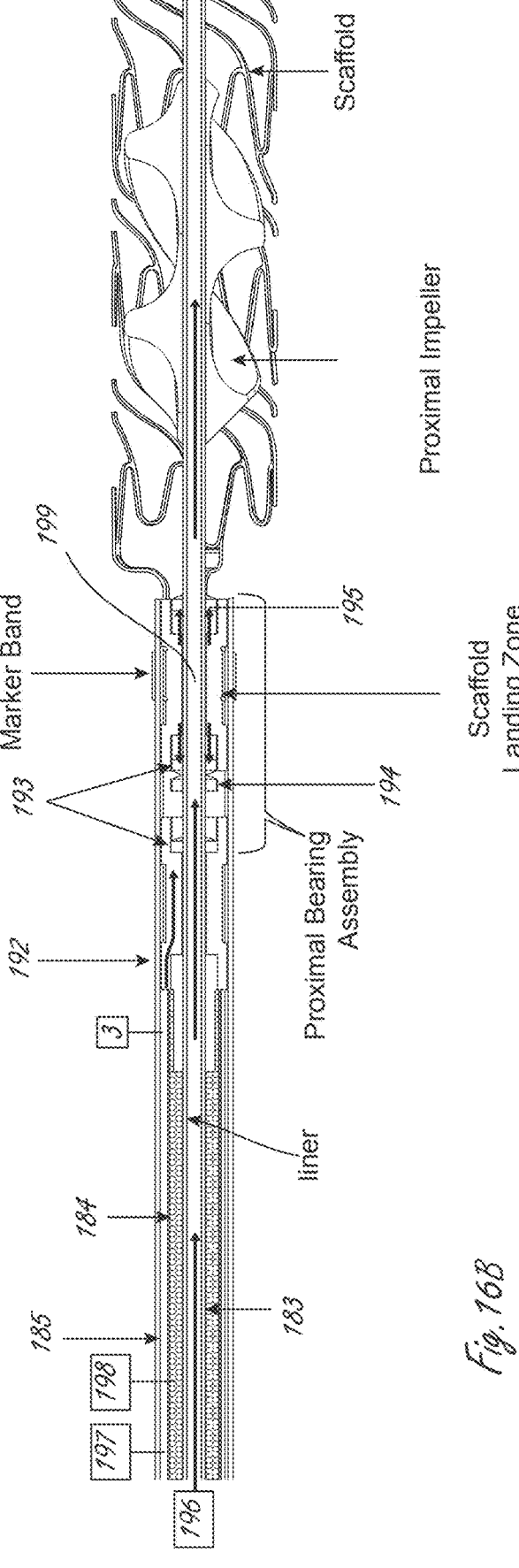

FIGS. 16A and 16B illustrate an exemplary embodiment of a fluid delivery system incorporated into an exemplary fluid pump (e.g., blood pump) with a first flow path with a first fluid inlet port and a first fluid outlet port. In this embodiment, however, there is also a second fluid flow path that is not in fluid communication with the first flow path. The device 180 in FIGS. 16A and 16B is similar to that shown in the embodiment in FIGS. 15A-D, except in this embodiment the fluid path 161 from FIG. 15B does not originate as fluid that flows through the drive cable. In this embodiment the fluid flow path that includes the guidewire lumen (see fluid path 196 in FIG. 16B) is in fluid communication with a separate and second fluid inlet port 189, which is also located to function as a guidewire access port, as shown in FIG. 16A. Drive cable 183 has a drive cable liner 187 on its inner surface to seal off the distal bearing flow path 196 (through the guidewire lumen). In this embodiment the guidewire access port does not function as a fluid outlet, like in FIGS. 15A-D, but as a fluid inlet port, and thus still functions as a fluid port or fluid access.

The blood pump also includes a first fluid path that includes inlet port 181 and outlet port 182 as shown in FIG. 16A. This flow path is very similar to the path in FIGS. 15A-D, except that it does not include the path through the drive cable and hypotube (i.e., does not include the guidewire lumen). The fluid is advanced through port inlet port 181, flows distally along path 197 in FIG. 16B, which is between clean purge tube 185 and drive cable tube 184. This path deadends at a distal catheter cap, just as in the embodiment in FIGS. 15A-D. The fluid flows through holes in drive cable tube 184, and returns proximally in the annular space between drive cable tube 184 and drive cable 183. In this part of the path the fluid lubricates and cools the drive cable and flushes potential particulate along its path, carrying them proximally to fluid exit port 182 shown in FIG. 16A. Seal 200 prevents fluid from passing proximally to seal.

Fluid flowing through the first fluid path thus lubricates and cools the drive cable, as well as flushes potential particulates and returns to exit port 182. Fluid flowing through the second fluid path travels further distally through the system, and lubricates one or more distal bearings, just as in the embodiment in FIGS. 15A-D. For example, path 199 shown in FIG. 16B is the same as path 163 in FIG. 15C, which lubricates bearings in that bearing region. While not shown, the fluid flow path distal to the view shown in FIG. 16B can be exactly the same as in FIG. 15D, thus lubricating additional bearings, and optionally exiting through a valve at a distal end of the device. This second flow path can thus also prevent ingress of blood, which is described more fully in FIGS. 15A-D.

In any of the devices herein, the pump portion can include a distal end valve distal to the impeller to seal off the distal guidewire port after the guidewire is removed, but allows for guidewire reinserting therethrough.

Figure 17F:
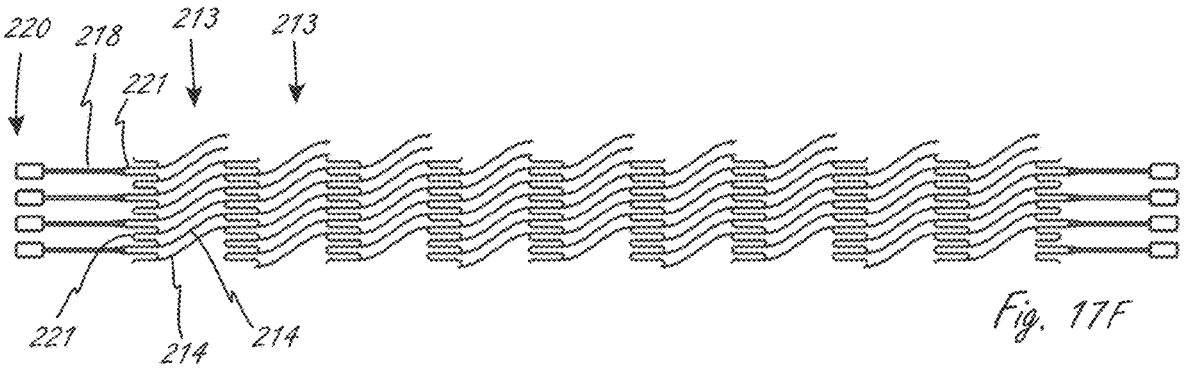

FIGS. 17A-17F illustrate exemplary pump portion 201 of an exemplary blood pump. Pump portion 201 can be used interchangeably with any other aspect of the any of the blood pumps herein. Pump portion 201 is also shown in the embodiments in FIGS. 15A-16B, and thus any features or methods of use described therein are incorporated by reference into this embodiment. Additionally, not every aspect of this embodiment needs to be included, and instead, any suitable feature(s) in pump portion 201 may be replaced with a different feature or method of use from a different suitable embodiment or part of this disclosure. For example, either impeller in pump portion 201 can be replaced with any suitable impeller from any other part of this disclosure. FIG. 17A is a side view, and FIG. 17B is a sectional side view.

Pump portion 201 includes drive cable tubular member 204, to which distal impeller 203 and proximal impeller 202 are secured. Rotation of drive cable tubular member 204, via rotation of the drive cable (not shown), causes rotation of the impellers. More or fewer than two impellers may be included in the pump portion.

Pump portion 201 also includes a collapsible housing 205, which includes collapsible support structure 206 (which may be referred to herein as a scaffold) with proximal end 210 and distal end 211, and conduit 212 (see FIG. 17E), which forms a fluid lumen between a distal end and a proximal end of the fluid lumen.

Pump portion 201 includes optional intermediate (which may be referred to herein as central, or in between impellers) member 209 between two impellers, which may be any central member or members herein.

In any of the embodiments herein, the distal impeller can have a length that is less than a proximal impeller, such as is shown in the device in FIG. 17A.

FIG. 17C is a side view of a proximal portion of support structure 206 in an expanded configuration (other parts not shown for clarity). FIG. 17D is a proximal end view of the support structure. The region shown is generally surrounding impeller 202 in FIGS. 17A and B. Support structure 206 can be formed using a variety of techniques, such as laser cutting a tubular starting material. Support structure 206 includes a plurality of arms (four in this embodiment) that, at the proximal region, transition from a larger diameter to a smaller diameter in regions 218. Each of the arms has a bend in regions 219, and is vertical in between the bend regions, as shown. The vertical region can help stabilize the transition region between the larger diameter and smaller diameter regions, and reduce and preferably eliminate the influence on the fluid at the outflow.

In the larger diameter region of the support structure, the support structure 206 includes staggered peaks 221 (only two are labeled), alternating every other peak. Staggered in this context refers to the axial location of the end of the peak. Each of the four arms forms a peak that extends further proximally than adjacent peak. The staggered peaks can facilitate sheathing and offset packing volume during collapse of the pump portion. A peak as used herein may also be considered a valley depending on the orientation, similar to how convex and concave are relative terms.

Support structure 206 also includes a plurality of hub features 220 that are each configured to stably bond to a component 222 (there are four in this embodiment) at a distal region of scaffold landing zone 179 (see FIG. 17E). Hub features 220 can constrain axial movement along bearing hubs.

Support structure 206 also includes axially spaced helical regions 213 (only some are labeled in FIGS. 17A and 17B) that include a plurality of arms (or portions of arms) that have helical configurations. In FIG. 17C, helical region 213 includes helical arms 214 (only four are labeled). In this embodiment, the helical arms extend between adjacent non-helical regions of the support structure. The regions in between the helical regions can have any number of configurations, and exemplary configurations are shown. In this exemplary embodiment, proximal impeller 202 axially overlaps with a least a portion of two adjacent helical regions 213, and distal impeller axially overlaps with at least a portion of two adjacent helical regions 213. Any impeller can axially overlap with one or more helical section 213. The pitch of the helical arms can vary.

FIG. 17F illustrates the scaffold design from FIGS. 17A-E in a flattened planar view to further illustrate the scaffold pattern. Only some of the portions of the scaffold are labeled for clarity.

The axial length of one or more helical regions 213 can be shorter than an axial length of an impeller with which it axially overlaps. For example, in FIG. 17E, the helical regions 213 are each shorter than the overall length of the impeller. The axial length of the helical regions 213 is also less than the length of distal impeller 203, even if a single helical region does not completely axially overlap with the impeller.

The configuration, or shape, of the plurality of helical arms can generally follow the helical shape of outermost regions of the impellers (e.g., outermost regions of helical blades) and are configured, relative to the blades, to facilitate sheathing to facilitate rotational sheathing and radial compression. Stated alternatively, the scaffold and any given blade can have strut patterns (and in particular helical arm configurations) and camber lines (a segment of one is labeled "CL" in FIG. 23), respectively, that when sheathed and unsheathed, can twist each component in a complimentary manner to perform one or more of reducing sheathing force, enhancing packing efficiency, and reducing component strains. The camber lines of the blades can generally follow the helical configuration of at least one of the helical arms in the helical regions, which can be seen in FIG. 17E, and wherein a segment of a camber line CL for one blade is shown in FIG. 23. In a side view of the pump portion (e.g., FIG. 17E or FIG. 23), and in some embodiments, a helical element and a blade can overlap at one or more locations, and a tangent "T" of the helical element and the blade camber line at the overlap location (see FIG. 23) can form an angle of 45 degrees or less, 35 degrees or less, 20 degrees or less, 15 degrees or less, or even 10 degrees or less.

There may be any number of helical regions 213 axially spaced along the support structure. Adjacent helical regions need not be equally spaced apart along the entire length of the scaffold.

In some exemplary methods of sheathing, the method may optionally include a collapsing process that includes a rotational movement of the component to which the support structure is coupled, which can be controlled by an actuator disposed outside the patient (e.g., on a handle).

In some embodiments the four proximal arms (generally labeled 218) can be inverted, such that the bend at the larger diameter portion is at a location that is further proximally than the bend at the smaller diameter portion.

The design of the scaffold in the embodiment in FIGS. 17A-17F provides a number of advantages compared to other scaffold designs. For example, the staggered proximal valleys 221 (which can also be present on the distal end of the scaffold) reduces the packing volume of the scaffold at the location of the staggered peaks. Additionally, when bent, the scaffold resists kinking and maintains a smooth curve in the bent section. This can be advantageous when placed at a target location which requires the scaffold to assume a bent configuration, such as when the scaffold is placed and extends from an ascending aorta to a left ventricle. Additionally, the design is a closed cell design (there aren't any free ends in the design; every end is connected to another section) yet retains sufficiently flexibility along the length of the scaffold. This design also includes struts that are individually terminated at the hub (proximal end of the scaffold), rather than coupled to other struts. The disconnected struts at the hub improves the manufacturing process of heat treatment, membrane coating and impeller loading. The advantages of the helical connecting members is set forth elsewhere herein.

While the scaffold design in FIGS. 17A-17F provides at least the exemplary advantages set forth herein, other scaffold designs are contemplated, and while some possible drawbacks of these alternative designs are discussed below, they (or aspects thereof) may still be used in pump portions herein. For example, depending on a particular application, one or more features may be less important than others.

Figure 18A:
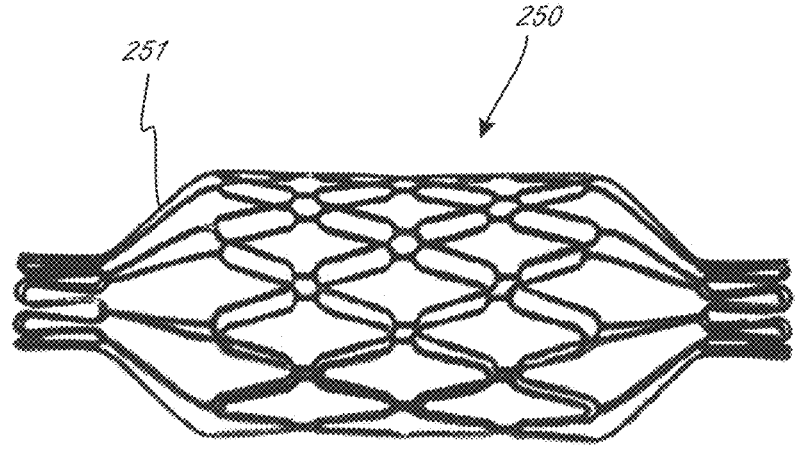
FIGS. 18A and B illustrate an exemplary scaffold design.
Figure 18B:
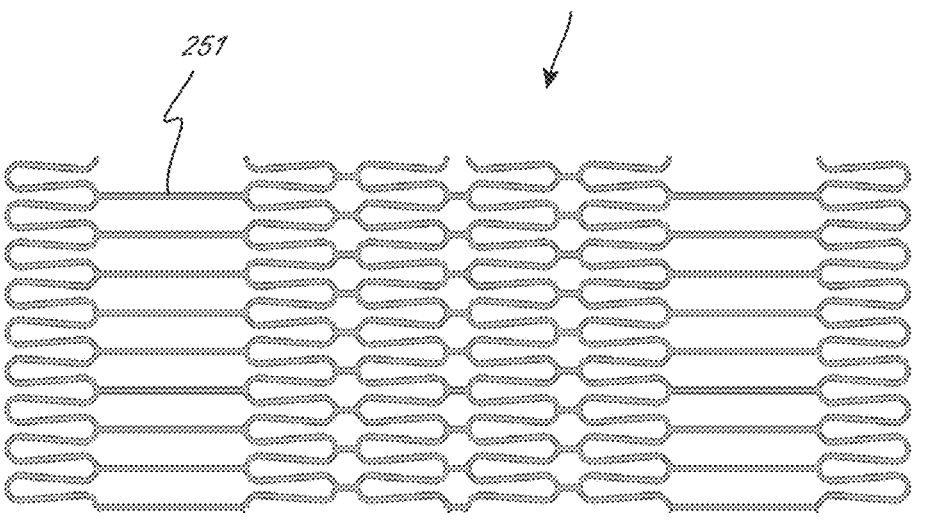

FIGS. 18A-B illustrate an expandable member 250 that is one of at least two expandable members (which may also be referred herein as collapsible housings), such as the expandable members in FIGS. 3A-3D, wherein each expandable member surrounds an impeller. The scaffold design in FIGS. 18A and B has more proximal struts 251 (only one labeled) than the design in FIGS. 17A-17E (in this exemplary embodiment there are nine compared to four). Having a separate expandable member 250 for each impeller provides for the ability to have very different geometries for any of the individual impellers. Additionally, this design reduces the amount of scaffold material (e.g., Nitinol) over the length of the scaffold (compared to other full length scaffolds herein), which may offer increased tracking when sheathed). A potential challenge with this design may include creating a continuous membrane between the expandable members in the absence of an axially extending scaffolding material (see FIG. 3A). Additionally, a relatively higher number of proximal struts 251 in the outflow path may disrupt the outflow more than designs with fewer numbers of struts, such as the four struts in the embodiment in FIGS. 17A-F. Any other aspect of the expandable member(s) herein, such as those described in FIGS. 3A-3D, may be incorporated by reference into this exemplary design. FIG. 18B shows a planar view of the scaffold in a non-expanded configuration to further illustrate the design.

Figures 19A, 19B:
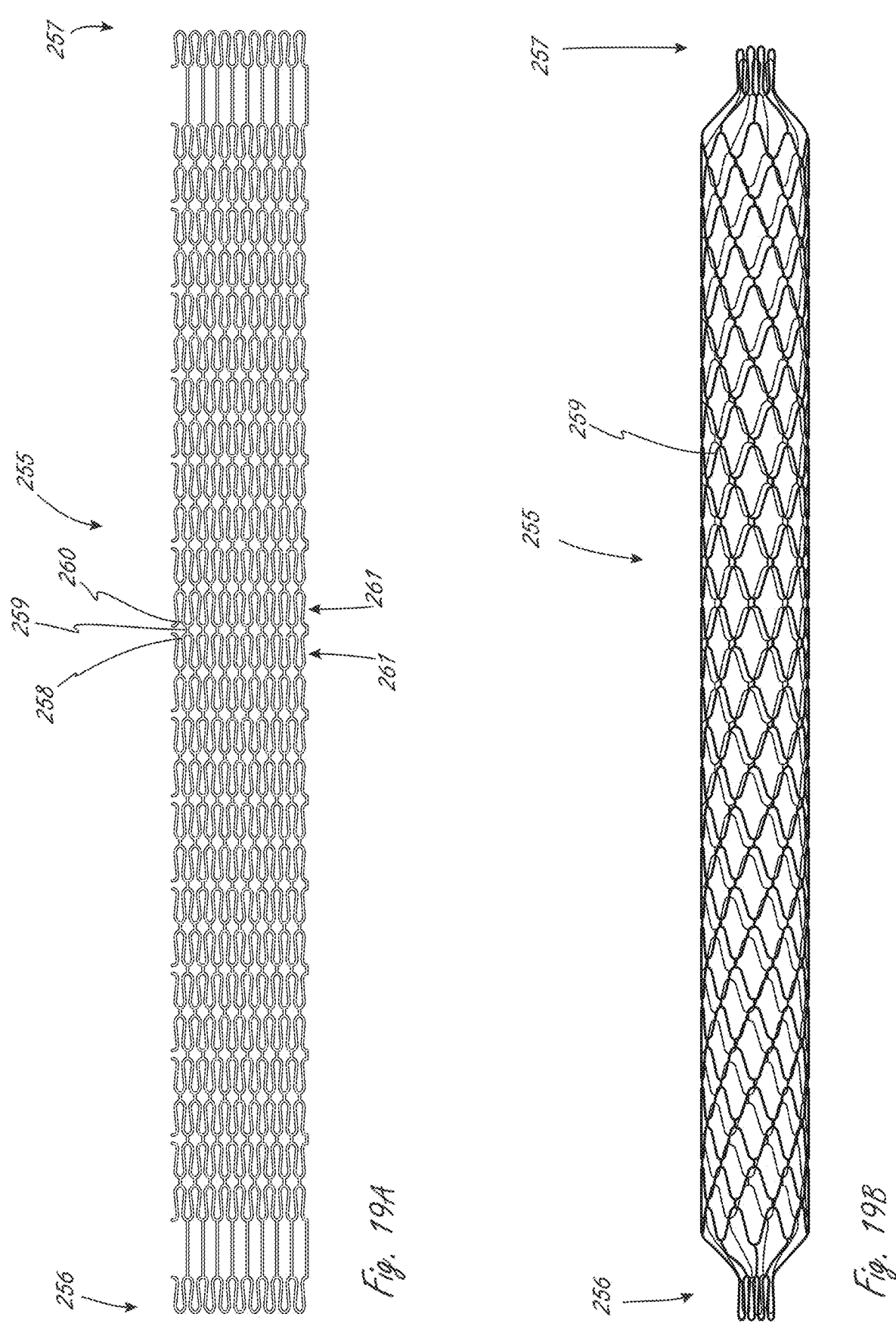
FIGS. 19A and 19B illustrate an exemplary scaffold design.

FIGS. 19A and 19B illustrates a scaffold design that has the same general pattern as in FIGS. 18A and B, but the scaffold pattern is not separated into two discrete sections, but rather the scaffold is a single elongate member as shown. FIG. 19A is a planar view of the unexpanded scaffold, while FIG. 19B is an expanded configuration. The scaffold design in FIGS. 19A and B has proximal end 256 and distal end 257 (i.e., the hub coupling regions) that have continuous, integral formations, rather than the independent proximal hub ends as in the design in FIGS. 17A-F. It may be easier to apply (e.g., coat) a membrane to the single scaffold in this design and the design in FIGS. 17A-F (compared to, for example, the separate axially spaced expandable members such as in FIGS. 18A-B). An exemplary drawback may be the relatively higher number of proximal struts (nine in this embodiment), which like the design in FIGS. 18A-B may disrupt the outflow as the blood exits the fluid lumen. This particular pattern may also be too rigid for some applications or access routes where more increased bending and flexing are desired. This design is relatively rigid over the axial length, and does not bend or flex with great ease. In this design, each peak 258 and valley 260 in adjacent sections 261 are radially aligned and are coupled by connector 259, which is parallel with a longitudinal axis of the fluid lumen.

Figure 20:
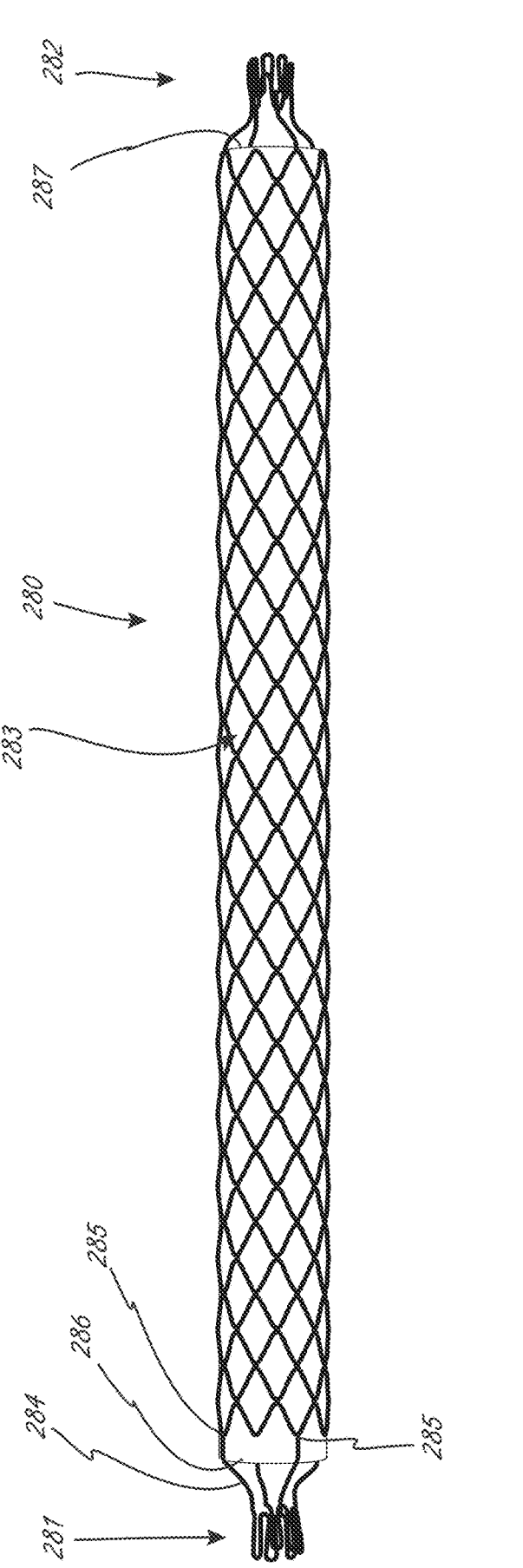
FIG. 20 illustrates an exemplary scaffold design.

FIG. 20 illustrates an exemplary scaffold 280 that extends along the entire axial length from the proximal hub end 281 to a distal hub end 282, and wherein the hub regions have the same design as in FIGS. 19A and B. The cells 383 (only one labeled, which have a diamond pattern in the expanded configuration) in this design have a reduced size compared to the designs in FIGS. 18 and 19. The number of struts 284 in this design is also less than that in FIGS. 18 and 19 (e.g., four at each end in this design, compared to nine), which in this embodiment means that every other peak 285 (only two are labeled) at the scaffold ends is coupled to (e.g., integral to) a proximal strut 284, rather than every peak. The length of the struts in this embodiment is greater than in FIGS. 18 and 19, which enables the membrane proximal end 286 (termination location) to be axially spaced by a short distance from the ends of the terminating peaks 285, as shown in the FIGS. This added strut length thus allows the membrane (or conduit) to be introduced into the sheath prior to the terminating peaks, which can reduce the likelihood of the proximal peaks from catching on the sheath during the sheathing process. This design, like other full length scaffolds, makes it easier to apply a membrane to the scaffold along its length. Peaks and valleys in adjacent sections are each coupled with a short linear connector. This design, like that in FIGS. 19A and B, is relatively rigid over its length and does not have particularly strong bending or flexing characteristics, which may be required for some applications. Additional potential drawbacks to this design include inadequate compressive resistance during unsheathing, difficult sheathing due to the geometry/pattern of the scaffold; and the expandable hub sections at the proximal and distal ends could become sensitive to fatigue and plastic deformation.

Figure 21A:
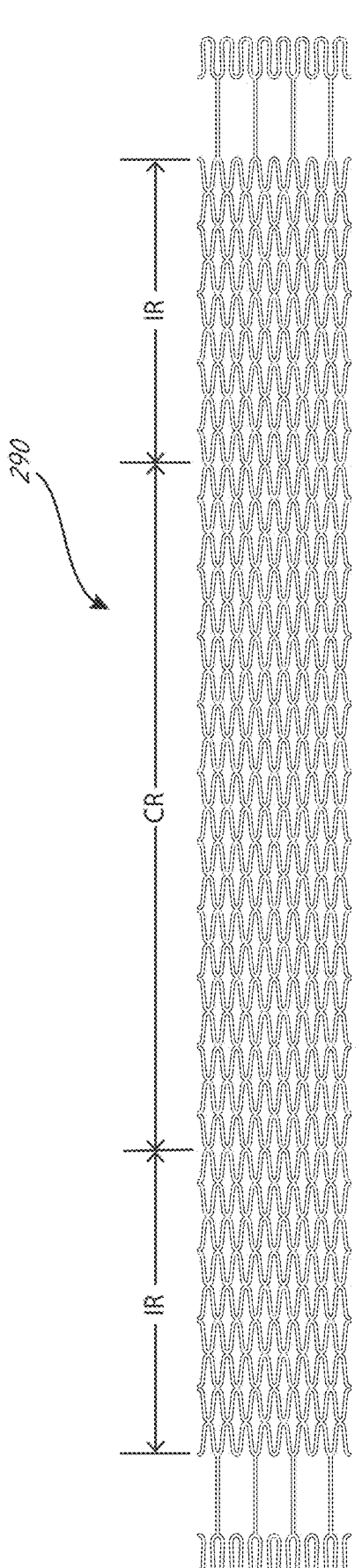
FIGS. 21A-C illustrate an exemplary scaffold design.
Figure 21B:
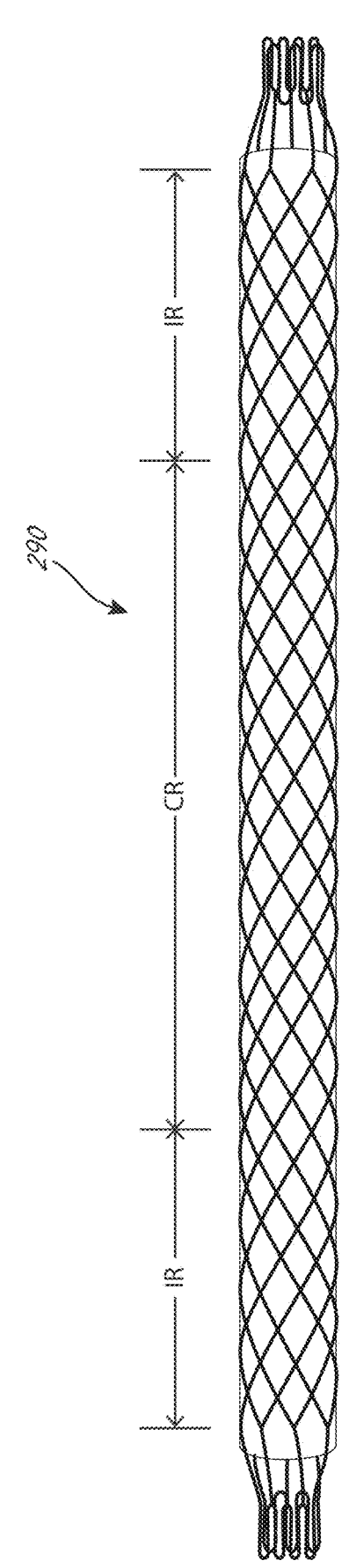
Figures 21C, 22A, 22B:
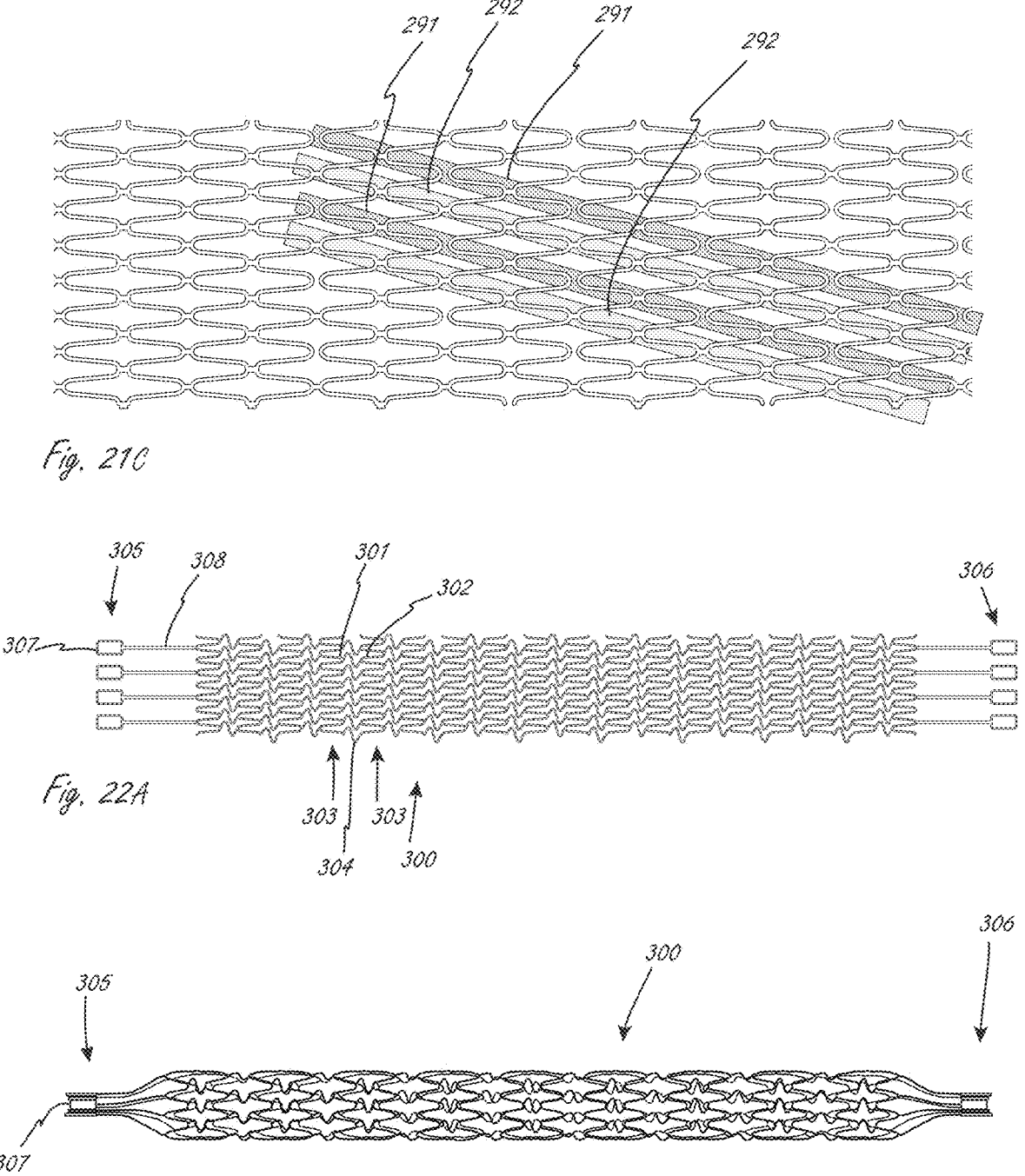
FIGS. 22A-B illustrate an exemplary scaffold design.

FIGS. 21A-C show a scaffold design that is similar to FIG. 20A, but with differences described below. In a central region "CR", between which proximal and distal impellers would be located, the design attempts to improve on the flexibility compared to FIGS. 20A and B. The benefits of this increased flexibility in this region are described herein. In the central region, alternating cell connections are removed, as shown, to improve flexibility in this region. In each axial section, alternating (radially) peaks are coupled, and alternating valleys are coupled. These removed alternating cell connections create helical regions 291 (see FIG. 21C) around the scaffold which do not include connection elements and helical regions 292 around the scaffold which include connection elements (see the magnified view in FIG. 21C). The helical regions alternative between no-connections regions 291 and connection regions 292.

Central region "CR" flexibility is increased in this design compared to the design in FIGS. 20-B because of the no-connection regions 291, and the scaffold has relatively more rigid impeller sections "IR" adjacent the central region where the impellers are disposed (not shown). The relatively increased rigidity in the impeller regions IR can help maintain tip gap and impeller concentricity. This scaffold pattern thus provides for a flexibility distribution, along its length, of a proximal section of relatively less flexibility ("IR"), a central region "CR" of relatively higher flexibility, and a distal section "IR" of relatively less flexibility. The relatively less flexibility sections (i.e., the two IR regions) are where proximal and distal impellers can be disposed (not shown but other embodiments are fully incorporated herein in this regard), with a relatively more flexible region in between. The benefits of the relative flexibility in these respective section are described elsewhere herein.

In this design, the lack of alternating connectors in the central region CR may, however, make the shape set and membrane application process more difficult however. The uncoupled (i.e., not connected) regions of the scaffold in the central region may also rub against and cut into the membrane, increasing the likelihood of membrane failure at those locations. Additionally, flexibility of the scaffold along its length may still not be adequate once membrane was applied, depending on the applications, the target placement location within the patient, access route. Additional possible drawbacks based on similar features are set forth above with reference to FIG. 20 (e.g., sheathing difficult due to geometry of scaffold).

FIGS. 22A and 22B illustrate a scaffold design 300 that is similar to FIGS. 21A and B, but with differences described below. Any feature from scaffolds herein can be incorporated into this scaffold design. The design includes peaks 301 and valleys 302 (only one set labeled for clarity) on axially adjacent sections 303 that are connected with spring connectors 304 (only one labeled for clarity) that couple radially-aligned peaks 301 and valleys 302 on adjacent sections. The spring-like connectors 304 in this design provide better flexibility along the length of the scaffold compared to FIGS. 21A-B. This is partially because the spring connectors 304 provide individual cell articulation.

The proximal and distal hub ends 305 and 306, respectively, have four independent, free-ended (i.e., not coupled to each other) members 307 (only one labeled at the proximal end for clarity) that are coupled to respective hubs (not shown). The struts 308 (only one labeled) thus have more flexibility relative to one another. More or fewer members 307 may be present at end each (e.g., two members at each end), and the ends may have different numbers of members (e.g., four at the proximal end, eight at the distal end). The individual (i.e., disconnected) members 307 at the hub ends improved manufacturing process of heat treatment, membrane coating and impeller loading. Some potential drawbacks for this design, depending on the particular application, may be that during unsheathing, strut buckling may occur due to inadequate compressive resistance. Additionally, the sheathing force may be undesirably high, which may be due at least partially to the membrane. Additionally, flexibility may be deemed inadequate once the membrane is applied to the scaffold.

For a particular exemplary application in which the pump portion is navigated for placement across an aortic valve (aspects of which are described herein), the scaffold design in FIG. 17A-F can provide the benefits set forth herein, whereas the scaffolds in FIGS. 18-22 may be suboptimal in one or more regards for this particular application (e.g., not sufficiently flexible, membrane application to scaffold suboptimal process, etc.). For some applications, however, one or more features of the scaffolds in FIGS. 18-22 may be desired. For example, the blood pump may be placed in a location where flexibility is not as important, or where relatively high stiffness across the length of the scaffold is desired or tolerated. Any of the features in the scaffold designs in FIGS. 18-22 can thus be combined in any suitable combination to provide a scaffold structure that provide desired functionality. For example, the design in FIGS. 17A-F could instead have hub regions that are not distinct members (like in FIGS. 22A-B), but are instead continuous like the designs in FIGS. 19-21.

FIG. 23 illustrates a proximal region of an exemplary pump portion, features of which can be incorporated into any of the pump portions herein. Not all of the features in the embodiment in FIG. 23 need to be included in the pump portion shown. The proximal end 310 of the fluid lumen has a flared radially outward configuration as shown with a smooth curve (the end of the lumen is furthest radially outward), which can facilitate radial flow of the impeller at the outflow (which is optionally a proximal impeller, and optionally one of a plurality of impellers). The distal end of the fluid lumen may also have the same or similar type of flared configuration (not shown), with or without a flared proximal end. A flared distal end configuration may limit the amount of contact between more rigid parts of the pump portion and a left ventricle wall (if that is where it is placed), reduce the likelihood of tissue being pulled into contact with the rotating impellers, it can prevent or minimize blockage of the pump portion inflow, and it may help prevent migration of the pump portion by acting as an enlarged interface region that can interface with native tissue and prevent further migration (e.g., engaging native valve tissue like leaflet and preventing the pump portion from passing through the valve opening). Any other suitable aspect of this disclosure is incorporated by reference into this embodiment.

Some aspects of the disclosure herein describe a pump portion that includes one or more central members (which may be referred to as "intermediate members" herein), optionally stationary and optionally between two first and second impellers (e.g., see FIGS. 10-13C). FIG. 24 is a perspective view and illustrates a portion of an exemplary conduit (optionally collapsible) that has a central member incorporated therein. Incorporated herein in this context includes a central member that is integrally formed with the conduit, as well as a central member that is attached to a collapsible conduit such that it is considered part of the collapsible blood conduit. For example, the central member could have an outer surface 313 that is attached (e.g., bonded) to an inner surface of any of the collapsible conduits herein (e.g., attached to a flexible membrane portion of the conduit), such that it is considered part of the collapsible conduit. The central member shown in FIG. 24 can have one or more flow modifying elements (e.g., blades) 314 extending radially inward from a peripheral portion 315 towards a central region 316 (not extending from a central region), but which are not coupled together at a central hub. The flow modifying elements 314 (e.g., blades) in FIG. 24 (or any other embodiment or claim herein), being part of an object that is not in rotational operation with an impeller, may be referred to herein as part of a stator, or diffuser vanes. The flow modifying elements can each have a variety of cross sectional geometries. The flow modifying elements can be configured to increase fluid pressure between impellers (with a drop in velocity) and/or reduce swirl velocity at its location, optionally between distal and proximal impellers.

In some embodiments the central member can have a plurality of blade like extensions that are chords of the peripheral curved portion (which may have a circular cross section), such that the chords don't have free ends as to do the flow modifying elements 314 in FIG. 24. One or more chords can extend from and to different regions of the peripheral curved portion. If there are a plurality of chords, and in an end sectional view, the chords can have different lengths between the two end points where they couple to (integrally or attached to) the outer peripheral region.

FIG. 25 is a perspective view of a proximal portion of a pump portion including an expandable scaffold and at least one impeller (not labeled but are easily identifiable based on other FIGS. herein). The pump portion also includes intermediate member 316, which in some ways is similar to other intermediate, or central, members herein. Intermediate member 316 includes flow modifying elements 317 (e.g., blades), each of which has an outermost engagement feature 318 (e.g., a flange) that is configured to stably interface with a corresponding mating feature (e.g., a peak or a valley) in the scaffold. The blade/scaffold engagement can cause collapse of the blades during radial compression and sheathing of the scaffold. Additionally, the blades and scaffold can interface or be coupled using a variety of techniques. For example, the flow modifying elements and scaffold can be coupled by spot welding. In some embodiments a flow modifying element 317 end can have a feature that interlocks with a feature on a central hub 319 (e.g., a dovetail interlocking relationship), with the locating features on central span bearing(s), not a drive cable. This may make manufacturing easier. The outer housing in this embodiment can be any of the outer housings herein.

One or more impellers that are part of a blood pump system (such as any herein) may be rotated at relatively high speeds, such as between 10,000 and 50,000 RPM. Impellers can be rotated by being in rotational communication with a drive member (e.g., a drive cable) or other component in rotational communication with the impeller, which can be rotated by an energy source (e.g., motor). Rotating the drive member at the same RPMs as the impellers may cause wear on the drive member, vibration, and perhaps requires lubricating (aspects of exemplary lubricating systems are described elsewhere herein) the drive member. It may be advantageous to have the drive member rotating at speeds less than the impellers, while still causing the impellers to rotate at the desired higher RPMs. One aspect of this disclosure is a blood pump that includes one or more drive members that can be rotated at lower RPMs than one or more impellers. This may decrease drive member wear, reduce lubrication needs, and reduce vibration. This may be particularly advantageous in applications in which the blood pumps are used for relatively long terms (e.g., 24 hours or more). For example, this may be particularly advantageous for cardiogenic shock indications.

The rotating drive member (e.g., drive cable, magnetic stator) can rotate slower than the one or more impellers. In some exemplary embodiments the rotating drive member may be rotating between zero and one times (1×) the impeller RPM. For example, if any impeller is rotating at 20,000 RPM, the drive member may be rotating between zero and 20,000 RPM. In some embodiments the drive member may be rotating between 0.25 and 1× the impeller RPM, or between 0.3 and 1×, or between 0.4 and 1×, or between 0.5 and 1×, or between 0.6 and 1×, or between 0.7 and 1×, or between 0.8 and 1×, or between 0.9 and 1×.

Figures 26A, 26B:
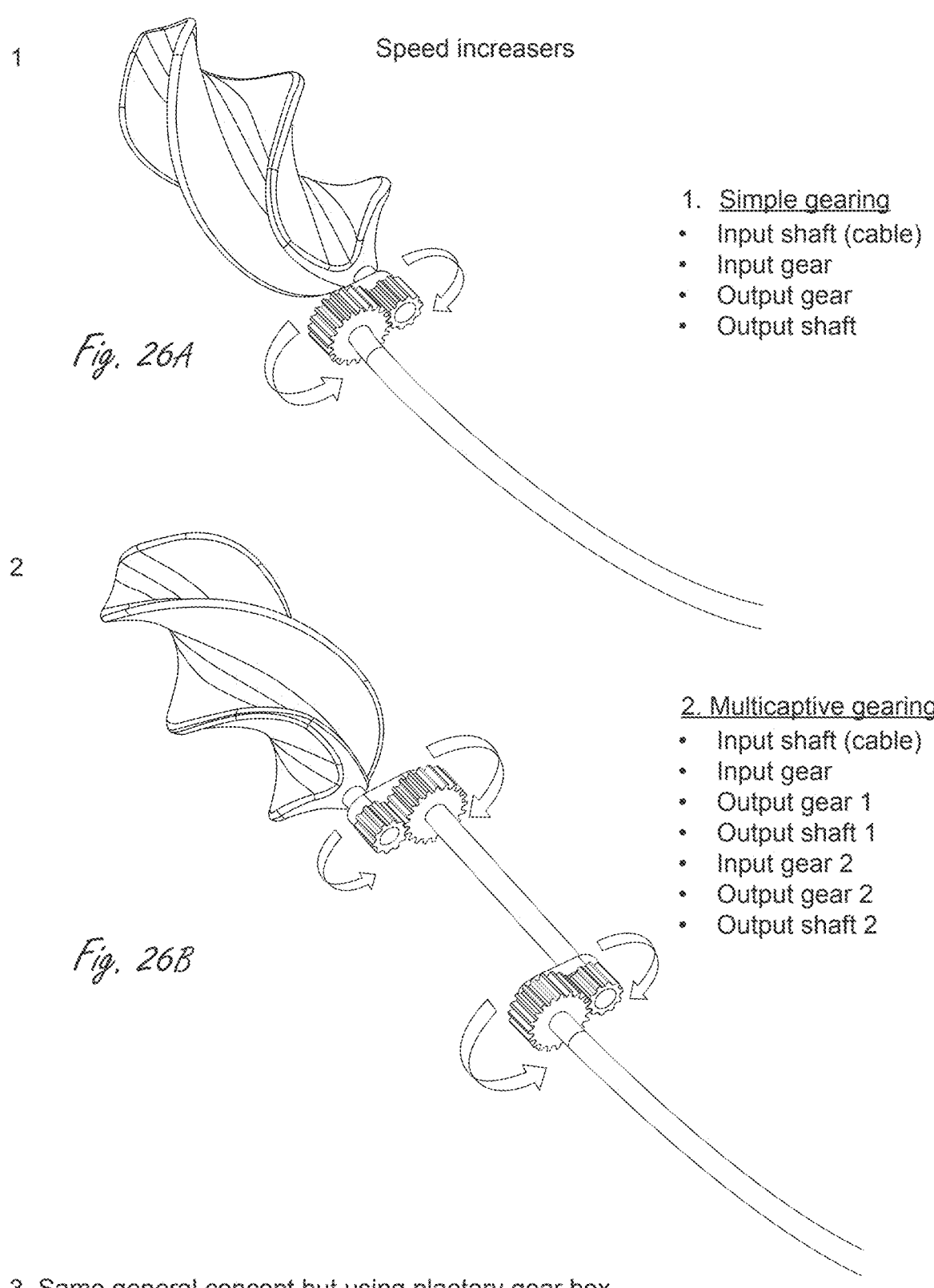
FIGS. 26A and 26B illustrate portions of exemplary blood pumps with exemplary speed increaser assemblies and mechanisms that may be incorporated into a blood pump.

FIG. 26A illustrates only portions of an exemplary blood pump to illustrate an exemplary embodiment of how to rotate an impeller faster than a drive member. The exemplary speed increase mechanism in FIG. 26A utilizes gearing to accomplish the speed increase, with an output gear with a smaller diameter than the input gear, causing more speed at the output gear axis, about which the output shaft rotates. The output shaft (and the impeller to which it is coupled)

thus rotates faster than the input shaft (e.g., drive member). FIG. 26B illustrates how to use multiplicative gearing to get a greater difference (compared to FIG. 26A) in speeds between the input shaft (e.g., drive member) and output shaft 2 (to which the impeller is coupled). Input gear 2 has a greater diameter than output gear 2.

Additionally gearing systems such as planetary gear boxes and magnetic gear boxes can also be used to increase the speed the one or more impellers relative to the rotation of the input drive member.

Figure 27:
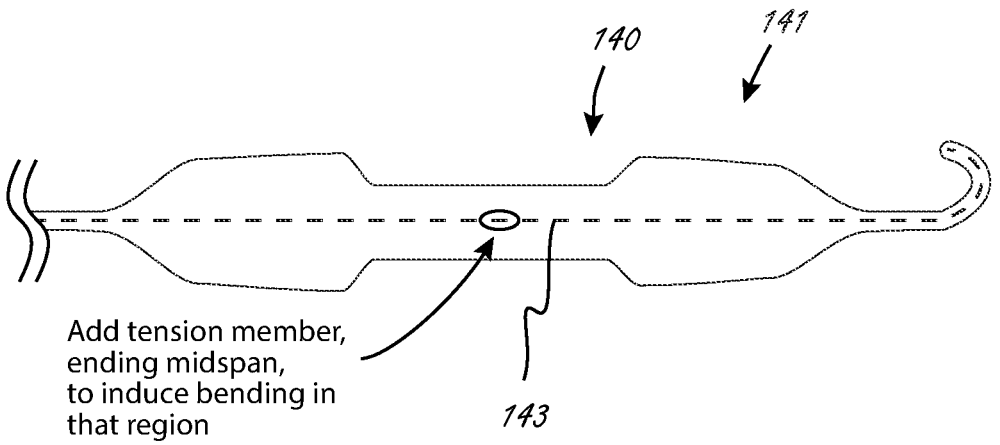
FIG. 27 illustrates an exemplary pump portion that is adapted, optionally with at least one tensioning member, so that the pump portion can be deflected at at least one location along the length of the pump portion.

FIG. 27 illustrates an exemplary design of a pump portion 140 that includes at least one tensioning member 143 (e.g., pullwire) that, when tensioned, induces bending in at least a portion of the pump portion. A tensioning member may extend as far distally as in between distal and proximal impellers (or further distally or further proximally), and can cause a bend to form between the two impellers after the pump portion is deployed from a delivery system. For example, a handle can include an actuator (lever, button, etc.) that when actuated tensions the one or more tensioning members, causing deflection in region. All known tensioning member (e.g., pullwire) designs and uses can be incorporated into this embodiment to implement the one or deflectable regions. For example the catheter can include one or more pullwire lumens extending along any portion thereof, wherein the pullwire(s) is adhered at its distal end to one or more parts of the catheter depending on the location(s) of the desired deflection region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different.

Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 28A:
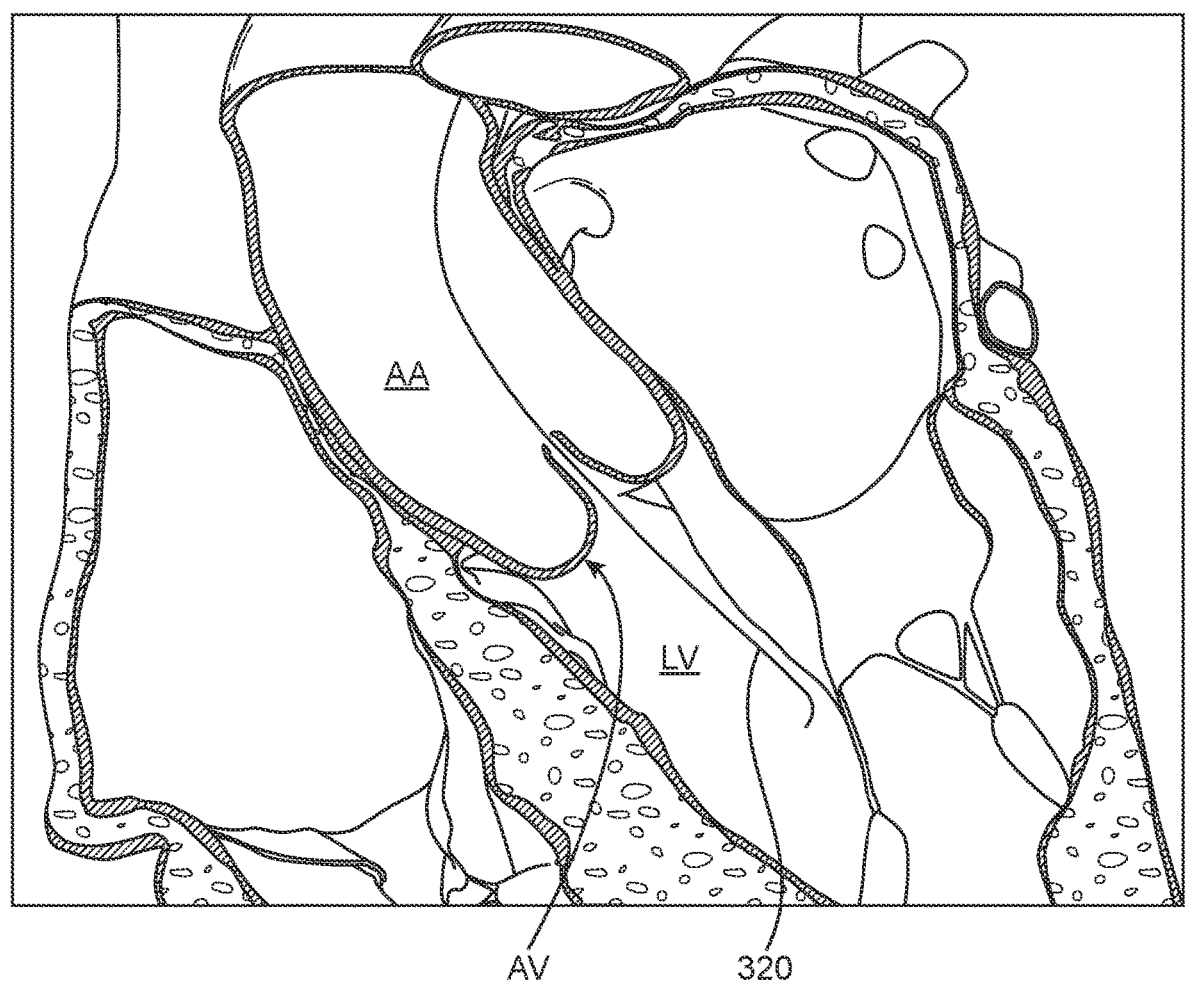
FIGS. 28A-28F illustrate an exemplary sequence of steps that may be carried out based on an exemplary method of using an exemplary blood pump.
Figure 28B:
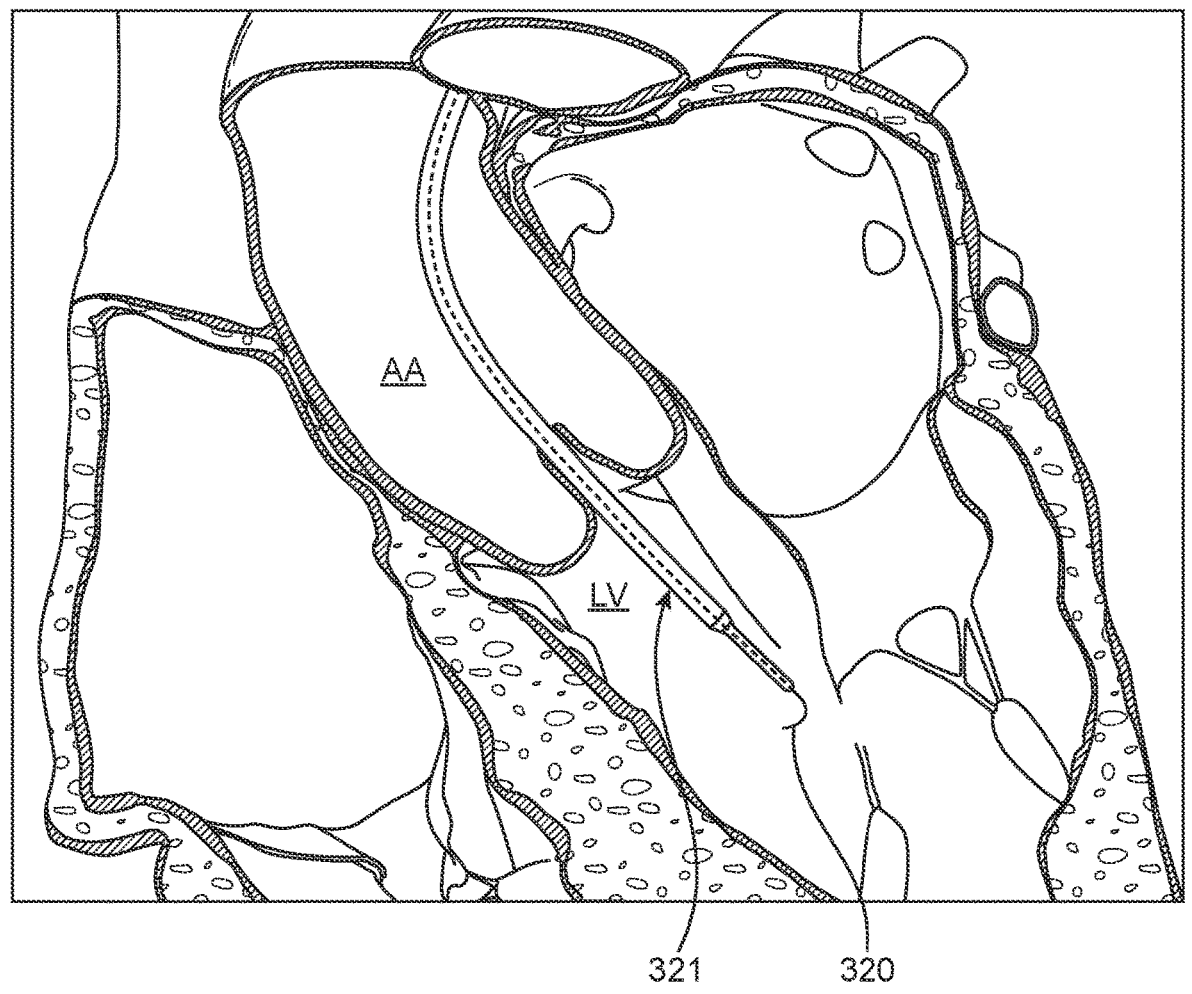

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 28A), and the blood pump 321 (including a catheter, catheter sheath, and pump portion within the sheath; see FIG. 28B) can be advanced over the second wire towards a target location, such as spanning an aortic valve "AV," and into a target location (e.g., left ventricle "LV"), using, for example, one or more radiopaque markers to position the blood pump.

Figure 28C:
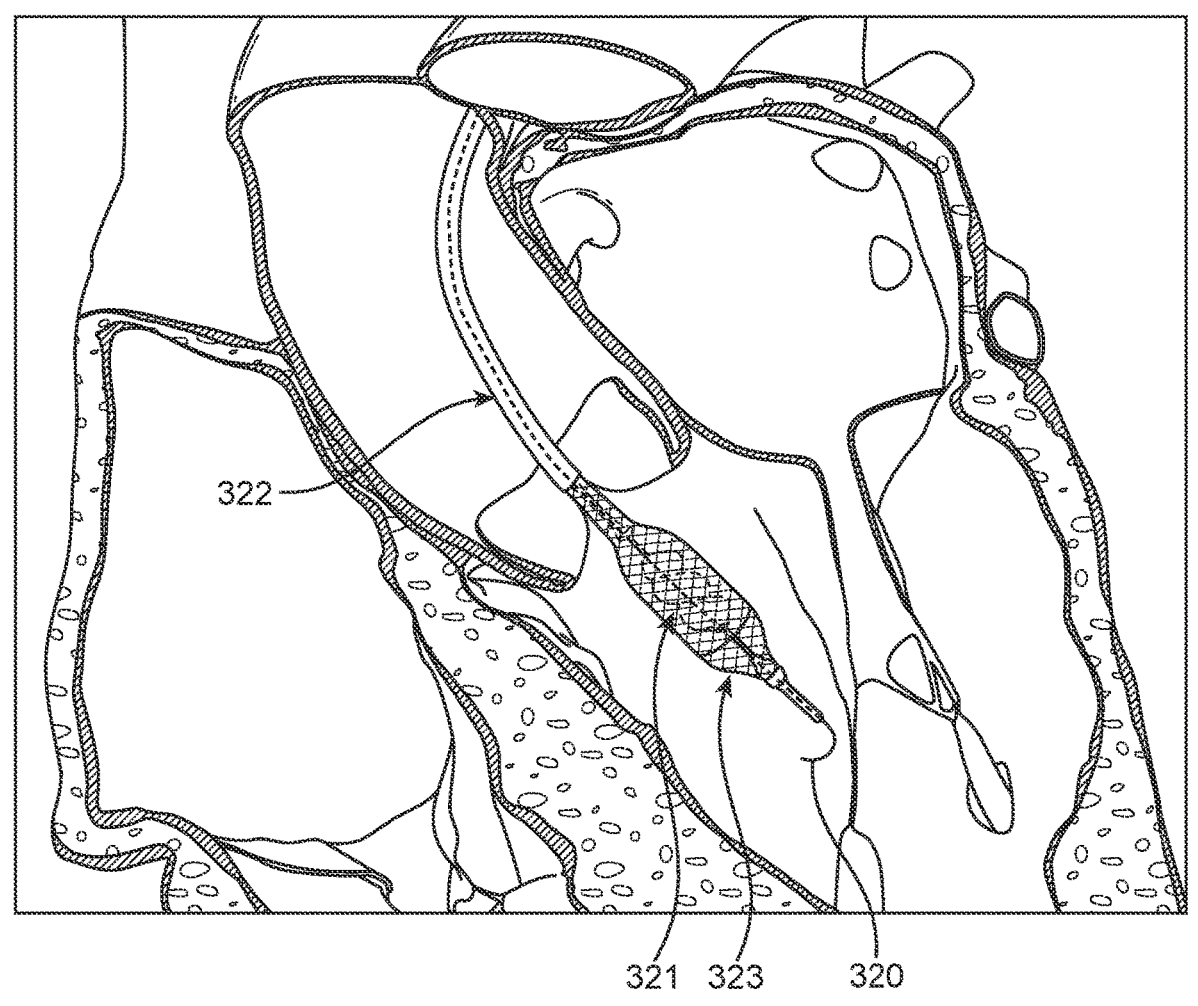
Figure 28D:
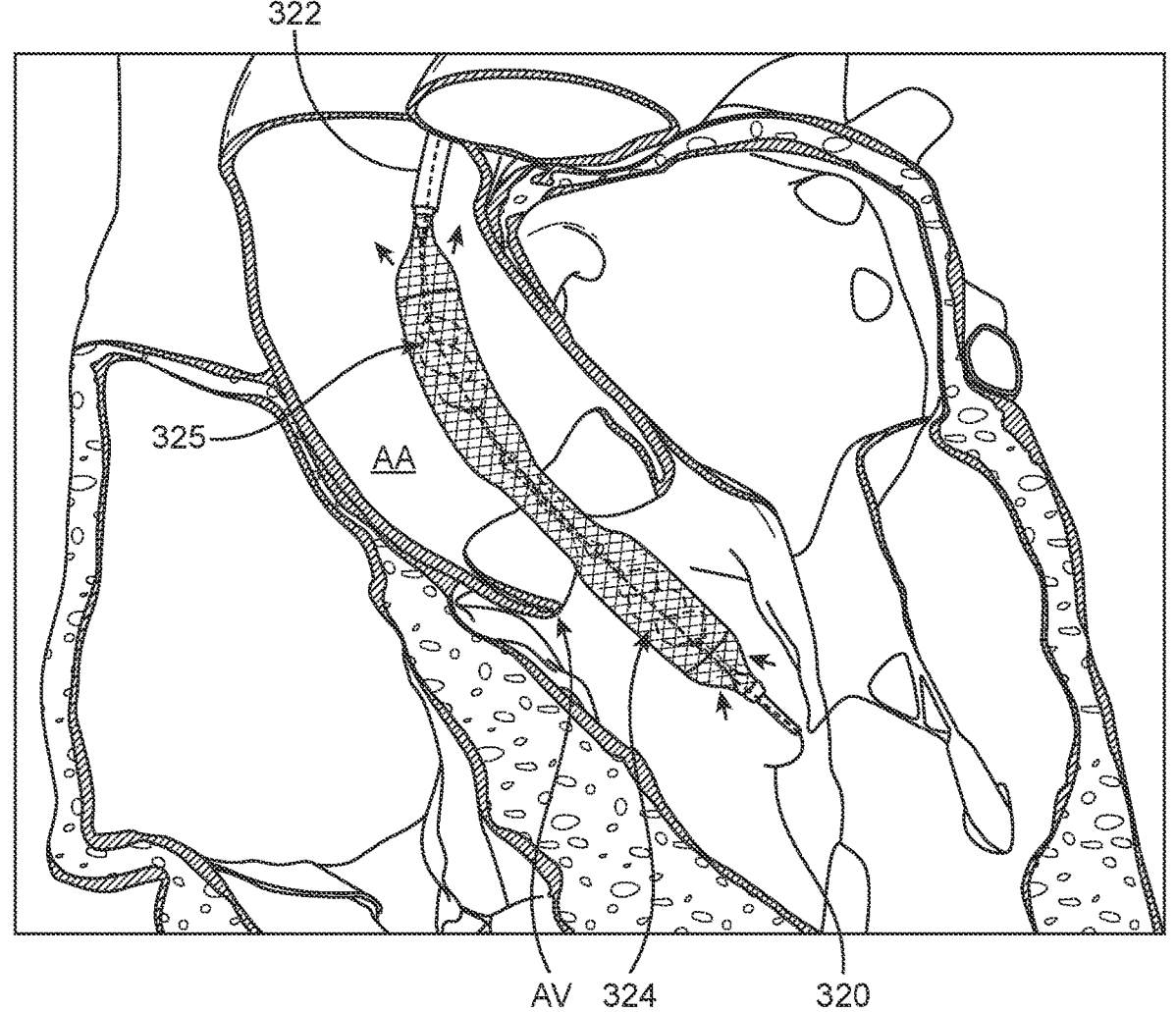

Once proper placement is confirmed, the catheter sheath 322 (see FIG. 28C) can be retracted, exposing first a distal region of the pump portion. In FIG. 28C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 28D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 28E:
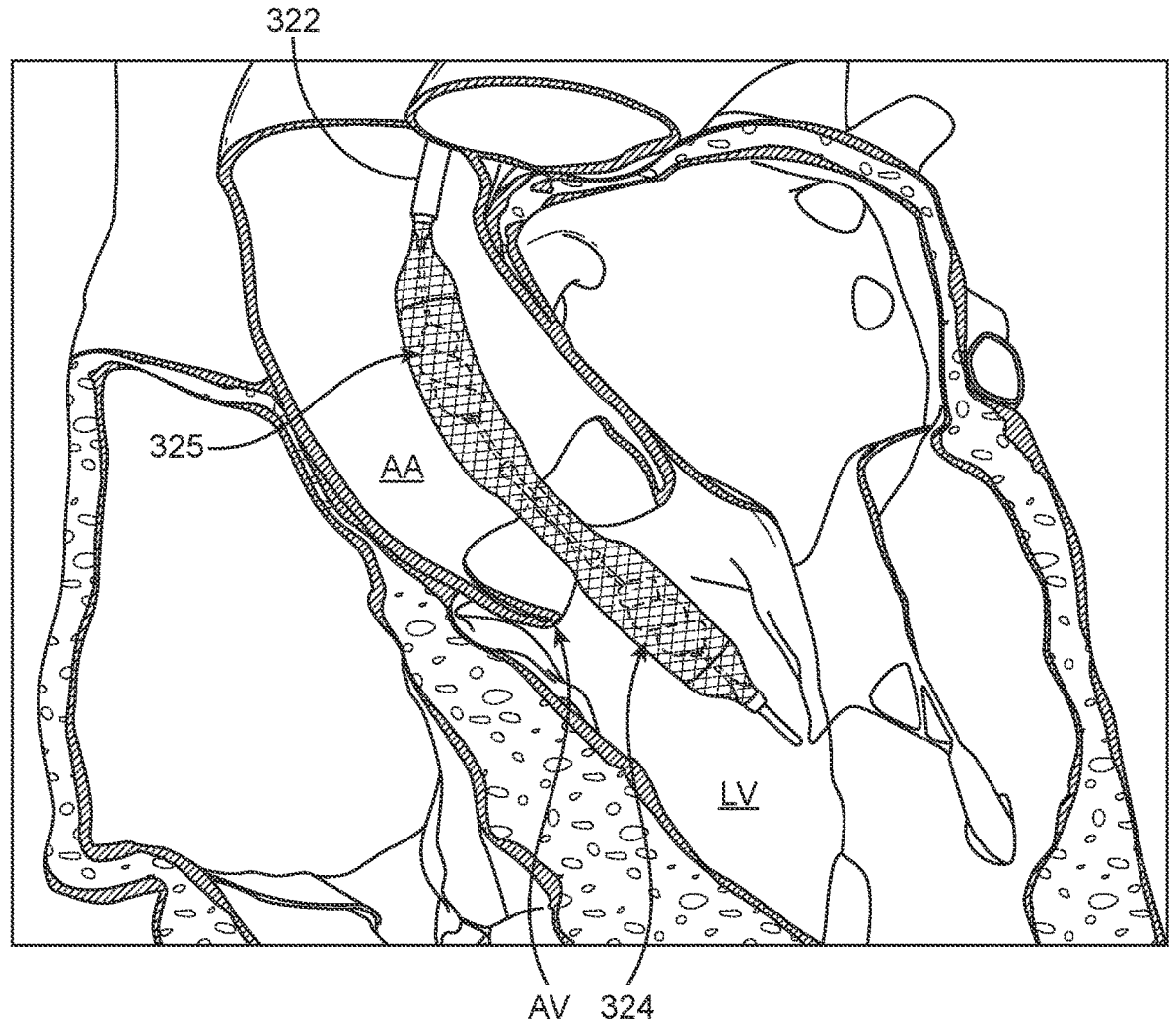
Figure 28F:
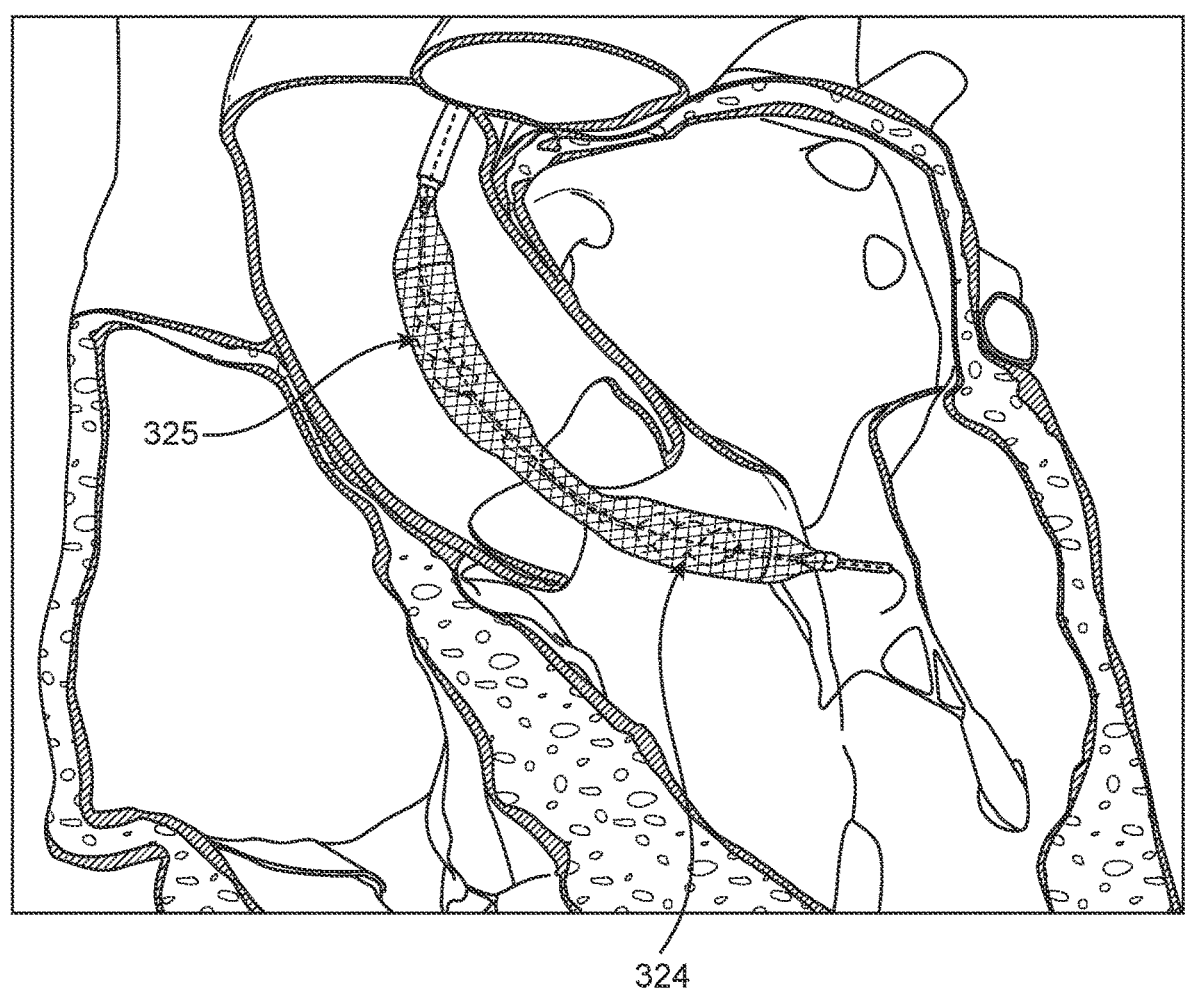

The second wire (e.g., an 0.018" guidewire) may then be moved prior to operation of the pump assembly (see FIG. 28E). If desired or needed, the pump portion can be deflected (active or passively) at one or more locations as described herein, as illustrated in FIG. 28F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. An exemplary pump portion with an exemplary tensioning member is shown in FIG. 27. It is understood that in FIG. 28F, the pump portion is not in any way interfering or interacting with the mitral valve, even if it may appear that way from the figure.

Any number of purge lines may then be attached to the proximal portion of the blood pump that is disposed outside of the patient. For example, fluid inlet(s) lines and fluid outlet(s) lines may be attached to one or more fluid ports on the proximal portion of the blood pump. A purge process can then be initiated to move fluid into the blood pump through at least one fluid pathway. One or more Confirmation steps can be performed to confirm the purge is operating as intended before turning on the pump. The pump assembly can then be operated, causing rotation of the one or more impellers. Any one of flow rate(s), pressure(s), and motor operation can be monitored at any time.

FIGS. 29-35B illustrate additional exemplary intermediate members, which may function at least partially as stators (and may also provide radial support), and that include a plurality of fluid modifiers that may be disposed between distal and proximal impellers, and are adapted to influence blood flow between the impellers, other examples of which are provided herein. Any aspect of FIGS. 29-35B may be incorporated with any other aspect of the blood pumps herein. For example, impellers might not be shown in FIGS. 29-35B for clarity but it is understood that one or more impellers can be incorporated into these embodiments.

Figure 29A:
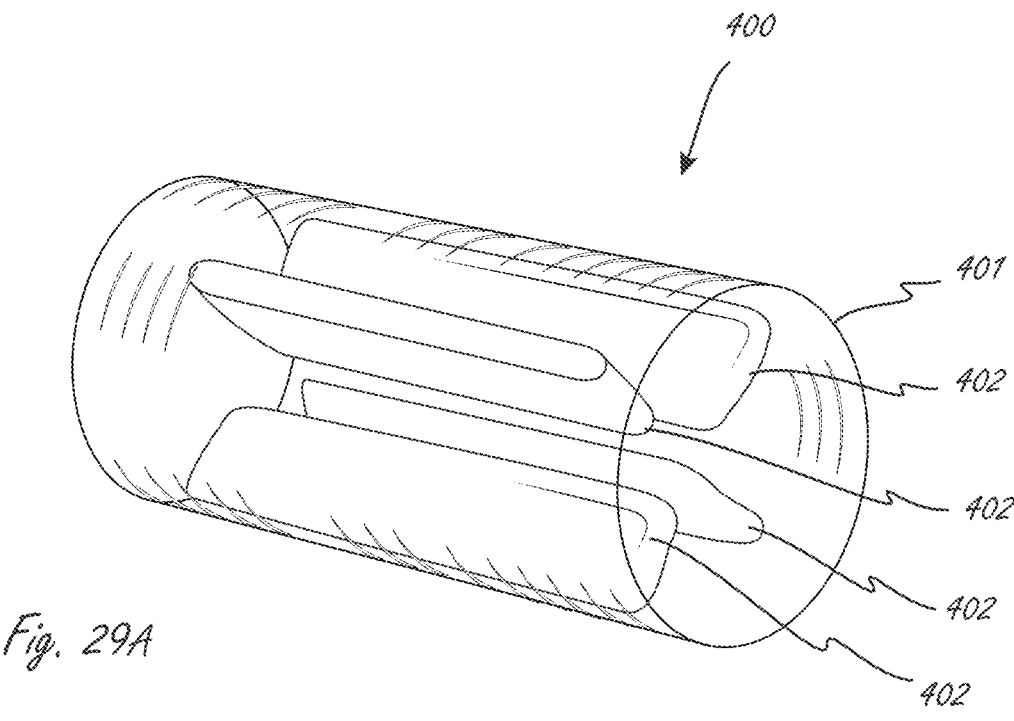
FIGS. 29A and 29B illustrate exemplary collapsible flow modifying elements that may be part of a pump portion, optionally disposed between two collapsible impellers.
Figure 29B:
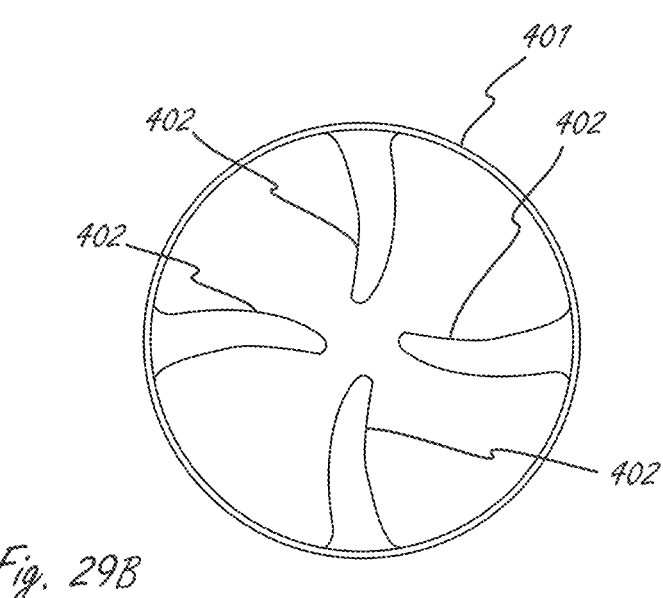
Figure 30A:
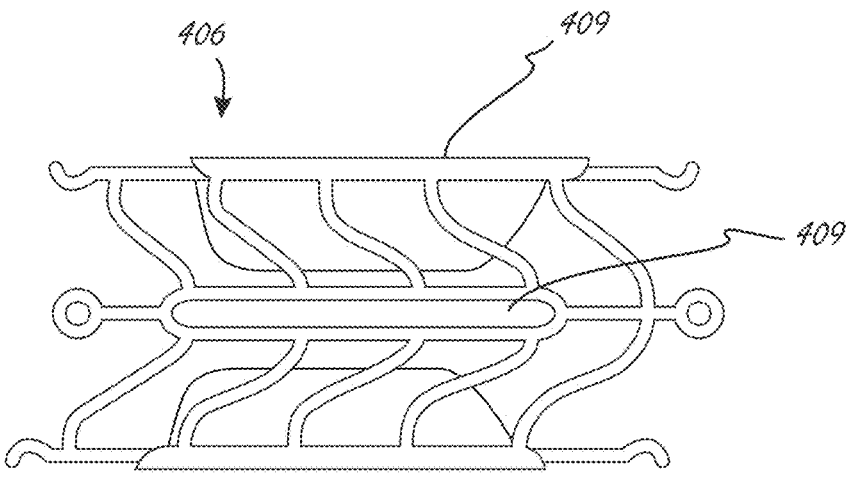
FIG. 30A illustrates an exemplary blood flow conduit support member that includes a plurality of apertures therein, the apertures sized and configured to receive, and interface with, one or more flow modifying elements.
Figure 30B:
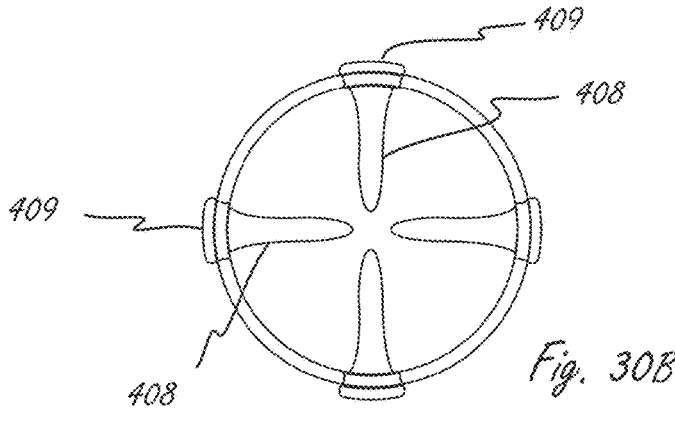
FIG. 30B illustrates an end view of an exemplary support member, wherein a plurality of flow modifying elements are each disposed in one of a plurality of support member apertures.
Figure 31A:
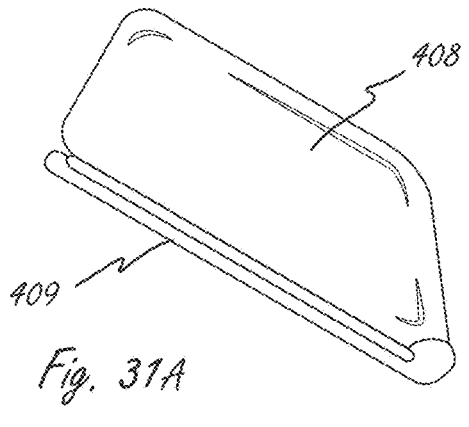
FIGS. 31A and 31B illustrate exemplary flow modifying elements, which may be sized and configured to be advanced through a conduit support member aperture, such as those in FIGS. 30A and 30B.
Figure 31B:
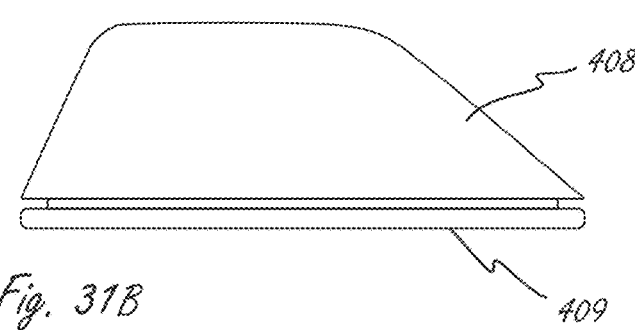

FIGS. 29A and 29B illustrate an exemplary blood conduit 402 with flow modifiers 402 extending radially inward from an inner surface of the conduit. The flow modifiers (e.g., blades) do not extend to a central hub, but rather they have free radially inner ends, which can be seen more clearly in the end view of FIG. 29B. The flow modifiers 402 (e.g., stator elements) may be molded individually, then secured to the inner surface of the conduit (e.g., to a membrane). Conduit 402 may also include any other supporting members herein, such as, without limitation, any of the nitinol scaffolds herein. Flow modifiers may have slight curvature to them, which can be seen in FIG. 29B. Flow modifiers 402 may be considered part of one stator.

FIGS. 30A, 30B, 31A and 31B illustrate an exemplary support member that has a plurality of apertures therein, each configured to receive therethrough and interface with a flow modifier 408, which have enlarged regions 409 that interface with a part of the support member to help stabilize the position of the flow modifier relative to the support member. The location of elongate apertures 407 establish the position and orientation of the flow modifiers (e.g., stator elements). After the flow modifiers are inserted into the apertures, a conduit material (e.g., membrane) may be sprayed over the subassembly to further secure the modifiers 408 in place. Alternatively, the material could be sprayed first, then a cut made through the apertures 407, into which the modifiers may be inserted. An additional layer of material could be sprayed to create a seal. Flow modifiers 408 may be considered part of one stator.

Figures 32A, 32B, 32C:
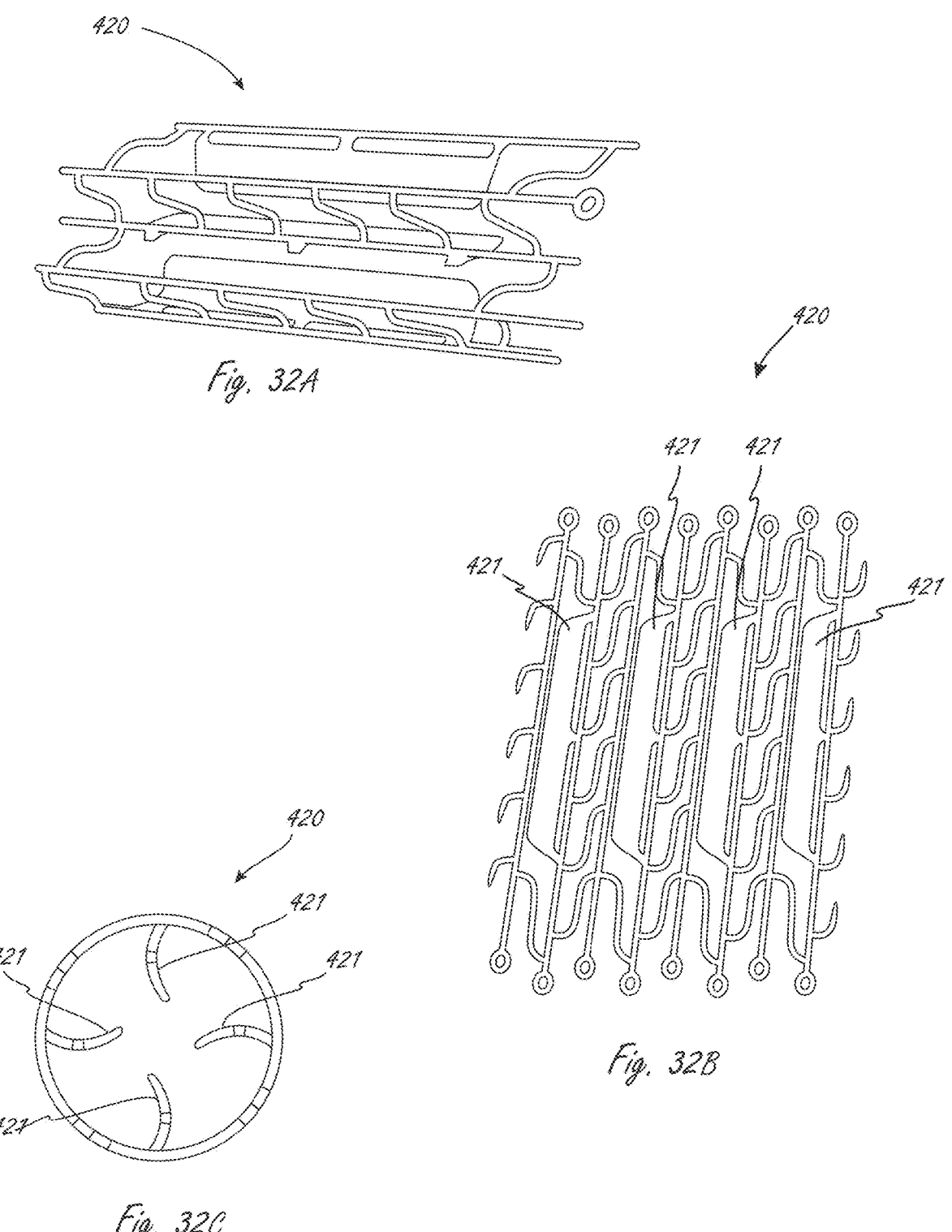
FIGS. 32A, 32B and 32C illustrate an exemplary conduit support member that includes a plurality of flow modifying elements that are integrally formed with the support member, and that can self-deploy to an active, flow modifying configuration in which are extend radially inward.

FIGS. 32A-32C illustrate an exemplary support member 420 (e.g., scaffold, e.g., nitinol) in which one or more flow modifiers 421 are integrated (integral) into the expandable scaffold structure, which can be directed radially inward in the shape set process, thus creating a flow modifier (e.g., stator. A material (e.g., polymer) can be applied to the member 420 to create a blood conduit. The scaffold and flow modifiers could also be designed to be fabricated separately and interlocked after a membrane material (e.g. polymer) is applied to the scaffold. The scaffold can have any pattern described herein. Flow modifiers 421 may be considered part of one stator.

Figure 33A:
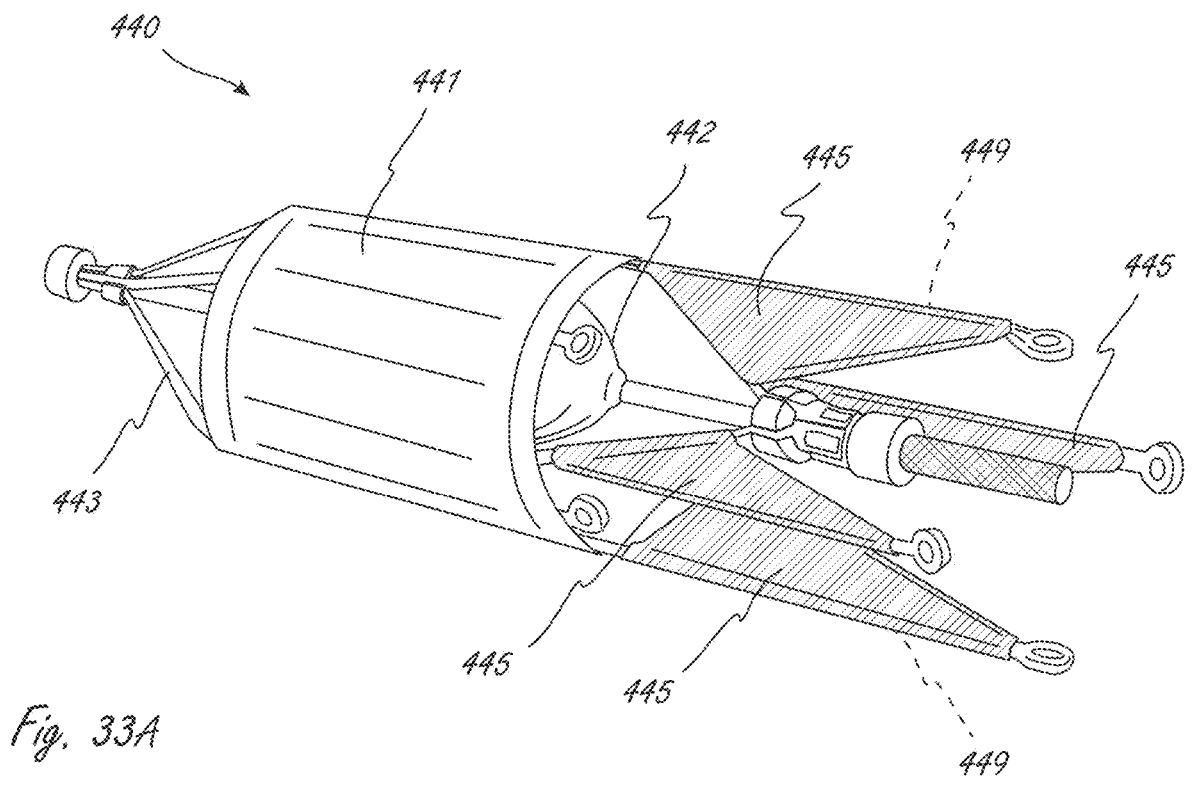
FIGS. 33A and 33B illustrate an exemplary pump portion that includes a plurality of flow modifying elements 445, optionally secured to struts of the pump portion.
Figure 33B:
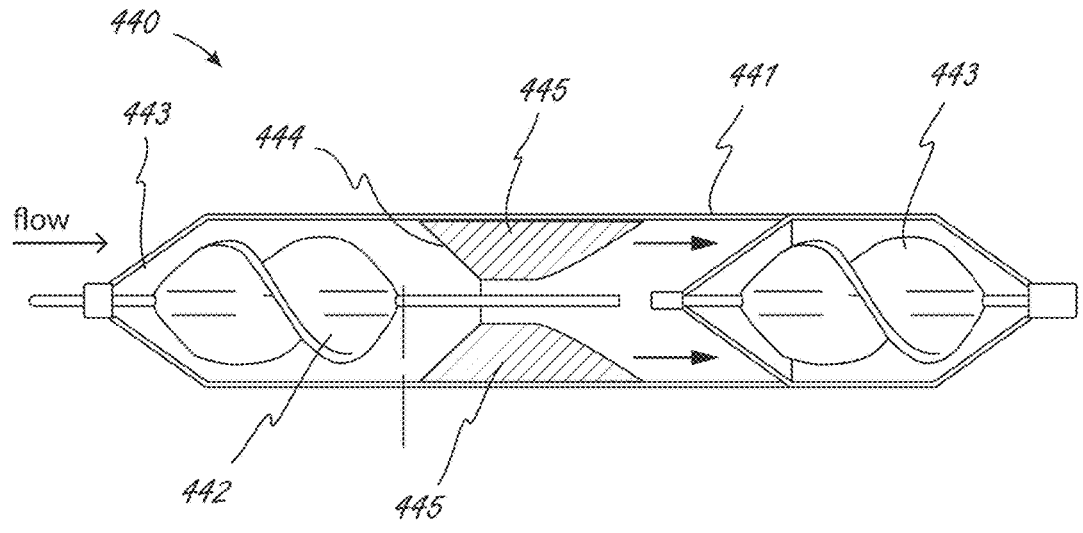

FIGS. 33A and 33B illustrate an exemplary collapsible pump portion 440 including conduit 441, distal impeller 442, and proximal impeller 443. The pump also includes a plurality of flow modifiers 445, which are secured to struts 444 in the pump. The struts can be part of a distal impeller basket, examples of which are described herein. In this embodiment the flow modifier are secured to proximal struts of a distal impeller basket, but could be secured to distal or proximal struts of a proximal impeller basket. Flow modifiers in this embodiment can be flexible membrane, or other relatively flexible and thin material. The flow modifiers are positioned to manage flow over the strut, as well as being fixed to a longitudinal spine element 449 (lines shown in phantom since the element may be covered by flow modifier material 445) extending from a scaffold to aid in directing flow longitudinally through the blood conduit. The flow modifiers (e.g., stators) could be flexible polymer with or without fabric reinforcement to aid in collapsibility and sheathing. Flow modifiers 445 may be considered part of one stator.

Figure 34:
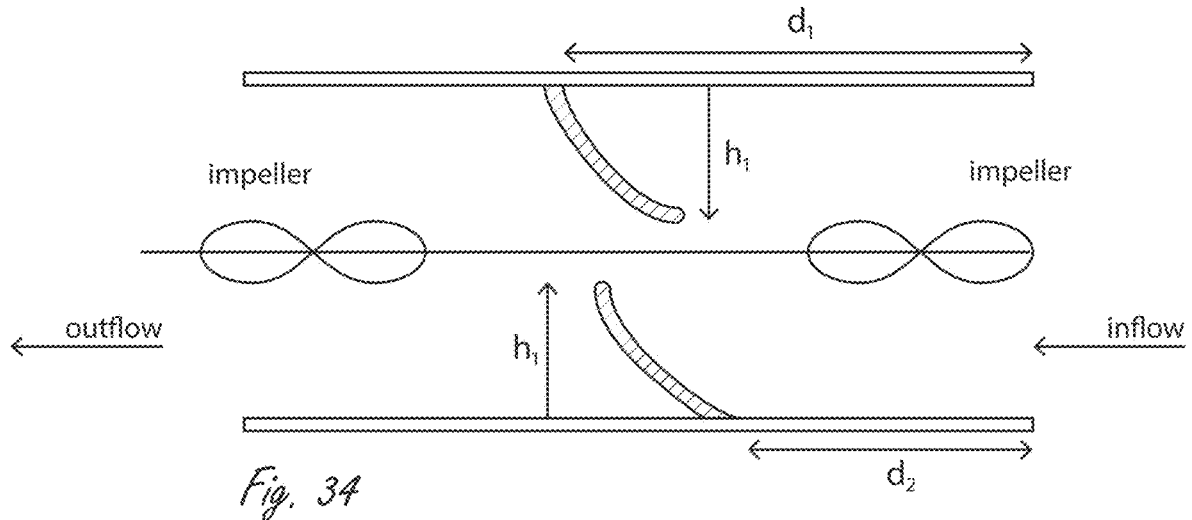
FIG. 34 illustrates a side view of exemplary flow modifying elements disposed between first and second impellers.
Figure 35A:
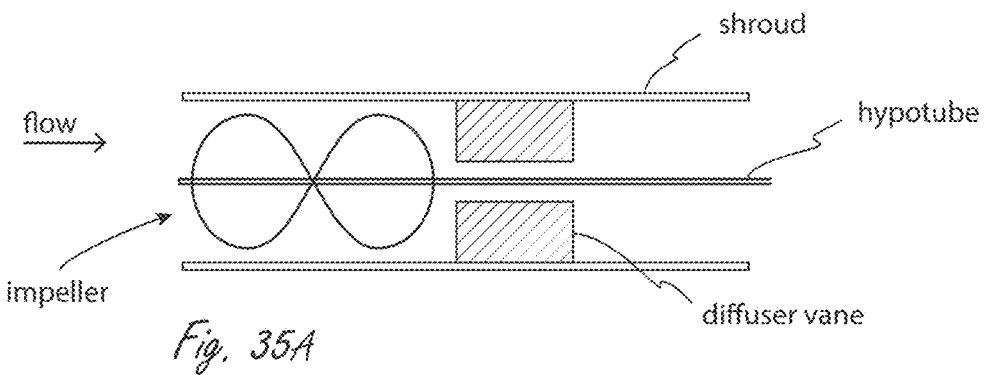
FIGS. 35A and 35B illustrate side and top views, respectively, of exemplary flow modifying elements (e.g., diffusers in these FIGS.).
Figure 35B:
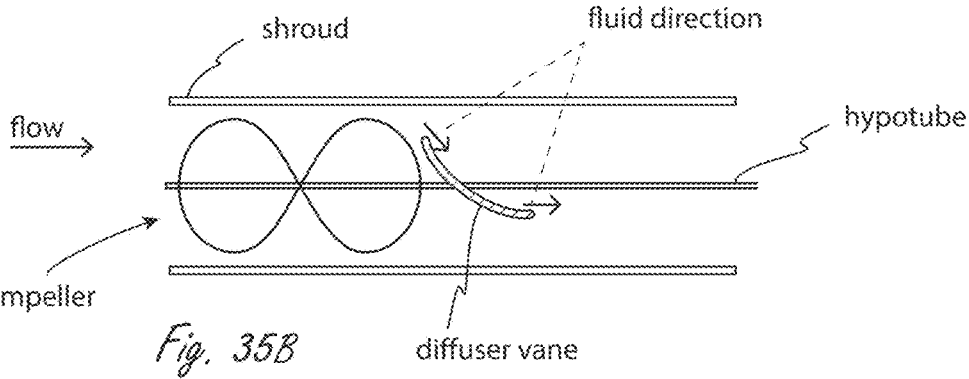

The disclosure that follows, including FIGS. 34, 35A and 35B, may be referred to as hugging collapsible diffusers to increase outflow pressure. FIG. 34 illustrates a concept with hugging vanes of diffuser/stator. FIGS. 35A and 35B illustrates the profile of hugging vanes (A) side view (B) top view. Diffusers are generally designed as stationary components to convert rotational speed/energy of flow into desired additional pressure by de-swirling the flow (i.e. removing the rotational velocity component of fluid). The shape of a diffuser (stator) plays an important role in efficiency of this process. Pump portions here in are generally collapsible for delivery (e.g., to an aortic valve), and then are expanded for use.

FIGS. 34-35B illustrate an exemplary concept is which vanes of the diffuser have a special geometry/configuration that hug/spoon each other to allow crimping of the pump to the desired delivery profile size. The concepts elsewhere herein related to flow modifiers can be incorporated into these embodiments as well (e.g., scaffolds interfacing with flow modifiers).

With respect to FIG. 34, the diffusers can be designed to be conformable, part of the shroud/blood conduit and adapted to increase pressure further. In some embodiments, an elastic material like nitinol can be used for an inner part of the diffusers, which can be coated with a material (e.g., polymer, which may be the same material as the blood conduit material) to create an diffuser outer surface.

Any of the stators herein, including any of the flow modifying elements (aka flow modifiers), can be incorporated with any suitable aspect of any shroud, housing, blood flow conduit, impeller basket, etc., that is described herein, including any methods of manufacturing the same.

In some embodiments the diffusers can be made of the same or similar material to the blood conduit membrane. Injection molding can be used to make the diffusers.

An exemplary clinical advantage e could be to maintain RPM of the drive cable/pump within reasonable limit to avoid hemolysis, while still increasing pressure to a desired range using a pump with the diffusers.

Figures 36A, 36B:
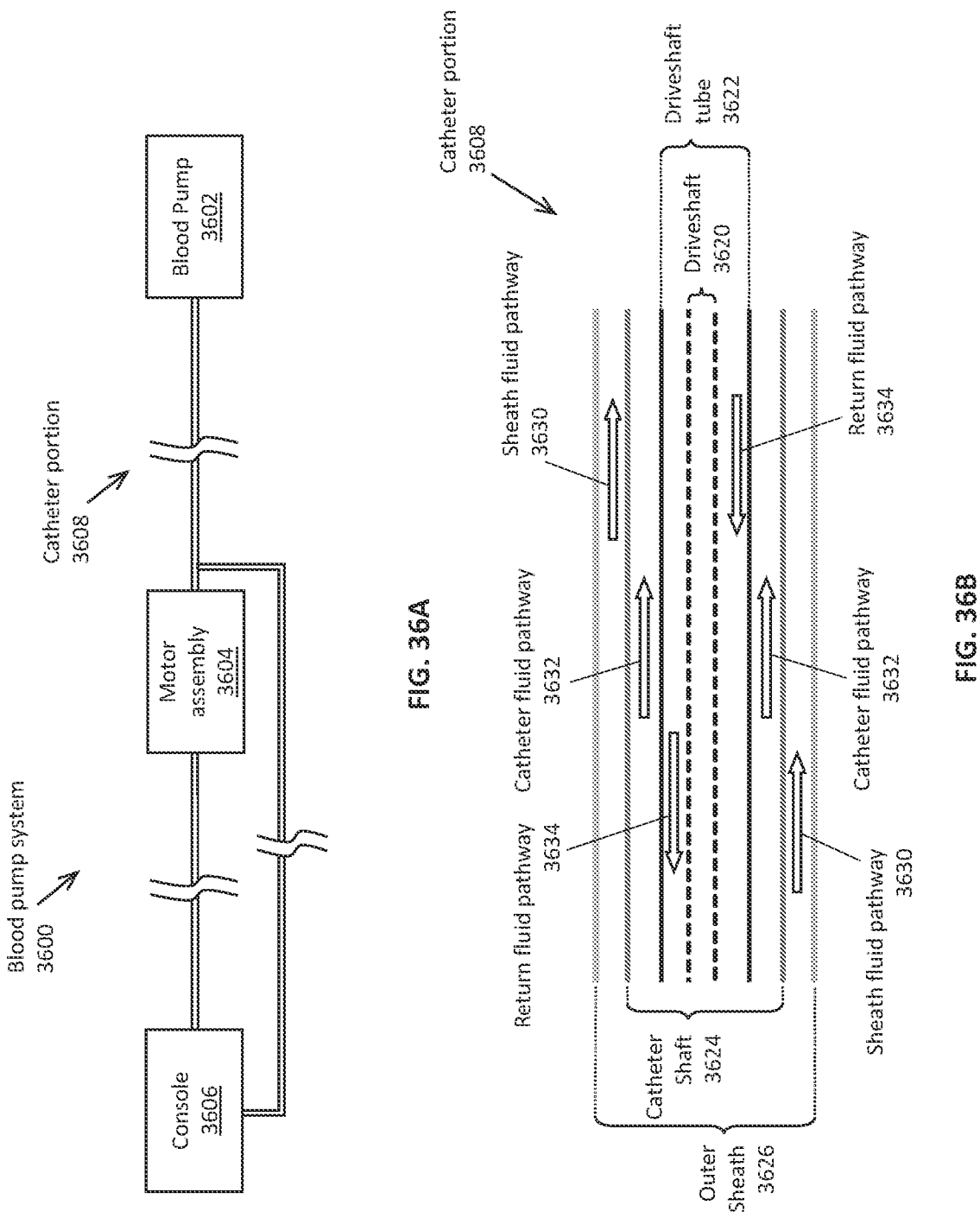
FIG. 36A illustrates at least a portion of an exemplary blood pump system including an intravascular blood pump.
FIG. 36B illustrates an exemplary fluid pathway through at least a portion of the exemplary blood pump system of FIG. 36A.

FIG. 36A schematically illustrates at least a portion of an exemplary blood pump system 3600. Any of the blood pump systems described herein can have the arrangement of system 3600. The exemplary blood pump system 3600 may include an external console 3606, a motor assembly 3604 and catheter portion 3608. A distal end of the catheter portion 3608 can include an intravascular blood pump 3602. The intravascular blood pump 3602 can be configured to enter a patient's vascular system to pump blood within the patient's body while the console 3606 and motor assembly 3604 remain outside of the patient's body. The console 3606 may include one or more controllers (e.g., as part of a computer) for controlling aspects of the motor assembly 3604 and blood pump 3602. The console 3606 may include a user interface (e.g., computer display) for interacting with a user. Console 3606 may be in fluid and/or electrical communication with the motor assembly 3604 via, for example, one or more electrical wires and/or one or more fluidic channels. In some examples, the console 3606 may be in fluid and/or electrical communication with the catheter portion 3608 via, for example, one or more electrical wires and/or one or more fluidic channels (e.g., bypassing the motor assembly 3604). The motor assembly 3604 may include one or more motors that are in rotational communication with one or more internal driveshafts (also referred to herein as drive cables) of the blood pump 3602. Any driveshaft and/or drive cable herein may be considered part of a rotational drive mechanism that communicates rotation from a motor to one or more impellers of the blood pump. In some cases, the motor assembly 3604 is part of a handle for controlling the blood pump 3602. In other cases, the motor assembly 3604 is a separate structural entity from a handle.

FIG. 36B schematically illustrates a close-up section view of at least a portion of an exemplary catheter portion 3608, and illustrates exemplary and optional fluid pathways therein. The catheter portion 3608 can include a series of coaxial tubular components including a hollow driveshaft 3620, a driveshaft tube 3622, a catheter shaft 3624 and an outer sheath 3626. The hollow driveshaft 3620 can be in rotational communication with one or more impellers of a pump portion of the blood pump 3602. The hollow driveshaft 3620 can be configured to rotate by being rotatably coupled to a motor of the motor assembly 3604. The hollow driveshaft 3620 may include an inner lumen to accommodate, for example, a guidewire. In some cases, at least a portion of the hollow driveshaft 3620 may include a porous material through which some fluid (e.g., saline, dextrose, return fluid, etc.) may penetrate through the walls of the driveshaft 3620 and into the inner lumen of the driveshaft 3620. In some examples, the driveshaft 3620 walls may include a mesh material. The driveshaft tube 3622 may be configured to house the rotatable driveshaft 3620. The catheter shaft 3624 (which may be referred to simply as a catheter, and which may include one or more layers of material) may house components of the blood pump 3602 at a distal portion of the catheter 3624, such as one or more bearing assemblies of the blood pump 3602. The outer sheath 3626 may house some or all of the pump portion of the blood pump 3602 within a distal portion of the sheath 3626, for example, during delivery of the blood pump 3602 to a target location within the patient. Once, in position, the sheath 3626 may be retracted to allow expansion of the expandable portions of the blood pump 3602. In some cases, the motor assembly 3604 may be adapted to rotate the driveshaft 3620 and not be adapted to rotate the driveshaft tube 3622, catheter shaft 3624 and/or sheath 366.

Depending on the particular design of the catheter portion, the catheter portion may include one or more fluid pathways that allows fluid to flow in the annular spaces between each of the components of the catheter portion 3608. For example, clean fluid (e.g., clean saline) may flow (e.g., by being pumped with a pump) toward the blood pump 3602 via a sheath fluid pathway 3630 between the sheath 3626 and the catheter shaft 3624. Fluid flow through the sheath fluid pathway 3630 may prevent blood from stagnating and forming clots in the annular space between the sheath 3626 and the catheter shaft 3624 at a distal end of the sheath 3626. Fluid from the sheath fluid pathway 3630 may enter the patient's body with no substantial return fluid pathway. Clean fluid (e.g., saline pumped from the saline bag in the console) may also flow (e.g., by being pumped) toward the blood pump 3602 via a catheter fluid pathway 3632 between the catheter shaft 3624 and the driveshaft tube 3622. Some or all of the fluid in the catheter fluid pathway 3632 may return from the blood pump 3602 via a return fluid pathway 3634 (which may be referred to in any embodiment herein as a waste fluid pathway). Flowing fluid through the catheter fluid pathway 3632 and return fluid pathway 3634 may cool and/or lubricate moving components (e.g., the rotating driveshaft 3620 and bearings) within the blood pump 3602. The catheter fluid pathway 3632 and return fluid pathway 3634 may flush and keep possible debris (e.g., from the moving components) from entering the patient's body. In some examples, where the walls of the driveshaft 3620 has some porosity, fluid within the return fluid pathway 3634 may enter the inner lumen of the driveshaft 3620.

Optionally, clean fluid for the sheath fluid pathway 3630 and the catheter fluid pathway 3632 may be provided by a console 3606, which may include one or more clean fluid sources (e.g., saline bags) and a pump assembly (e.g., peristaltic pump assembly) for pushing clean fluid toward the blood pump 3602. In some examples, the clean fluid may be provided through a catheter fluid inlet and a sheath fluid inlet between the motor assembly 3604 and the blood pump 3602. In some cases, one or both of the catheter fluid inlet and the sheath fluid inlet are part of (or connected to) the motor assembly 3604. In some examples, the return fluid pathway 3634 may flow through the motor assembly 3604 and toward a waste reservoir, which optionally may be connected to (or part of) such as by being secured to, the console 3606.

Figure 37A:
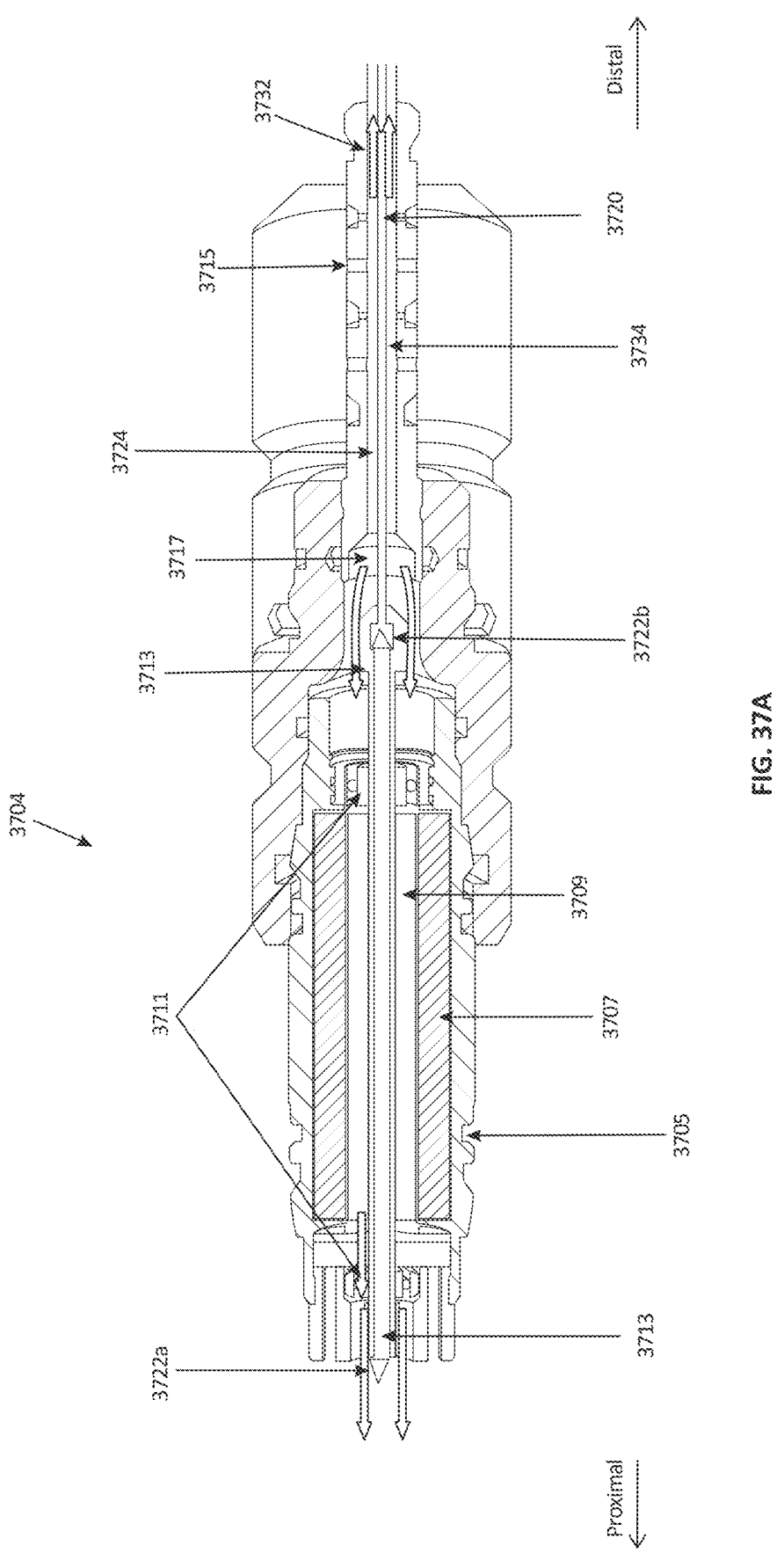
FIGS. 37A and 37B illustrate an exemplary external motor for an intravascular blood pump.
Figure 37B:
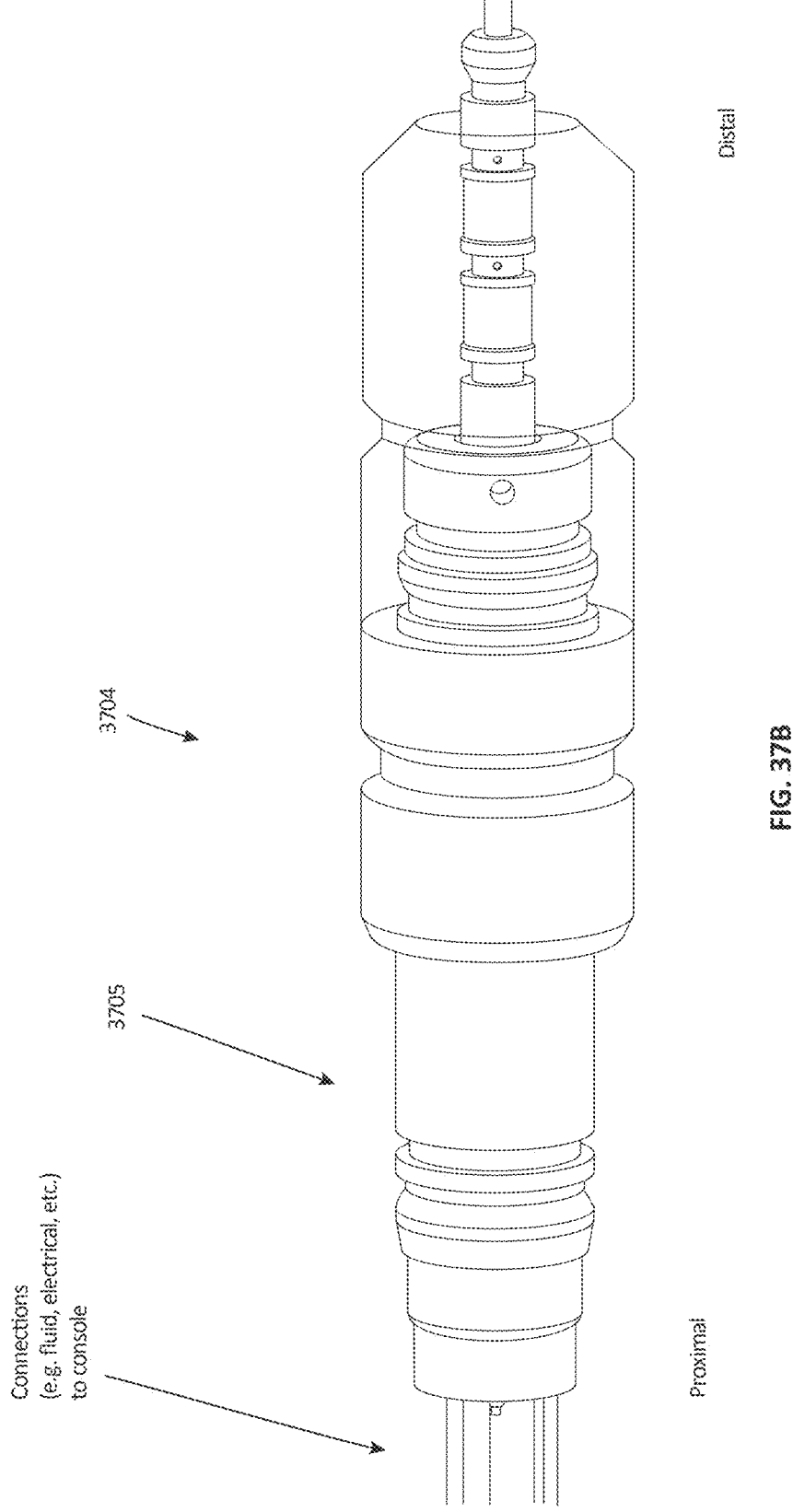

In some examples, the motor assembly 3604 is configured to allow fluid to pass therethrough to cool, lubricate and/or flush various internal components of the motor assembly 3604, as well as optionally providing a pathway for at least some of the return fluid through the system. FIGS. 37A and 37B illustrate an exemplary motor assembly 3704 showing an exemplary fluid pathway therethrough. Clean fluid (e.g., from the console) can enter an inlet 3715 that is, in this case, at a distal portion of the motor assembly 3704. The clean purge fluid 3732 can travel in a distal direction toward the blood pump radially outside of the catheter shaft 3724 and the inner hollow driveshaft 3720. The hollow driveshaft may be rotationally coupled with one or more impellers of the blood pump. In some examples, the clean purge fluid 3732 pushed toward the blood pump forms the catheter fluid pathway for cooling, lubricating and/or flushing one or more components of the blood pump, such as the driveshaft and/or one or more bearings in the pump section, such as any of the pump sections incorporated by reference herein.

At least some (e.g., nominally all) of the clean purge fluid 3732 returns from the blood pump as return purge fluid 3734 through the inner lumen of the catheter shaft 3724. The hollow driveshaft 3720 may be at least partially permeable to fluid such that some of the fluid within the catheter shaft 3724 seeps into the inner lumen of the hollow driveshaft 3720. The return purge fluid 3734 can travel proximally through the catheter shaft 3724 and exit an intersection region 3717.

From the intersection region 3717, the return fluid can be directed in an annular space around a hollow motor shaft 3713 that is rotationally coupled to the hollow driveshaft 3720. The return purge fluid can then be directed through spaces between rotational elements (e.g., balls) of a first bearing and into an annular space between a stator 3707 and a rotor 3709 of a motor 3705. The motor 3705 can be configured to rotate the hollow motor shaft 3713, which is rotationally coupled to the hollow driveshaft 3720. Moving further proximally, the return purge fluid can exit the motor 3705 through spaces between rotational elements (e.g., balls) of a second bearing and exit a proximal end of the motor assembly 3704. Once exited the motor assembly 3704, the return fluid may be directed to a waste reservoir, for example, at an external console of the blood pump system.

In some examples, the motor assembly 3704 optionally includes one or more one-way valves (e.g., 3722a and 3722b), which can prevent fluid from entering the hollow motor shaft 3713 within the motor 3705. This may keep that lumen of the hollow motor shaft 3713 clean in the event a guide wire needs to be advanced distally back through the blood pump through this lumen.

An exemplary benefit of the configuration shown in FIGS. 37A and 37B is that the return purge fluid 3734 running through the motor 3705 can keep the motor bearings 3711 lubricated. The return purge fluid 3734 may flush out debris in the bearings 3711. In some examples, rotary seals are not necessary since the motor 3705 can have sealed electronics and can function normally while filled with purge fluid. In this example, the return fluid path through the motor 3705 may provide some degree of motor cooling, although creating a pathway for return fluid to flow out of the blood pump system may be a more important design feature.

Figure 38:
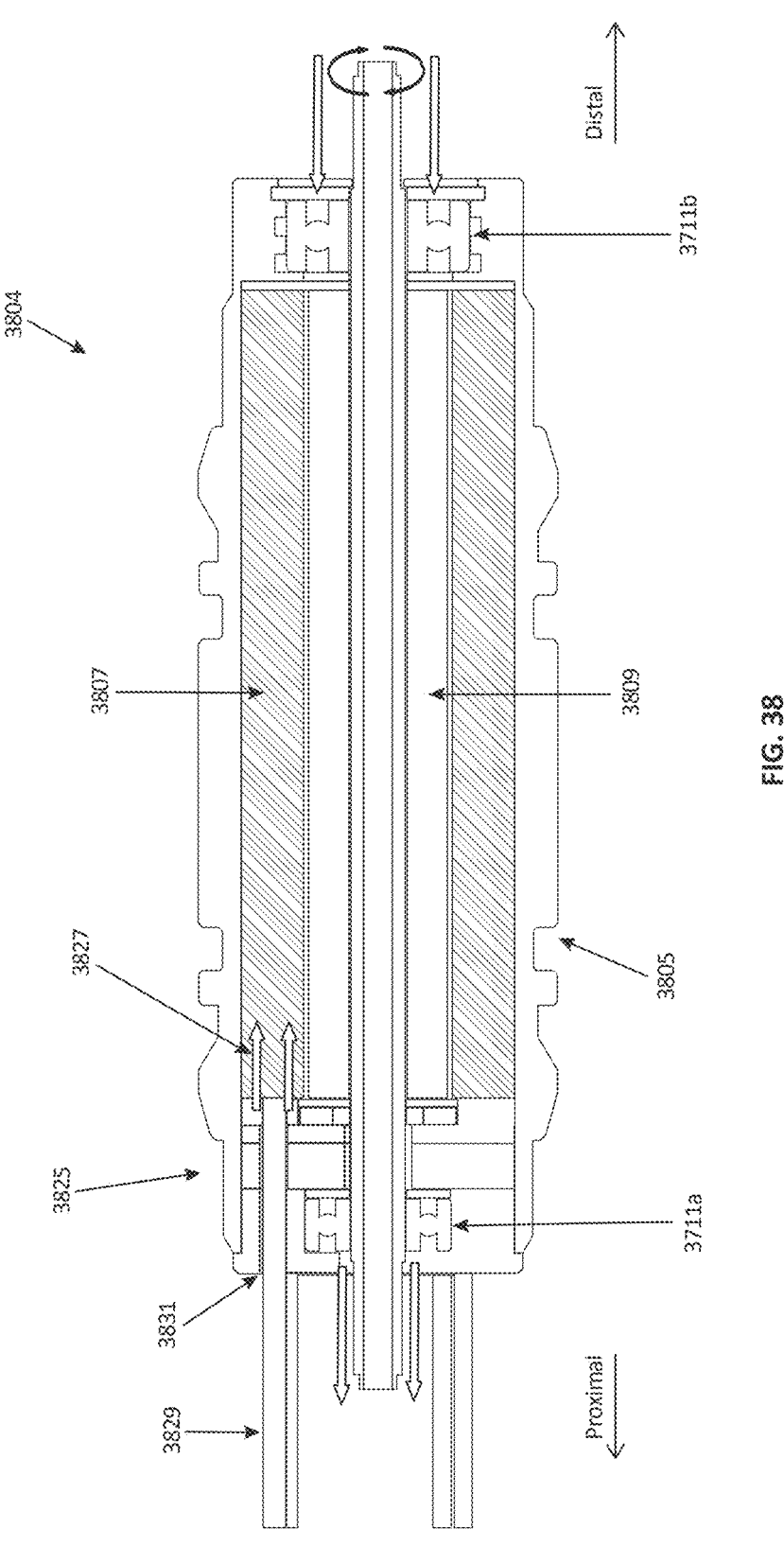
FIG. 38 illustrates a cross-section view of an exemplary external motor for an intravascular blood pump showing an exemplary fluid pathway and possible fluid ingress toward a stator motor component.

FIG. 38 shows an exemplary motor assembly 3804 of an intravascular blood pump, illustrating a possible fluid ingress site to a stator 3807. In this example, the fluid may be able to enter the stator 3807 around a wire connection region 3825 of the stator 3807 where wires 3829 exit the stator 3807. For example, fluid may enter spaces between the wires 3829 and the housing surrounding the motor 3805 if potting 3831 does not provide a sufficient fluid impermeable seal. Another possible path of fluid ingress may be at junctions between parts of the housing surrounding the motor 3805, such as the exemplary circumferential weld junction 3833. If such weld regions are improperly formed, these regions may also allow fluid to enter the stator 3807. Fluid ingress into the stator 3807 may cause an electrical short and/or cause the stator 3807 to corrode.

Figure 39:
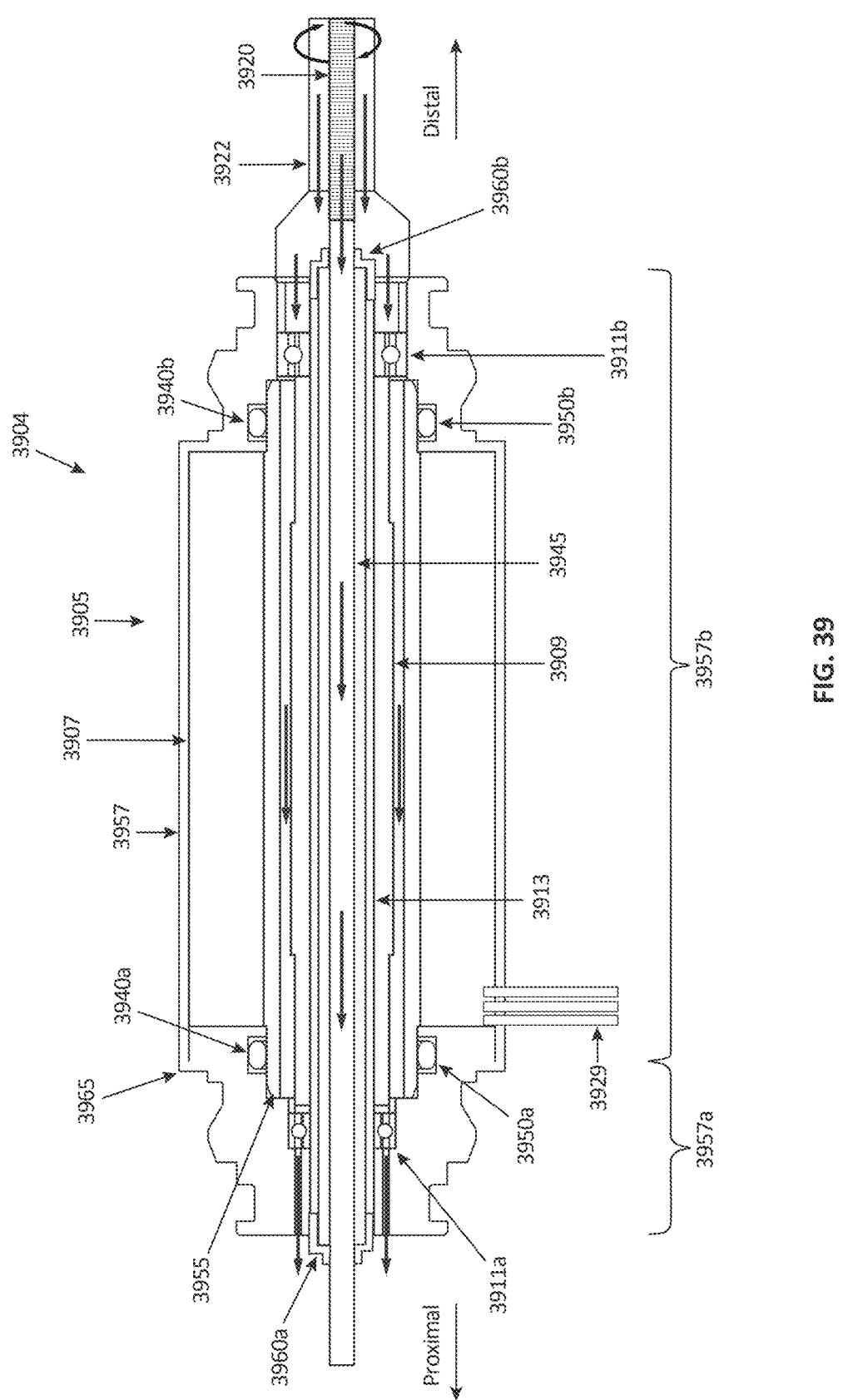
FIG. 39 illustrates a cross-section view of an exemplary external motor for an intravascular blood pump showing an exemplary isolation component to prevent ingress of fluid toward a stator motor component.

FIG. 39 illustrates an exemplary motor assembly 3904 configured to fluidically isolate the stator from the fluidic pathway, thereby addressing the fluid ingress problems described with respect to FIG. 38. In this example, a fluid impermeable layer 3955 is positioned between the stator 3907 and the rotor 3909. The fluid impermeable layer 3955 may act as a barrier to prevent fluid from the fluid pathway within the motor from reaching the stator 3907. The fluid impermeable layer 3955 may have a cylindrical shape with the rotor 3907 positioned within the inner lumen of the fluid impermeable layer 3955. The fluid impermeable layer 3955 may be made of a non-electrically conductive material to prevent interference with the functioning of the motor 3905. In some cases, the fluid impermeable layer 3955 comprises a polymer material. As shown, fluid (e.g., return purge fluid) may flow radially within the impermeable layer 3955 and radially outside of the rotor 3909.

The fluid impermeable layer 3955 may be secured in place within the motor assembly 3904. For example, the housing 3957 of the motor assembly 3904 may include multiple sections that are coupled (e.g., bonded, welded, or otherwise coupled) together with the fluid impermeable layer 3955 disposed therein. In the non-limiting example shown, the housing 3957 includes a first housing portion 3957a and a second housing portion 3957b that are coupled together by a circumferential weld 3965, thereby encasing the fluid impermeable layer 3955 within the housing 3957. In alternative examples, the housing may include other arrangements of a plurality of housing portions that are coupled together (at one or more coupling locations) to secure the fluid impermeable layer therein. For example, the housing may include more than two housing portions coupled together. Additionally, for example, first housing portion 3975a and second housing portion 3975b may be coupled (e.g., welded) in a distal portion of the motor assembly.

The motor assembly 3904 may include one or more sealing elements or members (e.g., one or more O-rings) strategically placed to prevent fluid from reaching the stator 3907. The exemplary motor assembly 3904 includes a first sealing element (e.g., O-ring in this example) 3950a proximally located with respect to the stator 3907 and a second O-ring 3950b distally located with respect to the stator 3907. These O-rings 3950a and 3950b positioned either side of the stator 3907 can be sized and positioned to prevent fluid from reaching the stator 3907 from axial directions. The O-rings 3950a and 3950b may be positioned within annular groves 3940a and 3940b of the motor assembly housing 3957. In some examples, the O-rings 3950a and 3950b are in contact with and form a seal with the fluid impermeable layer 3955.

In some examples, wires 3929 for the stator 3907 may be configured to extend radially outward from the stator 3907 so that their entry points into the stator 3907, which may be easy entry points for fluid ingress, are situated away from the fluid path. The wires 3929 may extend through a slot on an outer portion of the motor assembly housing 3957. In some examples, the wires 3929 enter a sealed handle compartment.

Example fluid pathways of return fluid from the blood pump through the exemplary motor assembly 3904 are shown in arrows in FIG. 39. As shown, the return fluid can enter from a distal side of the motor 3905 (relative to the console) via driveshaft tube 3922 that surrounds the rotatable driveshaft 3920. The driveshaft 3920 may be permeable to fluid such that some fluid within the driveshaft tube 3922 may enter within the inner lumen of the driveshaft 3920. The return fluid from the driveshaft tube 3922 and driveshaft 3920 travel two different fluid pathways through the motor 3905. In a first fluid pathway, fluid can travel though a distal bearing 3911b (e.g., to cool, lubricate and/or flush the distal bearing 3911b), in an annular space between the fluid impermeable layer 3955 and the rotor 3929 (e.g., to cool, lubricate and/or flush the rotor 3909 and/or stator 3907), through a proximal bearing 3911a (e.g., to cool, lubricate and/or flush the proximal bearing 3911a), and out a proximal end of the motor assembly 3904.

In a second fluid pathway through the motor 3905, fluid may travel through a hypotube 3945, which is rotatably coupled to the driveshaft 3920 (as shown), and out the proximal end of the motor assembly 3904. The hypotube 3945 can be positioned within the lumen of a hollow motor shaft 3913, which is rotatably coupled to the rotor 3909. The hypotube 3945 may be impermeable to fluid passage therethrough, thereby preventing fluid from entering in the annular space between the hypotube 3945 and the hollow motor shaft 3913. The hypotube 3945 may be rotatably coupled to the hollow motor shaft 3913 by couplers 3960a and 3960b, which may have annular shapes to accommodate the hypotube 3945 positioned therethrough. The hypotube 3945 may be configured to accommodate a guidewire therethrough. Return fluid exiting from the proximal side of the motor assembly 3904 can travel to a waste fluid line toward a waste fluid reservoir, for example.

Purge fluid as used herein may also be referred to as a lubricating fluid, flushing fluid and/or a cooling fluid, and vice versa.

The invention claimed is:

1. A blood pump system, comprising:
a catheter portion having a distal end including a blood pump, the blood pump having a driveshaft rotationally coupled to one or more impellers of the blood pump;
a clean fluid pathway configured to direct fluid distally into the catheter portion and the blood pump;
a return fluid pathway configured to direct fluid proximally from the blood pump into the catheter portion; and
an external motor assembly having a distal portion coupled to the catheter portion, the external motor assembly being configured to remain outside a patient's body while the blood pump is disposed within the patient's vascular system, the external motor assembly including a motor rotationally coupled to the driveshaft, wherein the motor includes:
a fluid impermeable layer disposed between a motor rotor and a motor stator; and
a return fluid inlet disposed at the distal portion of the external motor and in fluid communication with the return fluid pathway, the return fluid inlet configured to direct fluid from the return fluid pathway into an annular space between the fluid impermeable layer and the motor rotor, and out a proximal portion of the motor assembly, wherein the fluid impermeable layer is arranged to prevent fluid ingress toward the motor stator.

2. The blood pump system of claim 1, wherein the return fluid pathway directs fluid through a first bearing at the proximal portion of the external motor assembly and a second bearing at a distal portion of the external motor assembly, wherein the return fluid pathway directs fluid through spaces between rotational elements of the first and second bearings.

3. The blood pump system of claim 1, wherein the blood pump includes an expandable blood conduit and proximal and distal impellers within the expandable blood conduit.

4. The blood pump system of claim 1, wherein the catheter portion includes a clean fluid line configured to direct clean fluid toward the blood pump.

5. The blood pump system of claim 1, wherein the clean fluid pathway directs fluid through one or more of: an impeller of the blood pump, a bearing of the blood pump, a valve of the blood pump.

6. The blood pump system of claim 1, wherein the external motor assembly is part of a handle of the blood pump system.

7. The blood pump system of claim 1, wherein the catheter portion includes one or more wires configured to provide electrical communication between the blood pump and the external motor assembly.

8. The blood pump system of claim 1, wherein the proximal portion of the external motor assembly is coupled to a return fluid line configured to direct the fluid from the proximal portion of the external motor assembly toward a fluid waste reservoir.

9. The blood pump system of claim 1, wherein the proximal portion of the external motor assembly is coupled to one or more wires configured to provide electrical communication between the external motor assembly and a console of the blood pump system.

10. The blood pump system of claim 1, wherein the catheter portion includes a sheath fluid pathway and a catheter fluid pathway, the sheath fluid pathway configured to direct clean fluid distally within an annular space between an outer sheath and a catheter shaft of the catheter portion, the catheter fluid pathway configured to direct clean fluid distally within an annular space between the catheter shaft and a driveshaft tube of the catheter portion.

11. The blood pump system of claim 10, wherein the catheter fluid pathway is not in fluid communication with the sheath fluid pathway within the catheter portion.

12. The blood pump system of claim 10, wherein the sheath fluid pathway is configured to prevent blood accumulation in an annular space between a sheath and a catheter shaft at a distal end of the sheath.

13. The blood pump system of claim 10, wherein the sheath fluid pathway is configured to leak clean fluid into the patient's body at a distal end of the sheath.

14. The blood pump system of claim 1, wherein the return fluid pathway is radially within the fluid impermeable layer.

15. The blood pump system of claim 1, wherein the fluid impermeable layer has a cylindrical shape.

16. The blood pump system of claim 1, wherein the fluid impermeable layer is secured within the external motor assembly.

17. The blood pump system of claim 1, wherein the fluid impermeable layer is secured in place between at least a first section and a second section of an outer motor assembly housing that are coupled together.

18. The blood pump system of claim 17, wherein the first and second sections are welded together.

19. The blood pump system of claim 1, wherein the fluid impermeable layer is configured to prevent fluid ingress at a wire entry region of the motor stator.

20. The blood pump system of claim 1, wherein the motor assembly includes a first o-ring at a proximal side of the motor stator and a second o-ring at a distal side of the motor stator, wherein the first and second o-rings are configured to prevent fluid ingress toward the motor stator.

21. The blood pump system of claim 20, wherein the first and second o-rings are configured to prevent fluid ingress at a wire entry region of the motor stator.

* * * * *